United States Patent
Ahlquist et al.

(10) Patent No.: US 9,994,911 B2
(45) Date of Patent: *Jun. 12, 2018

(54) DETECTING NEOPLASM

(71) Applicants: Mayo Foundation for Medical Education and Research, Rochester, MN (US); EXACT SCIENCES DEVELOPMENT COMPANY, LLC, Madison, WI (US)

(72) Inventors: David A. Ahlquist, Rochester, MN (US); John B. Kisiel, Rochester, MN (US); William R. Taylor, Lake City, MN (US); Tracy C. Yab, Rochester, MN (US); Douglas W. Mahoney, Elgin, MN (US); Graham P. Lidgard, Madison, WI (US); Hatim T. Allawi, Middleton, WI (US)

(73) Assignees: MAYO FOUNDATION FOR MEDICAL EDUCATION AND RESEARCH, Rochester, MN (US); EXACT SCIENCES DEVELOPMENT COMPANY, LLC, Madison, WI (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/775,435

(22) PCT Filed: Mar. 12, 2014

(86) PCT No.: PCT/US2014/024589
§ 371 (c)(1),
(2) Date: Sep. 11, 2015

(87) PCT Pub. No.: WO2014/159652
PCT Pub. Date: Oct. 2, 2014

(65) Prior Publication Data
US 2016/0040246 A1 Feb. 11, 2016

Related U.S. Application Data

(60) Provisional application No. 61/784,429, filed on Mar. 14, 2013.

(51) Int. Cl.
*C07H 21/04* (2006.01)
*C12Q 1/68* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

| | | |
|---|---|---|
| 5,352,775 A | 10/1994 | Albertsen |
| 5,362,623 A | 11/1994 | Vogelstein |
| 5,527,676 A | 6/1996 | Vogelstein |
| 5,541,308 A | 7/1996 | Hogan et al. |
| 5,648,212 A | 7/1997 | Albertsen |
| 5,670,325 A | 9/1997 | Lapidus et al. |
| 5,691,454 A | 11/1997 | Albertsen |
| 5,741,650 A | 4/1998 | Lapidus et al. |
| 5,783,666 A | 7/1998 | Albertsen |
| 5,786,146 A | 7/1998 | Herman |
| 5,891,651 A | 4/1999 | Roche |
| 5,928,870 A | 7/1999 | Lapidus et al. |
| 5,952,178 A | 9/1999 | Lapidus et al. |
| 5,955,263 A | 9/1999 | Vogelstein |
| 6,020,137 A | 2/2000 | Lapidus |
| RE36,713 E | 5/2000 | Vogelstein |
| 6,090,566 A | 7/2000 | Vogelstein |
| 6,114,124 A | 9/2000 | Albertsen |
| 6,235,470 B1 | 5/2001 | Sidransky |
| 6,245,515 B1 | 6/2001 | Vogelstein |
| 6,413,727 B1 | 7/2002 | Albertsen |
| 6,630,314 B2 | 10/2003 | Nair et al. |
| 6,677,312 B1 | 1/2004 | Vogelstein |
| 6,800,617 B1 | 10/2004 | Vogelstein |
| RE38,916 E | 12/2005 | Vogelstein |

(Continued)

FOREIGN PATENT DOCUMENTS

| | | |
|---|---|---|
| CN | 102292458 | 12/2011 |
| EP | 2391729 | 12/2011 |

(Continued)

OTHER PUBLICATIONS

Lokk et al. PLoS ONE, vol. 7, No. 6, e398013, Jun. 2012.*

(Continued)

*Primary Examiner* — Jeanine A Goldberg
(74) *Attorney, Agent, or Firm* — Casimir Jones, SC; Robert A. Goetz

(57) ABSTRACT

Provided herein is technology relating to detecting neoplasia and particularly, but not exclusively, to methods, compositions, and related uses for detecting premalignant and malignant neoplasms such as pancreatic and colorectal cancer. Accordingly, provided herein is technology for pancreatic cancer screening markers and other gastrointestinal cancer screening markers that provide a high signal to-noise ratio and a low background level when detected from samples taken from a subject (e.g., stool sample). As described herein, the technology provides a number of methylated DNA markers and subsets thereof (e.g., sets of 2, 3, 4, 5, 6, 7, 8, 9, 10, 11, 12 or more markers) with high discrimination for G1 neoplasms overall and/or at individual tumor sites.

3 Claims, 3 Drawing Sheets

(56) References Cited

U.S. PATENT DOCUMENTS

| | | | |
|---|---|---|---|
| 7,037,650 | B2 | 5/2006 | Gonzalgo et al. |
| 7,087,583 | B2 | 8/2006 | Vogelstein |
| 7,267,955 | B2 | 9/2007 | Vogelstein |
| 7,368,233 | B2 | 5/2008 | Shuber et al. |
| 7,432,050 | B2 | 10/2008 | Markowitz |
| 7,485,402 | B2 | 2/2009 | Arai |
| 7,485,418 | B2 | 2/2009 | Goggins et al. |
| 8,361,720 | B2 | 1/2013 | Oldham-Haltom |
| 8,808,990 | B2 | 8/2014 | Lidgard et al. |
| 8,969,046 | B2 | 3/2015 | Van Engeland et al. |
| 8,980,107 | B2 | 3/2015 | Domanico et al. |
| 8,993,341 | B2 | 3/2015 | Bruinsma et al. |
| 8,999,176 | B2 | 4/2015 | Domanico et al. |
| 9,000,146 | B2 | 4/2015 | Bruinsma et al. |
| 9,506,116 | B2 * | 11/2016 | Ahlquist ............ C12Q 1/6886 |
| 2003/0143606 | A1 | 7/2003 | Olek et al. |
| 2003/0224040 | A1 | 12/2003 | Baylin et al. |
| 2004/0234960 | A1 | 11/2004 | Hogan |
| 2006/0253259 | A1 | 11/2006 | Fernandez |
| 2007/0054295 | A1 | 3/2007 | Spivack |
| 2008/0039413 | A1 | 2/2008 | Morris et al. |
| 2008/0081333 | A1 | 4/2008 | Mori et al. |
| 2008/0213870 | A1 | 9/2008 | Cao et al. |
| 2009/0208505 | A1 | 8/2009 | Samuels |
| 2010/0167940 | A1 | 7/2010 | Feinberg |
| 2010/0317000 | A1 | 12/2010 | Zhu |
| 2011/0136687 | A1 | 6/2011 | Olek et al. |
| 2011/0183328 | A1 | 7/2011 | Taylor et al. |
| 2011/0287968 | A1 | 11/2011 | Weinhausel et al. |
| 2011/0318738 | A1 | 12/2011 | Jones et al. |
| 2012/0034605 | A1 | 2/2012 | Hinoda et al. |
| 2012/0053073 | A1 | 3/2012 | Kassis et al. |
| 2012/0122088 | A1 | 5/2012 | Zou |
| 2012/0122106 | A1 | 5/2012 | Zou |
| 2012/0164110 | A1 | 6/2012 | Feinberg et al. |
| 2012/0164238 | A1 | 6/2012 | Joost |
| 2013/0012410 | A1 | 1/2013 | Lou et al. |
| 2013/0022974 | A1 | 1/2013 | Chinnaiyan |
| 2013/0065228 | A1 | 3/2013 | Hinoue et al. |
| 2013/0244235 | A1 | 9/2013 | Ahlquist et al. |
| 2013/0288247 | A1 | 10/2013 | Mori et al. |
| 2014/0057262 | A1 | 2/2014 | Ahlquist et al. |
| 2014/0137274 | A1 | 5/2014 | Ishikawa |
| 2014/0162894 | A1 | 6/2014 | Hatchwell et al. |
| 2014/0193813 | A1 | 7/2014 | Bruinsma et al. |
| 2014/0194607 | A1 | 7/2014 | Bruinsma et al. |
| 2014/0194608 | A1 | 7/2014 | Bruinsma et al. |
| 2014/0274748 | A1 | 9/2014 | Ahlquist et al. |
| 2014/0358448 | A1 | 12/2014 | Tai et al. |
| 2015/0126374 | A1 * | 5/2015 | Califano ............ C12Q 1/6886 506/2 |
| 2015/0240318 | A1 | 8/2015 | Van Engeland et al. |
| 2016/0194723 | A1 | 7/2016 | Louwagie |

FOREIGN PATENT DOCUMENTS

| | | |
|---|---|---|
| WO | 00/26401 | 5/2000 |
| WO | 2007/116417 | 10/2007 |
| WO | WO 2008/084219 | 7/2008 |
| WO | 2010/086389 | 8/2010 |
| WO | WO 2010/089538 | 8/2010 |
| WO | 2011/119934 | 9/2011 |
| WO | 2011/126768 | 10/2011 |
| WO | 2012/088298 | 6/2012 |
| WO | 2012/155072 | 11/2012 |
| WO | 2012/175562 | 12/2012 |
| WO | 2016/097120 | 6/2016 |

OTHER PUBLICATIONS

Feng (PNAS 2010 vol. 107 No. 19 pp. 8689-8694).*
Esteller et al. (Cancer Research, vol. 58, pp. 4515-4518, Oct. 1998).*
Anderson et al. (Am. J. of Gastroenterology, Abstracts S1033, Oct. 2015).*
Kisiel et al. (Clinical Cancer Research, vol. 21, No. 19, pp. 4473-4481, May 28, 2015).*
Pao et al. (Human Molecular Genetics, vol. 10, No. 9, pp. 903-910).*
Cameron et al. (Blood, vol. 94, No. 7, pp. 2445-2451, Oct. 1999).*
Kisiel et al. (AGA Abstracts #469, S-84, May 2013) (Year: 2013).*
Raimondo et al. (AGA Abstracts, S-90, May 2013) (Year: 2013).*
Eva Baxter (The University of Edinburgh, PhD, "Investigating the association between BRAFv600e and methylation in sporadic colon cancer", 2011) (Year: 2011).*
Supplementary Partial European Search Report, EP Application No. 14776150.6, dated Sep. 29, 2016.
Chen "Expression and promoter methylation analysis of ATP-binding cassette genes in pancreatic cancer" Oncology Reports, 2012, 27:265-269.
Toyota, et al. (1999). "Identification of differentially methylated sequences in colorectal cancer by methylated CpG island amplification." Cancer Res. 59: 2307-2312.
Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Vincent et al. "Genome-wide analysis of promoter methylation associated with gene expression profile in pancreatic adenocarcinoma." Clinical cancer research : an official journal of the American Association for Cancer Research. 2011; 17:4341-54.
Watanabe, t., International Journal of Oncology (2011), 38, pp. 201-207.
Wheeler et al. "Hypermethylation of the promoter region of the E-cadherin gene (CDH1) in sporadic and ulcerative colitis associated colorectal cancer." Gut (2001), 48, pp. 367-371.
Wu, Gastroenterology (2011) 14: S-222.
Xiong, et al. (1997). Nucleic Acids Res. 25 (12): 2532-2534.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention : a publication of the American Association for Cancer Research, cosponsored by the American Society of Preventive Oncology. 2009;18:3000-7.
Zhang et al. (2009). "DNA methylation analysis of chromosome 21 gene promoters at single base pair and single allele resolution." PLoS Genet. 5 (3): e1000438.
Zhao et al. "Genome-wide identification of Epstein-Barr virus-driven promoter methylation profiles of human genes in gastric cancer cells." Cancer. 2013;119:304-12.
Zou H., et al., "A Sensitive Method to Quantify Human Long DNA in Stool: Relevance to Colorectal Cancer Screening." Cancer Epidemiol Biomarkers Prev 2006;15:1115-9.
Zou H.Z. et al., "Detection of aberrant p16 methylation in the serum of colorectal cancer patients." Clin Cancer Res 2002;8(1):188-91.
Zou, et al.(2007). "Highly methylated genes in colorectal neoplasia: implications for screening." Cancer Epidemial Biomarkers Prev. 16: 2686-2696.
Zou, et al. (2009). "T2036 Pan-Detection of Gastrointestinal Neoplasms by Stool DNA Testing Establishment of Feasibility." Gastroenterology. 136: A-625.
Kisiel et al. (AGA Abstracts, VS-68, vol. 138, No. 5, May 2010).
Kisiel et al. "Stool DNA testing for the detection of pancreatic cancer: assessment of methylation marker candidates." Cancer. 2012; 118:2623-31.
Kisiel, et al. (2011). "Stool DNA screening for colorectal cancer: opportunities to improve value with next generation tests." J Clin Gastroenterol. 45 (4): 301-8.
Kober et al. "Methyl-CpG binding column-based identification of nine genes hypermethylated in colorectal cancer." Molecular carcinogenesis. 2011; 50:846-56.

(56) References Cited

OTHER PUBLICATIONS

Kraus, et al., "Inflammation and colorectal cancer," Current Opinion in Pharmacology, vol. 9, No. 4, pp. 405-410 (2009).
Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.
Laird. (2010). "Principles and challenges of genome-wide DNA methylation analysis." Nat Rev Genet. 11: 191-203.
Lashner BA, Am J Gastroenterol (1999), 94, pp. 456-462.
Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.
Leung W.K., et al., "Detection of epigenetic changes in fecal DNA as a molecular screening test for colorectal cancer: A feasibility study." Clin Chem 2004; 50(11):2179-82.
Levin B, Gastroenterology (2008); 134, pp. 1570-1595.
Li et al. "Association between Galphai2 and ELMO1/Dock180 connects chemokine signalling with Rac activation and metastasis." Nat Commun. 2013; 4:1706.
Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.
Lin, et al., Identification of disease-associated DNA methylation in intestinal tissues from patients with inflammatory bowel disease, Clinical Genetics, vol. 80, No. 1, pp. 59-67 (2011).
Liu et al. "Medulloblastoma expresses CD1d and can be targeted for immunotherapy with NKT cells." Clin Immunol. 2013;149:55-64.
Ma, et al. (2011). "MicroRNA-616 induces androgen-independent growth of prostate cancer cells by suppressing expression of tissue factor pathway inhibitor TFPI-2." Cancer Res. 71: 583-592.
Maeda, et al., "DNA hypermethylation in colorectal neoplasms and inflammatory bowel disease: a mini review," Inflammapharmacology, vol. 14, No. 5-6, pp. 204-206 (2006).
Matsubayashi, et al. (2006). "DNA methylation alterations in the pancreatic juice of patients with suspected pancreatic disease." Cancer Res. 66: 1208-1217.
Meissner et al. (2008). "Genome-scale DNA methylation maps of pluripotent and differentiated cells." Nature. 454: 766-70.
Melotte et al., (JNCL, vol. 101, No. 13, pp. 916-927, Jul. 2009).
Muller H.M., et al., "Methylation changes in faecal DNA: a marker for colorectal cancer screening?" The Lancet 2004;363:1283-5.
Obusez et al. (Inflammatory Bowel Diseases: vol. 14, Issue pS42, Dec. 2008, P-0106).
Obusez et al. (Int. J. Colorectal Dis. vol. 26, pp. 951-953, 2011).
Odze RD, Am J Surg Pathol (2000), 24, pp. 1209-1216.
Olaru, et al., "Unique patterns of CpG island methylation in inflammatory bowel disease-associated colorectal cancers," Inflammatory Bowel Diseases, vol. 18, No. 4, pp 641-648 (Epub Aug. 9, 2011).
Olson, J et al. "DNA Stabilization Is Critical for Maximizing Performance of Fecal DNA-Based Colorectal Cancer Tests" Diagn Mol Pathol (2005) 14, pp. 183-191.
Omura, et al. (2008). "Genome-wide profiling of methylated promoters in pancreatic adenocarcinoma." Cancer Biol Ther. 7 (7): 1146-1156.
Omura, et al. (2009). "Epigenetics and epigenetic alterations in pancreatic cancer." Int. J. Clin Exp Pathol. 2: 310-326.
Osborn NK, and Ahlquist DA, "Stool screening for colorectal cancer: molecular approaches." Gastroenterology 2005;128:192-206.
Osborn, et al., "Aberrant methylation of the eyes absent 4 gene in ulcerative colitis-associated dysplasia," Clinical Gastroenterology and Hepatology, vol. 4, No. 2, pp. 212-218 (2006).
Oster, B. et al., "Identification and validation of highly frequent CpG island hypermethylation in colorectal adenomas and carcinomas." Int J Cancer. 2011;129(12):2855-66.

Person et al. "Chronic cadmium exposure in vitro induces cancer cell characteristics in human lung cells." Toxicol Appl Pharmacol. 2013; 273(2):281-8.
Petko Z., et al., "Aberrantly Methylated CDKN2A, MGMT, and MLH1 in Colon Polyps and in Fecal DNA from Patients with Colorectal Polyps." Clin Cancer Res 2005;11:1203-9.
Raimondo et al. "Methylated DNA Markers in Pancreatic Juice Discriminate Pancreatic Cancer From Chronic Pancreatitis and Normal Controls" Gastroenterology 2013; 144:S-90.
Rex et al. "American College of Gastroenterology guidelines for colorectal cancer screening 2008." Am J Gastroenterol (2009); 104, pp. 739-50.
Sadri and Hornsby "Rapid Analysis of DNA Methylation Using New Restriction Enzyme Sites Created by Bisulfite Modification." (1996) Nucl. Acids Res. 24: 5058-5059.
Sato et al., "Aberrant methylation of the HPP1 gene in ulcerative colitis-associated colorectal carcinoma." Cancer Res (2002), 62, pp. 6820-6822.
Sato, et al. (2003). "Discovery of novel targets of aberrant methylation in pancreatic carcinoma using high-throughput microarrays." Cancer Res. 63: 3735-3742.
Sato, et al. (2008). "CpG island methylation profile of pancreatic intraepithelial neoplasia." Mod Pathol. 21 93): 238-244.
Schulmann, et al., Molecular phenotype of inflammatory bowel disease-associated neoplasms with microsatellite instability, Gastroenterology, vol. 129, No. 1, pp. 74-85 (2005).
Seshagiri et al. "Recurrent R-spondin fusions in colon cancer." Nature. 2012; 488:660-4.
Shin et al. "Bile-based detection of extrahepatic cholangiocarcinoma with quantitative DNA methylation markers and its high sensitivity." The Journal of molecular diagnostics : JMD. 2012;14:256-63.
Singer-Sam et al. "A quantitative HpaII-PCR assay to measure methylation of DNA from a small number of cells" (1990) Nucl. Acids Res. 18(3): 687.
Singer-Sam et al. "A sensitive, quantitative assay for measurement of allele-specific transcripts differing by a single nucleotide." (1992) PCR Methods Appl. 1: 160-163.
Stumm et al. "Strong expression of the neuronal transcription factor FOXP2 is linked to an increased risk of early PSA recurrence in ERG fusion-negative cancers." Journal of clinical pathology. 2013;66:563-8.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tang, et al. (2010). "Prognostic significance of tissue factor pathway inhibitor 2 in pancreatic carcinoma and its effect on tumor invasion and metastatis." Med Oncol. 27: 867-875.
Taylor et al. "Expression of p53 in colorectal cancer and dysplasia complicating ulcerative colitis." Br J Surg (1993), 80, pp. 442-444.
Tonack, et al. (2009). "Pancreatic cancer: proteomic approaches to a challenging disease." Pancreatology. 9: 567-576.
Buck et al. "Design Strategies and Performance of Custom DNA Sequencing Primers" Biotechniques, 1999, 27(3): 528-536.
Naumov "Genome-scale analysis of DNA methylation in colorectal cancer using Infinium HumanMethylation450 BeadChips" Epigenetics, 2013, vol. 8, issue 9, pp. 921-934.
Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Sen-Yo et al. "TWIST1 hypermethylation is observed in pancreatic cancer" Biomedical Reports; 1:33-33, 2013.
Ahlquist D et al. (2010) "Next Generation Stool DNA Testing for Detection of Colorectal Neoplasia—Early Marker Evaluation", presented at Colorectal Cancer: Biology to Therapy, American Association for Cancer Research.

(56) References Cited

OTHER PUBLICATIONS

Ahlquist D.A. et al., "Novel use of hypermethylated DNA markers in stool for detection of colorectal cancer: a feasibility study." Gastroenterology, 2002;122(Suppl):A40.

Ahlquist D.A., et al., "Colorectal cancer screening by detection of altered human DNA in stool: feasibility of a multitarget assay panel." Gastroenterology, 2000, 119(5):1219-27.

Ahlquist et al., "Next-generation stool DNA test accurately detects colorectal cancer and large adenomas." Gastroenterology (2012), 142, pp. 248-256.

Asai et al. "IKZF1 deletion is associated with a poor outcome in pediatric B-cell precursor acute lymphoblastic leukemia in Japan." Cancer Med. 2013; 2:412-9.

Aust DE, "Mutations of the BRAF gene in ulcerative colitis-related colorectal carcinoma." Int. J. Cancer (2005), 115, pp. 673-677.

Azuara et al. "Novel Methylation Panel for the Early Detection of Colorectal Tumors in Stool DNA." Clinical Colorectal Cancer, vol. 9, No. 3, pp. 168-176, Jul. 2010.

Belinsky S.A., et al., "Promoter Hypermethylation of Multiple Genes in Sputum Precedes Lung Cancer Incidence in a High-Risk Cohort." Cancer Res, 2006;66:3338-44.

Bell et al., "c-Ki-ras gene mutations in dysplasia and carcinomas complicating ulcerative colitis." Br J Cancer (1991), 64, pp. 174-178.

Biankin et al (2003) "Molecular pathogenesis of precursor lesions of pancreatic ductal adenocarcinoma" Pathology 35:14-24.

Brune, et al. (2008). "Genetic and epigenetic alterations of familial pancreatic cancers." Cancer Epidemiol Biomarkers Prev. 17 (12): 3536-3542.

Cairns et al., "Guidelines for colorectal cancer screening and surveillance in moderate and high risk groups." Gut (2010); 59, pp. 666-689.

Cameron et al (1995) "Adenocarcinoma of the esophagogastric junction and Barrett's esophagus" Gastroenterology 109: 1541-1546.

Camoes et al. "Potential downstream target genes of aberrant ETS transcription factors are differentially affected in Ewing's sarcoma and prostate carcinoma." PLoS ONE 2012;7:e49819.

Campbell et al. "Aberrant expression of the neuronal transcription factor FOXP2 in neoplastic plasma cells." British journal of haematology. 2010; 149:221-30.

Chen W.D., et al., "Detection in Fecal DNA of Colon Cancer-Specific Methylation of the Nonexpressed Vimentin Gene." J Natl Cancer Inst 2005;97:1124-32.

Eads, et al. (1999). "CpG island hypermethylation in human colorectal tumors is not associated with DNA methyltransferase overexpression." Cancer Res. 59: 2302-2306.

Ebert M.P., et al., "Aristaless-like homeobox-4 gene methylation is a potential marker for colorectal adenocarcinomas." Gastroenterology 2006;131:1418-30.

Edge, S.; Fritz, A.G.; Greene, F.L.; Trotti, A. (Eds.), AJCC Cancer Staging Manual. 7th ed: Springer, New York; 2010; Book—only table of contents provided.

Garrity-Park et al. "Methylation status of genes in non-neoplastic mucosa from patients with ulcerative colitis-associated colorectal cancer." Am J Gastroenterol (2010), 105, pp. 1610-1619.

Glockner, et al. (2009). "Methylation of TFPI2 in stool DNA: a potential novel biomarker for the detection of colorectal cancer." Cancer Res. 69: 4691-4699.

Goggins, M. "Molecular markers of early pancreatic cancer." J Clin Oncol 2005; 23: 4524.

Gonzalgo, et al. (1997) "Identification and characterization of differentially methylated regions of genomic DNA by methylation-sensitive arbitrarily primed PCR." Cancer Res. 57: 594-599.

Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.

Grady W.M., et al., "Detection of Aberrantly Methylated hMLH1 Promoter DNA in the Serum of Patients with Microsatellite Unstable Colon Cancer 1." Cancer Res, 2001;61:900-2.

Grutzmann et al., "Sensitive Detection of Colorectal Cancer in Peripheral Blood by Septin 9 DNA Methylation Assay." PLoS ONE (2008), 3:e3759.

Gu et al. "Genome-scale DNA methylation mapping of clinical samples at single-nucleotide resolution." Nat Methods. 2010; 7:133-6.

Gu, et al. (2011). "Preparation of reduced representation bisulfite sequencing libraries for genome-scale DNA methylation profiling." Nature Protocols. 6 (4): 468-481.

Gurung et al. "Menin epigenetically represses Hedgehog signaling in MEN1 tumor syndrome." Cancer research. 2013;73:2650-8.

Herman, et al. (1996). "Methylation-specific PCR: A novel PCR assay for methylation status of CpG islands." Proc. Natl. Acad. Sci. USA. 93: 9821-9826.

Hibi et al. (2010) "Methylation of the TFPI2 gene is frequently detected in advanced gastric carcinoma" Anticancer Res 30: 4131-3.

Hibi, et al. (2010). "Methylation of TFPI2 gene is frequently detected in advanced well-differentiated colorectal cancer." Anticancer Res. 30: 1205-1207.

Hirota et al., "pS2 expression as a possible diagnostic marker of colorectal carcinoma in ulcerative colitis." Oncol Rep (2000), 7, pp. 233-239.

Holzmann et al., "Comparative analysis of histology, DNA content, p53 and Ki-ras mutations in colectomy specimens with long-standing ulcerative colitis." Int J Cancer (1998) 76, pp. 1-6.

Hong, et al. (2008). "Multiple genes are hypermethylated in intraductal papillary mucinous neoplasms of the pancreas." Mod Pathol. 21 912): 1499-1507.

Hoque M.O. et al., "Quantitative methylation-specific polymerase chain reaction gene patterns in urine sediment distinguish prostate cancer patients from control subjects." J Clin Oncol, 2005;23:6569-75.

Howe, et al., "Annual report to the nation on the status of cancer, 1975-2003, featuring cancer among U.S. Hispanic/Latino populations." Cancer (2006) 107, pp. 1711-1742.

Imperiale et al., "Fecal DNA versus fecal occult blood for colorectal-cancer screening in an average-risk population." N Engl J Med (2004), 351, pp. 2704-2714.

International Search Report and Written Opinion, Int'l Patent Application No. PCT/US2015/022749, dated Aug. 19, 2015, 12 pages.

International Search Report and Written Opinion, Int'l Patent Application No. PCT/US2015/022751, dated Aug. 26, 2015, 25 pages.

International Search Report dated Jun. 10, 2013 from related International Patent Application No. PCT/US2013/027227.

Issa et al., "Accelerated Age-related CpG Island Methylation in Ulcerative Colitis." Cancer Res (2001), 61, pp. 3573-3577.

Itzkowitz S.H., et al., "Improved fecal DNA test for colorectal cancer screening." Clin Gastroenterol Hepatol 2007;5:111-7.

Itzkowitz et al. "Diagnosis and management of dysplasia in patients with inflammatory bowel diseases." Gastroenterology (2004) 126, pp. 1634-1648.

Jacobs et al. "Dysregulated methylation at imprinted genes in prostate tumor tissue detected by methylation microarray." BMC Urol. 2013;13:37.

Jess et al., "Risk of intestinal cancer in inflammatory bowel disease: a population-based study from olmsted county, Minnesota." Gastroenterology (2006) 130, pp. 1039-1046.

Jiao et al. "Somatic mutations in the Notch, NF-KB, PIK3CA, and Hedgehog pathways in human breast cancers." Genes, chromosomes & cancer. 2012; 51:480-9.

Kaiser. (2008). "Cancer genetics. A detailed genetic portrait of the deadliest human cancers." Science. 321: 1280-1281.

Kann L., et al., "Improved marker combination for detection of de novo genetic variation and aberrant DNA in colorectal neoplasia." Clin Chem 2006;52:2299-302.

Kawai, et al. (1994). "Comparison of DNA methylation patterns among mouse cell lines by restriction landmark genomic screening." Mol. Cell Biol. 14 (11): 7421-7427.

Ruppenthal et al. "TWIST1 Promoter Methylation in Primary Colorectal Carcinoma" Pathol. Oncol. Res., 2011, 17:867-872.

(56) References Cited

OTHER PUBLICATIONS

Baxter, Eva "Investigating the association between BRAFv600E and methylation in sporadic colon cancer" PhD The University of Edinburgh, 2011.
Anderson et al. Am. J. Of Gastroenterology, Abstracts S1033, Oct. 2015.
Cameron et al. Blood, vol. 94, No. 7, pp. 2445-2451, Oct. 1999.
Esteller et al. "Inactivation of Glutathione S-Transferase P1 Gene by Promoter Hypermethylation in Human Neoplasia" Cancer Resarch, vol. 58, pp. 4515-4518, Oct. 1998.
Feng "Conservation and divergence of methylation patterning in plants and animals" PNAS 2010 vol. 107, No. 19, pp. 8689-8694.
Pao et al. "The endothelin receptor B (EDNRB) promoter displays heterogeneous, site specific methylation patterns in normal and tumor cells" Human Molecular Genetics, vol. 10, No. 9, pp. 903-910.
Abbaszadegan, "Stool-based DNA testing, a new noninvasive method for colorectal cancer screening, the first report from Iran," World Journal of gastroenterology: WJG, vol. 13, p. 1528-1533, 2007.
Ahlquist et al., 1984, "HemoQuant, a new quantitative assay for fecal hemoglobin. Comparison with Hemoccult." Ann Intern Med, 101: 297-302.
Ahlquist et al., 1985, "Fecal blood levels in health and disease. A study using HemoQuant." N Engl J Med, 312: 1422-8.
Ahlquist et al., 1989, "Patterns of occult bleeding in asymptomatic colorectal cancer." Cancer, 63: 1826-30.
Ahlquist et al., 1993, "Accuracy of fecal occult blood screening for colorectal neoplasia. A prospective study using Hemoccult and HemoQuant tests." JAMA, 269: 1262-7.
Ahlquist et al., 2000, "Colorectal cancer screening by detection of altered human DNA in stool: feasibility of a multitarget assay panel." Gastroenterology, 119: 1219-27.
Ahlquist et al., 2008, "Stool DNA and occult blood testing for screen detection of colorectal neoplasia." Ann Intern Med, 149: 441-501.
Allison et al., 2007, "Screening for colorectal neoplasms with new fecal occult blood tests: update on performance characteristics." J Natl Cancer Inst, 99: 1462-70.
Crespi et al. "Colorectal cancer: a spreading but preventable disease" European Journal of Oncology. vol. 13(1). Mar. 2008. pp. 21-32.
De Kok, 2003, "Quantification and integrity analysis of DNA in the stool of colorectal cancer patients may represent a complex alternative to fecal occult blood testing." Clin Chem, 49: 2112-3.
Grutzmann, et al. (2008), "Sensitive detection of colorectal cancer in peripheral blood by septin—DNA methylation assay," PLoS ONE 3(11): e3759 which is 8 pages long.
Guzinska-Ustymowicz et al., (2009), "Correlation between proliferation makers: PCNA, Ki-67, MCM-2 and antiapoptotic protein Bcl2 in colorectal cancer," Anticancer Research. 29:3049-3052.
Hardcastle et al., 1996, "Randomised controlled trial of faecal-occult-blood screening for colorectal cancer." Lancet, 348: 1472-7.
Harewood et al., 2000, "Fecal occult blood testing for iron deficiency: a reappraisal." Dig Dis, 18(2): 75-82.
Harewood et al., 2002, "Detection of occult upper gastrointestinal tract bleeding: performance differences in fecal occult blood tests." Mayo Clin Proc, 77: 23-28.
Heresbach et al., 2006, "Review in depth and meta-analysis of controlled trials on colorectal cancer screening by faecal occult blood test." Eur J Gastroenterol Hepatol, 18: 427-33.
Hoang et al., 1997, "BAT-26, an indicator of the replication error phenotype in colorectal cancers and cell lines." Cancer Res, 57: 300-3.
Imperiale et al. "Multitarget Stool DNA Testing for Colorectal-Cancer Screening" New England Journal of Medicine, vol. 370, No. 14, Apr. 3, 2014, pp. 1287-1297.
Imperiale et al., 2004, "Fecal DNA versus fecal occult blood for colorectal-cancer screening in an average-risk population." N Engl J Med, 351: 2704-14.

International Search Report and Written Opinion dated Dec. 28, 2011 from International Patent Application No. PCT/US2011/029959, international filing date Mar. 25, 2011.
Jemal et al., 2007, "Cancer statistics, 2007." CA Cancer J Clin, 57: 43-66.
Kariya et al., 1987, "Revision of consensus sequence of human Alu repeats—a review." Gene, 53: 1-10.
Kim, H., et al., "Noninvasive molecular biomarkers for the detection of colorectal cancer," BMB Reports, 2008, vol. 41, No. 10, pp. 685-692.
Kronborg et al., 1996, "Randomised study of screening for colorectal cancer with faecal-occult-blood test." Lancet, 348: 1467-71.
Kronborg et al., 2004, "Randomized study of biennial screening with a faecal occult blood test: results after nine screening rounds." Scand J Gastroenterol, 39: 846-51.
Levin et al., 2008, "Screening and surveillance for the early detection of colorectal cancer and adenomatous polyps, 2008: a joint guideline from the American Cancer Society, the US Multi-Society Task Force on Colorectal Cancer, and the American College of Radiology." CA Cancer J Clin, 58: 130-60.
Mandel et al., 1993, "Reducing mortality from colorectal cancer by screening for fecal occult blood. Minnesota Colon Cancer Control Study." N Engl J Med, 328: 1365-71.
Meissner, 2006, "Patterns of colorectal cancer screening uptake among men and women in the United States." Cancer Epidemiol Biomarkers Prev, 15: 389-94.
Melle, et al. (2005), "Discovery and identification of a-defensins as low abundant, tumor-derived serum markers in colorectal cancer," 129(1): 66-73 abstract only.
Melotte, et al., (Jul. 1, 2009): "N-myc downstream-regulated gene 4 (NDRG4): a candidate tumor suppressor gene and potential biomarker for colorectal cancer," J. Natl Cancer Inst 101: 916-927.
Meuwis, "Contribution of proteomics to colorectal cancer diagnosis," Acta Endoscopica, vol. 37, p. 295-303, including translation, 2007.
Muller et al., 2004, "Methylation changes in faecal DNA: a marker for colorectal cancer screening?" Lancet, 363: 1283-5.
Nosho, et al. (2008): "PIK3CA mutation in colorectal cancer: Relationship with genetic and epigenetic alterations," Neoplasia. 10(6) 034-541, abstract only.
Olson et al., 2005, "DNA stabilization is critical for maximizing performance of fecal DNA-based colorectal cancer tests." Diagn Mol Pathol, 14: 183-91.
Osborn et al., 2005, "Stool screening for colorectal cancer: molecular approaches." Gastroenterology, 128: 192-206.
Park, et al. (2002), "Expressiono f melanoma antigen-encoding genes (MAGE) by common primers for MAGE-A1 to -A6 in colorectal carcinomas among Koreans," J. Korean Med. Sci 17: 497-501.
Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.
Sambrook et al., 1989, Fritsch, E.F., Maniatis, T. (ed.), Molecular Cloning, Cold Spring Harbor Lab. Press, Cold Spring Harbor, N.Y.
Samowitz et al., 1999, "BAT-26 and BAT-40 instability in colorectal adenomas and carcinomas and germline polymorphisms." Am J Path, 154: 1637-41.
Schwartz et al., 1983, "The "HemoQuant" test: a specific and quantitative determination of heme (hemoglobin) in feces and other materials." Clin Chem, 29: 2061-7.
Schwartz et al., 1985, "Quantitative fecal recovery of ingested hemoglobin-heme in blood: comparisons by HemoQuant assay with ingested meat and fish." Gastroenterology, 89: 19-26.
Singh et al., 2006, "Risk of developing colorectal cancer following a negative colonoscopy examination: evidence for a 10-year interval between colonoscopies." JAMA, 295: 2366-73.
Summons to attend oral proceedings, European patent application No. 11760295.3, dated Mar. 4, 2016.
Tibble, et al. (2001), "Faecal capprotectin and faecal occult blood tests in the diagnosis of colorectal carcinoma and adenoma.," Gut. 49:402-408.

(56) References Cited

OTHER PUBLICATIONS

Uchida, et al. (1994), "Immunochemical detection of human lactoferrin in feces as a new marker for inflammatorygastrointestinal disorders and colon cancer," Clinical Biochemistry. 27(4)L 259-264, abstract only.
Wang, "Gene expression profiles and molecular markers to predict recurrence of duke's B Colon Cancer," vol. 22, p. 1564-1571, 2004.
Wen, et al. (2006), "Frequence epigenetic silencing of the bome morphogenic protein 2 gene through methylation in gastic carcinomas," Onogene. 25:2666-2673.
Winawer et al., 1993, "Screening for colorectal cancer with fecal occult blood testing and sigmoidoscopy." J Natl Cancer Inst, 85: 1311-8.
Wittekind et al. (1986), "Localization of CEA, HCG, lysozyme, alpha-1-antitrypsin, and alpha-1-antichymotrypsin in gastric cancer and prognosis," Virchows Arch 409:715-724.
Young, "Fecal Immunochemical Tests (FIT) vs. Office-based guaiac fecal occult blood test (FOBT)," Practical Gastroenterology, Colorectal Cancer, series 3, p. 46-56, 2004.
Zijlstra et al., 2002, "A quantitative analysis of rate-limiting steps in the metastatic cascade using human-specific real-time polymerase chain reaction." Cancer Res, 62: 7083-92.
Zou et al., 2006, "A sensitive method to quantify human long DNA in stool: relevance to colorectal cancer screening." Cancer Epidemiol Biomarkers Prev, 15: 1115-9.
Zou, et al. (2007), "Highly methylated genes in colorectal neoplasia: Implications for screening," Cancer Epidemilogy Biomarkers Prev. 16(12): 2686-2696.
Zou, et al., "High Detection Rates of Colorectal Neoplasia by Stool DNA Testing with a Novel Digital Melt Curve Assay," Gastroenterology, vol. 136, No. 2, Feb. 1, 2009, pp. 459-470.
Zou, et al., "T2034 Stool DNA and Occult Blood for Detection of Colorectal Cancer: Complementary Markers," Gastroenterology, vol. 136, No. 5, May 1, 2009, p. A-625.
Tan et al. "Variable promoter region CpG island methylation of the putative tumor suppressor gene Connexin 26 in breast cancer" Carcinogenesis. 2002 23(2): 231-236.
Jin et al. "A multicenter, Double-blinded Validation study of methylation biomarkers for progression prediction in Barrett's Esophagus" Cancer Research, May 15, 2009, vol. 69, pp. 4112-4115.
Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.
Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.
International Search Report, International Application No. PCT/US2016/023782, dated Sep. 1, 2016.
Haag S, et al., "Regression of Barrett's esophagus: the role of acid suppression, surgery, and ablative methods." Gastrointest Endosc. Aug 1999;50(2):229-40.
Supplemental Search Report, EP Patent Application No. 15772326.3, dated Oct. 6, 2017.
Kisiel, et al. "Sul340 Detection of Colorectal Cancer and Polyps in Patients with Inflammatory Bowel Disease by Novel Methylated Stool DNA Markers" Gastroenerology, vol. 146, No. 5, May 1, 2014, pp. S-440.
Taylor et al. "109 Discovery of Novel DNA Methylation Markers for the Detection of Colorectal Neopolasia: Selection by Methylome-Wide Analysis" Gastroenterology, vol. 146, No. 5, May 1, 2014, pp. S-30.
Kim et al. Methylation profiles of multiple CpG island loci in extrahepatic cholangiocarcinoma versus those of intrahepatic cholangiocarcinomas. Arch Pathol Lab Med 131:923-930, 2007.
Qiu et al. Hypermethylation of ACP1, BMP4, and TSPYL5 in Hepatocellular Carcinoma and Their Potential Clinical Significance, Digestive Diseases and Sciences, Sep. 19, 2016, vol. 61, No. 1, pp. 149-157.
International Search Report and Written Opinion, International Patent Application No. PCT/US2017/049915, dated Jan. 18, 2018.
Gao et al. "Global Analysis of DNA Methylation in hepatocellular cariconma by a liquid hybridization cpature-based bisulfate sequencing approach" Clinical Epigenetics, vol. 7, No. 86, Aug. 2015.
Barat et al. "Comparative Correlation Structure of Colon Cancer Locus Specific Methylation: Characterisation of Patient Profiles and Potential Markers across 3 Array-Based Datasets" J. of Cancer, vol. 6, pp. 795-811, Jul. 2015.
Sloane et al. "Epigenetic inactivation of the candidate tumor suppressor USP44 is a frequent and early event in colorectal neoplasia" Epigenetics, vol. 9, No. 8, pp. 1092-1100, Aug. 2014.
CN Office Action, CN Patent Application No. 201480015389.5, dated Mar. 30, 2018.

\* cited by examiner

DETECTING NEOPLASM

FIELD OF INVENTION

Provided herein is technology relating to detecting neoplasia and particularly, but not exclusively, to methods, compositions, and related uses for detecting premalignant and malignant neoplasms such as pancreatic and colorectal cancer.

BACKGROUND

In aggregate, gastrointestinal cancers account for more cancer mortality than any other organ system. While colorectal cancers are currently screened, annual US mortality from upper gastrointestinal cancers exceeds 90,000 compared to roughly 50,000 for colorectal cancer. Strikingly, 43,000 men and women are diagnosed each year with pancreatic cancer (PanC), which will cause nearly 37,000 deaths annually (Jemal et al. (2010) "Cancer statistics" *CA Cancer J Clin* 60: 277-300). As a result, PanC is the fourth leading cause of cancer deaths (id). Patients who present with symptoms typically already have advanced stage disease and only 15% meet criteria for potentially curative surgery (Ghaneh et al. (2007) "Biology and management of pancreatic cancer" *Gut* 56: 1134-52). Despite surgery, 85% will die of recurrent disease (Sohn et al. (2000) "Resected adenocarcinoma of the pancreas-616 patients: results, outcomes, and prognostic indicators" *J Gastrointest Surg* 4: 567-79). PanC mortality exceeds 95% and the 5-year survival rate is less than 25% for patients having curative surgery (Cleary et al (2004) "Prognostic factors in resected pancreatic adenocarcinoma: analysis of actual 5-year survivors" *J Am Coll Surg* 198: 722-31; Yeo et al (1995) "Pancreaticoduodenectomy for cancer of the head of the pancreas. 201 patients" *Ann Surg* 221: 721-33).

Among patients with syndromic predisposition to PanC or strong family history, aggressive, invasive screening strategies using computed tomography scans or endoscopic ultrasound have shown a 10% yield for neoplasia (Canto et al. (2006) "Screening for early pancreatic neoplasia in high-risk individuals: a prospective controlled study" *Clin Gastroenterol Hepatol* 4: 766-81). This screening strategy is impractical for the general population where most PanC arises without a known predisposition (Klein et al. (2001) "Familial pancreatic cancer" *Cancer J* 7: 266-73).

The nearly uniform lethality of PanC has generated intense interest in understanding pancreatic tumor biology. Precursor lesions have been identified, including pancreatic intraepithelial neoplasm (PanIN, grades I-III) and intraductal papillary mucinous neoplasm (IPMN) (Fernández-del Castillo et al. (2010) "Intraductal papillary mucinous neoplasms of the pancreas" *Gastroenterology* 139: 708-13, 713.e1-2; Haugk (2010) "Pancreatic intraepithelial neoplasia—can we detect early pancreatic cancer?" *Histopathology* 57: 503-14). Study of both precursors and malignant lesions has identified a number of molecular characteristics at genetic, epigenetic, and proteomic levels that could be exploited for therapy or used as biomarkers for early detection and screening (Kaiser (2008) "Cancer genetics. A detailed genetic portrait of the deadliest human cancers" *Science* 321: 1280-1; Omura et al. (2009) "Epigenetics and epigenetic alterations in pancreatic cancer" *Int J Clin Exp Pathol* 2: 310-26; Tonack et al. (2009) "Pancreatic cancer: proteomic approaches to a challenging disease" *Pancreatology* 9: 567-76). Recent tumor and metastatic lesion mapping studies have shown that there may be a significant latency period between the development of malignant PanC and the development of metastatic disease, suggesting a wide window of opportunity for detection and curative treatment of presymptomatic earliest-stage lesions (Yachida et al. (2010) "Distant metastasis occurs late during the genetic evolution of pancreatic cancer" *Nature* 467: 1114-7).

PanC sheds (e.g., exfoliates) cells and DNA into local effluent and ultimately into stool. For example, DNA containing a mutant KRAS gene can be identified (e.g., sequenced) from pancreatic juice of patients with pancreatic cancer, PanIN, and IPMN (Yamaguchi et al. (2005) "Pancreatic juice cytology in IPMN of the pancreas" *Pancreatology* 5: 416-21). Previously, highly sensitive assays have been used to detect mutant DNA in matched stools of pancreas cancer patients whose excised tumors were known to contain the same sequences (Zou et al (2009) "T2036 Pan-Detection of Gastrointestinal Neoplasms By Stool DNA Testing: Establishment of Feasibility" *Gastroenterology* 136: A-625). A limitation of mutation markers relates to the unwieldy process of their detection in conventional assays; typically, each mutational site across multiple genes must be assayed separately to achieve high sensitivity.

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) "Principles and challenges of genome-wide DNA methylation analysis" *Nat Rev Genet* 11: 191-203). Furthermore, in other cancers like sporadic colon cancer, methylation markers offer excellent specificity and are more broadly informative and sensitive than are individual DNA mutations (Zou et al (2007) "Highly methylated genes in colorectal neoplasia: implications for screening" *Cancer Epidemiol Biomarkers Prev* 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) "DNA methylation analysis of chromosome 21 gene promoters at single base pair and single allele resolution" *PLoS Genet* 5: e1000438). Further, methylation levels were distributed bi-modally between highly methylated and unmethylated sequences, further supporting the binary switch-like pattern of DNA methyltransferase activity (Zhang et al. (2009) "DNA methylation analysis of chromosome 21 gene promoters at single base pair and single allele resolution" *PLoS Genet* 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) "Genome-scale DNA methylation maps of pluripotent and differentiated cells" *Nature* 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) "Genome-scale DNA methylation maps of pluripotent and differentiated cells" *Nature* 454: 766-70).

For pancreatic cancer, PanIN, and IPMN lesions, marker methylation has been studied at the tissue level (Omura et al. (2008) "Genome-wide profiling of methylated promoters in pancreatic adenocarcinoma" *Cancer Biol Ther* 7: 1146-56; Sato et al. (2008) "CpG island methylation profile of pancreatic intraepithelial neoplasia" *Mod Pathol* 21: 238-44; Hong et al. (2008) "Multiple genes are hypermethylated in intraductal papillary mucinous neoplasms of the pancreas" *Mod Pathol* 21: 1499-507). For example, the markers MDFI, ZNF415, CNTNAP2, and ELOVL4 were highly methylated in 96%, 86%, 82%, and 68% of the cancers studied while, comparatively, only 9%, 6%, 3%, and 7% of control (non-cancerous) pancreata, respectively, were highly methylated at these same four loci (Omura et al. (2008) "Genome-wide profiling of methylated promoters in pancreatic adenocarcinoma" *Cancer Biol Ther* 7: 1146-56). It was found that measuring the methylation state of both MDFI and CNTNAP2 provided an indicator for pancreatic cancer that had both a high sensitivity (>90%) and a high specificity (>85%) (Omura et al. (2008) "Genome-wide profiling of methylated promoters in pancreatic adenocarcinoma" *Cancer Biol Ther* 7: 1146-56).

Furthermore, Sato and colleagues found eight genes differentially expressed in pancreatic cancer cell lines before and after treatment with a methyltransferase inhibitor (Sato et al. (2003) "Discovery of novel targets for aberrant methylation in pancreatic carcinoma using high-throughput microarrays" *Cancer Res* 63: 3735-42). These markers were subsequently assessed by methylation-specific PCR (MSP) of DNA from Pan-IN lesions. The results showed that SARP-2 (secreted frizzled related protein 1, SFRP1) had 83% sensitivity and could discriminate between Pan-IN 2 and higher grade Pan-IN 3 (Sato et al. (2008) "CpG island methylation profile of pancreatic intraepithelial neoplasia" *Mod Pathol* 21: 238-44). Discrimination of a high grade precursor or early stage cancer from a lower grade lesion is important when considering the morbidity of pancreaticoduodenectomy or distal pancreatectomy, the main surgical therapies for PanC. When studying both main-duct and side-branch IPMN precursors, Hong and colleagues showed high sensitivity and specificity for SFRP1 as well, especially in combination with UCHL1 (Hong et al. (2008) "Multiple genes are hypermethylated in intraductal papillary mucinous neoplasms of the pancreas" *Mod Pathol* 21: 1499-507). Tissue factor pathway inhibitor 2 (TFPI2) has a well-established tumor suppressor role in GU and GI malignancies, including prostate, cervical, colorectal, gastric, esophageal, and pancreatic cancers (Ma et al. (2011) "MicroRNA-616 induces androgen-independent growth of prostate cancer cells by suppressing expression of tissue factor pathway inhibitor TFPI-2" *Cancer Res* 71: 583-92; Lim et al. (2010) "Cervical dysplasia: assessing methylation status (Methylight) of CCNA1, DAPK1, HS3ST2, PAX1 and TFPI2 to improve diagnostic accuracy" *Gynecol Oncol* 119: 225-31; Hibi et al. (2010) "Methylation of TFPI2 gene is frequently detected in advanced well-differentiated colorectal cancer" *Anticancer Res* 30: 1205-7; Glockner et al. (2009) "Methylation of TFPI2 in stool DNA: a potential novel biomarker for the detection of colorectal cancer" *Cancer Res* 69: 4691-9; Hibi et al. (2010) "Methylation of the TFPI2 gene is frequently detected in advanced gastric carcinoma" *Anticancer Res* 30: 4131-3; Tsunoda et al. (2009) "Methylation of CLDN6, FBN2, RBP1, RBP4, TFPI2, and TMEFF2 in esophageal squamous cell carcinoma" *Oncol Rep* 21: 1067-73; Tang et al. (2010) "Prognostic significance of tissue factor pathway inhibitor-2 in pancreatic carcinoma and its effect on tumor invasion and metastasis" *Med Oncol* 27: 867-75; Brune et al. (2008) "Genetic and epigenetic alterations of familial pancreatic cancers" *Cancer Epidemiol Biomarkers Prev* 17: 3536-4). This marker has also been shown to be shed into the GI lumen and was 73% sensitive when assayed from pancreatic juice of cancers and normal subjects (Matsubayashi et al. (2006) "DNA methylation alterations in the pancreatic juice of patients with suspected pancreatic disease" *Cancer Res* 66: 1208-17).

TFPI2 was among a large number of potential mutation and methylation markers studied in tissue and stool samples as candidates for colorectal neoplasia. In a training-test set analysis of archival stools from almost 700 subjects, a multi-marker methylation panel, including TFPI2, BMP3, NDRG4, and vimentin was shown to have 85% sensitivity in CRC and 64% sensitivity in advanced colorectal adenomas, both at 90% specificity (Ahlquist D et al. (2010) "Next Generation Stool DNA Testing for Detection of Colorectal Neoplasia—Early Marker Evaluation", presented at *Colorectal Cancer: Biology to Therapy*, American Association for Cancer Research).

Previous research has tested the performance of colorectal cancer methylation markers in PanC detection. In particular, a case-control study compared DNA from PanC tumor cases to DNA from colonic epithelia using MSP targeting markers previously reported in PanC (e.g., MDFI, SFRP2, UCHL1, CNTNAP2, and TFPI2) and additional discriminant colonic neoplasm markers (e.g., BMP3, EYA4, Vimentin, and NDRG4). A multi-marker regression model showed that EYA4, UCHL1, and MDFI were highly discriminant, with an area under the receiver operating characteristics curve of 0.85. As an individual marker, BMP3 was found to have an area under the receiver operator characteristics curve of 0.90. These four markers and mutant KRAS were subsequently assayed in a larger set of stool samples from PanC subjects in a blinded comparison to matched stools from individuals with a normal colonoscopy. Individually, BMP3 and KRAS were highly specific but poorly sensitive; in combination, sensitivity improved to 65% while maintaining 88% specificity (Kisiel, et al. (2011) "Stool DNA screening for colorectal cancer: opportunities to improve value with next generation tests" *J Clin Gastroenterol* 45: 301-8. These results suggested that methylation differences in UCHL1, EYA4, and MDFI at the level of the pancreas were obscured by background colonic methylation in the stool-based comparison. As such, cancer screening is in need of a marker or marker panel for PanC that is broadly informative and exhibits high specificity for PanC at the tissue level when interrogated in samples taken from a subject (e.g., a stool sample).

SUMMARY

Accordingly, provided herein is technology for pancreatic cancer screening markers and other gastrointestinal cancer screening markers that provide a high signal-to-noise ratio and a low background level when detected from samples taken from a subject (e.g., stool sample). Markers were identified in a case-control study by comparing the methylation state of DNA markers from tumors of subjects with stage I and stage II PanC to the methylation state of the same DNA markers from control subjects (e.g., normal tissue such as normal colon and/or non-neoplastic pancreas) (see, Examples 1 and 11).

Markers and/or panels of markers (e.g., a chromosomal region having an annotation selected from ABCB1, ADCY1, BHLHE23 (LOC63930), c13orf18, CACNA1C, chr12 133, CLEC11A, ELMO1, EOMES, CLEC 11, SHH, GJC1, IHIF1, IKZF1, KCNK12, KCNN2, PCBP3, PRKCB, RSPO3, SCARF2, SLC38A3, ST8SIA1, TWIST1, VWC2, WT1, and ZNF71) were identified in a case-control study by comparing the methylation state of DNA markers (e.g., from tumors of subjects with stage I and stage II PanC to the methylation state of the same DNA markers from control subjects (e.g., normal tissue such as normal colon and/or non-neoplastic pancreas) (see, Examples 2 and 8).

Markers and/or panels of markers (e.g., a chromosomal region having an annotation selected from NDRG4, SFRP1, BMP3, HPP1, and/or APC) were identified in case-control studies by comparing the methylation state of DNA markers from esophageal tissue of subjects with Barrett's esophagus to the methylation state of the same DNA markers from control subjects (see, Examples 4 and 10).

Markers and/or panels of markers (e.g., a chromosomal region having an annotation selected from ADCY1, PRKCB, KCNK12, C13ORF18, IKZF1, TWIST1, ELMO, 55957, CD1D, CLEC11A, KCNN2, BMP3, and/or NDRG4) were identified in case-control studies by comparing the methylation state of DNA markers from a pancreatic juice sample from subjects with pancreas cancer to the methylation state of the same DNA markers from control subjects (see, Examples 5 and 6).

A marker (e.g., a chromosomal region having a CD1D annotation) was identified in a case-control study by comparing the methylation state of a DNA marker (e.g., CD1D) from a stool sample from subjects with pancreas cancer to the methylation state of the same DNA marker from control subjects not having pancreas cancer (see, Example 7).

A marker (e.g., miR-1290) was identified in a case-control study by comparing the quantitated amount of a DNA marker (e.g., miR-1290) from a stool sample from subjects with pancreas cancer to the quantitated amount of the same DNA marker from control subjects not having pancreas cancer (see, Example 9).

Additional statistical analysis of the results demonstrated that the technology described herein based on these markers specifically and sensitively predicts a tumor site.

As described herein, the technology provides a number of methylated DNA markers and subsets thereof (e.g., sets of 2, 3, 4, 5, 6, 7, 8, 9, 10, 11, 12 or more markers) with high discrimination for GI neoplasms overall and/or at individual tumor sites. Experiments applied a selection filter to candidate markers to identify markers that provide a high signal to noise ratio and a low background level to provide high specificity, e.g., when assaying distant media (e.g., stool, blood, urine, metastatic tissue, etc.) for purposes of cancer screening or diagnosis. Further, experiments were performed to demonstrate that the identified methylated DNA markers predict tumor site. As such, the technology provides for specific markers, marker combinations, and algorithms to predict tumor site.

In some embodiments, the technology is related to assessing the presence of and methylation state of one or more of the markers identified herein in a biological sample. These markers comprise one or more differentially methylated regions (DMR) as discussed herein, e.g., as provided in Table 1 and/or Table 10. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) *Mol. Cell. Biol.* 14: 7421-7427) and another example involves methylation-sensitive arbitrarily primed PCR (Gonzalgo et al. (1997) *Cancer Res.* 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) *Nucl. Acids Res.* 18: 687). In addition, other techniques have been reported that utilize bisulfite treatment of DNA as a starting point for methylation analysis. These include methylation-specific PCR (MSP) (Herman et al. (1992) *Proc. Natl. Acad. Sci. USA* 93: 9821-9826) and restriction enzyme digestion of PCR products amplified from bisulfite-converted DNA (Sadri and Hornsby (1996) *Nucl. Acids Res.* 24: 5058-5059; and Xiong and Laird (1997) *Nucl. Acids Res.* 25: 2532-2534). PCR techniques have been developed for detection of gene mutations (Kuppuswamy et al. (1991) *Proc. Natl. Acad. Sci. USA* 88: 1143-1147) and quantification of allelic-specific expression (Szabo and Mann (1995) *Genes Dev.* 9: 3097-3108; and Singer-Sam et al. (1992) *PCR Methods Appl.* 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106, incorporated herein by reference).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-107 as provided in Table 1, e.g., DMR 1-449 in Table 10); comparing methylation states (e.g., of one or more DMR, e.g., DMR 1-107 as provided in Table 1, e.g., DMR 1-449 in Table 10); generating standard curves; determining a Ct value; calculating a fraction, frequency, or percentage of methylation (e.g., of one or more DMR, e.g., DMR 1-107 as provided in Table 1, e.g., DMR 1-449 in Table 10); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Table 1, e.g., as provided in Table 10). Related embodiments calculate a risk factor based on a mathematical combination (e.g., a weighted combination, a linear combination) of the results from multiple assays, e.g., determining the methylation states of multiple markers (such as multiple DMR, e.g., as provided in Table 1, e.g., as provided in Table 10). In some embodiments, the methylation state of a DMR defines a dimension and may have values in a multidimensional space and the coordinate defined by the methylation states of multiple DMR is a result, e.g., to report to a user, e.g., related to a cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for a neoplasm in a sample obtained from a subject, the method comprising assaying a methylation state of a marker in a sample obtained from a subject; and identifying the subject as having a neoplasm when the methylation state of the marker is different than a methylation state of the marker assayed in a subject that does not have a neoplasm, wherein the marker comprises a base in a differentially methylated region (DMR) selected from a group consisting of DMR 1-107 as provided in Table 1 and/or DMR 1-449 in Table 10. In some embodiments, the method further comprises locating the neoplasm site within the subject, wherein the methylation state of the marker indicates the neoplasm site within the subject. The technology is related to identifying and discriminating gastrointestinal cancers, e.g., in some embodiments the neoplasm is a gastrointestinal neoplasm. In some embodiments, the neoplasm is present in the upper gastrointestinal area of the patient and in some embodiments the neoplasm is present in the lower gastrointestinal area of the patient. In particular embodiments, the neoplasm is a pancreas neoplasm, a colorectal neoplasm, a bile duct neoplasm, or an adenoma. The technology also encompasses determining the state or stage of a cancer, e.g., in some embodiments the neoplasm is pre-cancerous. Some embodiments provide methods comprising assaying a plurality of markers, e.g., comprising assaying 2 to 11 markers.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample, a pancreatic juice sample, a pancreatic cyst fluid sample, a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-202. In some embodiments are provided an oligonucleotide comprising a sequence complementary to a chromosomal region having a base in a DMR, e.g., an oligonucleotide sensitive to methylation state of a DMR.

The technology provides various panels of markers, e.g., in some embodiments the marker comprises a chromosomal region having an annotation that is ABCB1, ADCY1, BHLHE23 (LOC63930), c13orf18, CACNA1C, chr12.133, CLEC11A, ELMO1, EOMES, GJC1, IHIF1, IKZF1, KCNK12, KCNN2, NDRG4, PCBP3, PRKCB, RSPO3, SCARF2, SLC38A3, ST8SIA1, TWIST1, VWC2, WT1, or ZNF71, and that comprises the marker (see, Tables 1 and 9). In addition, embodiments provide a method of analyzing a DMR from Table 1 that is DMR No. 11, 14, 15, 65, 21, 22, 23, 5, 29, 30, 38, 39, 41, 50, 51, 55, 57, 60, 61, 8, 75, 81, 82, 84, 87, 93, 94, 98, 99, 103, 104, or 107, and/or a DMR corresponding to Chr16:58497395-58497458. Some embodiments provide determining the methylation state of a marker, wherein a chromosomal region having an annotation that is CLEC11A, C13ORF18, KCNN2, ABCB1, SLC38A3, CD1D, IKZF1, ADCY1, CHR12133, RSPO3, MBP3, PRKCB, NDRG4, ELMO, or TWIST1 comprises the marker. In some embodiments, the methods comprise determining the methylation state of two markers, e.g., a pair of markers provided in a row of Table 5.

Kit embodiments are provided, e.g., a kit comprising a bisulfite reagent; and a control nucleic acid comprising a sequence from a DMR selected from a group consisting of DMR 1-107 (from Table 1) and/or a DMR selected from a group consisting of DMR 1-449 (from Table 10) and having a methylation state associated with a subject who does not have a cancer. In some embodiments, kits comprise a bisulfite reagent and an oligonucleotide as described herein. In some embodiments, kits comprise a bisulfite reagent; and a control nucleic acid comprising a sequence from a DMR selected from a group consisting of DMR 1-107 (from Table 1) and/or DMR 1-449 (from Table 10) and having a methylation state associated with a subject who has a cancer. Some kit embodiments comprise a sample collector for obtaining a sample from a subject (e.g., a stool sample); reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a DMR and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for a neoplasm in a sample obtained from a subject, e.g., a method comprising determining a methylation state of a marker in the sample comprising a base in a DMR that is one or more of DMR 1-107 (from Table 1) and/or one or more of DMR 1-449 (from Table 10); comparing the methylation state of the marker from the subject sample to a methylation state of the marker from a normal control sample from a subject who does not have a cancer; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the DMR from a subject who does not have a cancer to identify differences in the two sequences; and identifying the subject as having a neoplasm when a difference is present.

Systems for screening for a neoplasm in a sample obtained from a subject are provided by the technology. Exemplary embodiments of systems include, e.g., a system for screening for a neoplasm in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a cancer-associated methylation state. An alert is determined in some embodiments by a software component that receives the results from multiple assays (e.g., determining the methylation states of multiple markers, e.g., DMR, e.g., as provided in Table 1, e.g., as provided in Table 10) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a cancer risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have a cancer. Also provided are nucleic acids, e.g., a set of nucleic acids, each nucleic acid having a sequence comprising a DMR. In some embodiments the set of nucleic acids wherein each nucleic acid has a sequence from a subject who does not have a cancer. Related system embodiments comprise a set of nucleic acids as described and a database of nucleic acid sequences associated with the set of nucleic acids. Some embodiments further comprise a bisulfite reagent. And, some embodiments further comprise a nucleic acid sequencer.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1:
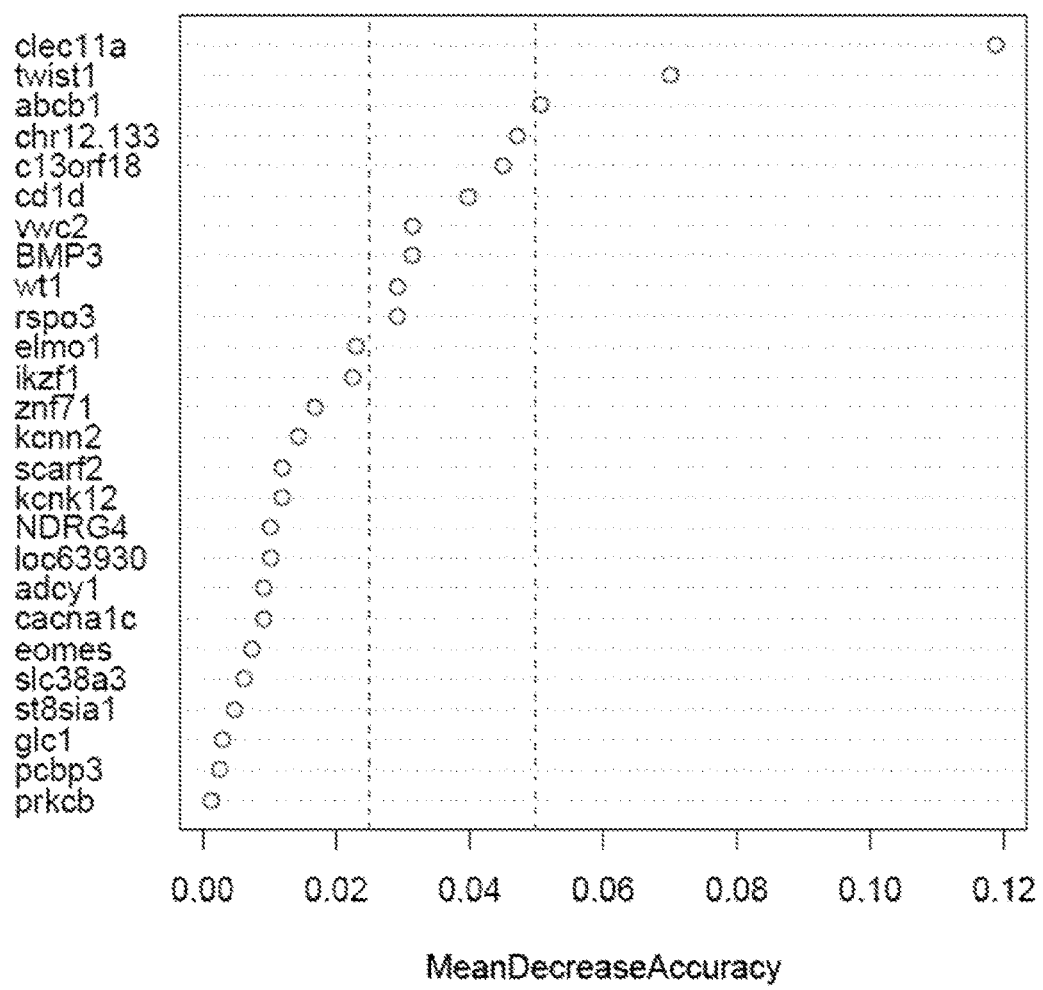
FIG. 1 is a plot showing the marker importance of a subset of methylation markers as measured by Mean Decrease in Accuracy for Site Prediction.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, compositions, and methods disclosed herein. Wherever possible, the same reference numbers are used throughout the drawings to refer to the same or like parts. Moreover, it should be appreciated that the drawings are not intended to limit the scope of the present teachings in any way.

DETAILED DESCRIPTION

Provided herein is technology relating to detecting neoplasia and particularly, but not exclusively, to methods, compositions, and related uses for detecting premalignant and malignant neoplasms such as pancreatic and colorectal cancer. As the technology is described herein, the section headings used are for organizational purposes only and are not to be construed as limiting the subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), Hot-start PCR (see, e.g., U.S. Pat. Nos. 5,773,258 and 5,338,671; each herein incorporated by reference in their entireties), intersequence-specific PCR, inverse PCR (see, e.g., Triglia, et al. et al. (1988) Nucleic Acids Res., 16:8186; herein incorporated by reference in its entirety), ligation-mediated PCR (see, e.g., Guilfoyle, R. et al. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al. et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependant DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barnay Proc. Natl. Acad. Sci USA 88, 189-93 (1991)); and sandwich hybridization methods (e.g., U.S. Pat. No. 5,288,609, herein incorporated by reference in its entirety).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J. Mol. Biol. 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) *Proc. Natl. Acad. Sci. USA* 97: 5237-5242; Salmon and Kaye (1970) *Biochim. Biophys. Acta.* 204: 340-351; Grafstrom (1985) *Nucleic Acids Res.* 13: 2827-2842; Nyce (1986) *Nucleic Acids Res.* 14: 4353-4367; Woodcock (1987) *Biochem. Biophys. Res. Commun.* 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) *Cancer Research* 57: 594-599.

The term "MethyLight™" refers to the art-recognized fluorescence-based real-time PCR technique described by Eads et al. (1999) *Cancer Res.* 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) *Nucleic Acids Res.* 25: 2529-2531.

The term "MSP" (Methylation-specific PCR) refers to the art-recognized methylation assay described by Herman et al. (1996) *Proc. Natl. Acad. Sci. USA* 93: 9821-9826, and by U.S. Pat. No. 5,786,146.

The term "COBRA" (Combined Bisulfite Restriction Analysis) refers to the art-recognized methylation assay described by Xiong & Laird (1997) *Nucleic Acids Res.* 25: 2532-2534.

The term "MCA" (Methylated CpG Island Amplification) refers to the methylation assay described by Toyota et al. (1999) *Cancer Res.* 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemimethylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) *Signal Detection Theory and ROC Analysis*, Academic Press, New York).

As used herein, the term "neoplasm" refers to "an abnormal mass of tissue, the growth of which exceeds and is uncoordinated with that of the normal tissues" See, e.g., Willis R A, "The Spread of Tumors in the Human Body", London, Butterworth & Co, 1952.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "marker", as used herein, refers to a substance (e.g., a nucleic acid or a region of a nucleic acid) that is able to diagnose a cancer by distinguishing cancerous cells from normal cells, e.g., based its methylation state.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from a pancreas), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Embodiments of the Technology

Provided herein is technology for pancreatic cancer screening markers and other gastrointestinal cancer screening markers that provide a high signal-to-noise ratio and a low background level when detected from samples taken from a subject (e.g., stool sample). Markers were identified in a case-control study by comparing the methylation state of DNA markers from tumors of subjects with stage I and stage II PanC to the methylation state of the same DNA markers from control subjects (e.g., normal tissue such as normal colon and/or non-neoplastic pancreas) (see, Examples 1 and 11). Markers and/or panels of markers (e.g., a chromosomal region having an annotation selected from ABCB1, ADCY1, BHLHE23 (LOC63930), c13orf18, CACNA1C, chr12 133, CLEC11A, ELMO1, EOMES, CLEC 11, SHH, GJC1, IHIF1, IKZF1, KCNK12, KCNN2, PCBP3, PRKCB, RSPO3, SCARF2, SLC38A3, ST8SIA1, TWIST1, VWC2, WT1, and ZNF71) were identified in a case-control study by comparing the methylation state of DNA markers (e.g., from tumors of subjects with stage I and stage II PanC to the methylation state of the same DNA markers from control subjects (e.g., normal tissue such as normal colon and/or non-neoplastic pancreas) (see, Examples 2 and 8).

Markers and/or panels of markers (e.g., a chromosomal region having an annotation selected from NDRG4, SFRP1, BMP3, HPP1, and/or APC) were identified in case-control studies by comparing the methylation state of DNA markers from esophageal tissue of subjects with Barrett's esophagus to the methylation state of the same DNA markers from control subjects (see, Examples 4 and 10).

Markers and/or panels of markers (e.g., a chromosomal region having an annotation selected from ADCY1, PRKCB, KCNK12, C13ORF18, IKZF1, TWIST1, ELMO, 55957, CD1D, CLEC11A, KCNN2, BMP3, and/or NDRG4) were identified in case-control studies by comparing the methylation state of DNA markers from a pancreatic juice sample from subjects with pancreas cancer to the methylation state of the same DNA markers from control subjects (see, Examples 5 and 6).

A marker (e.g., a chromosomal region having a CD1D annotation) was identified in a case-control study by comparing the methylation state of a DNA marker (e.g., CD1D) from a stool sample from subjects with pancreas cancer to the methylation state of the same DNA marker from control subjects not having pancreas cancer (see, Example 7).

A marker (e.g., miR-1290) was identified in a case-control study by comparing the quantitated amount of a DNA marker (e.g., miR-1290) from a stool sample from subjects with pancreas cancer to the quantitated amount of the same DNA marker from control subjects not having pancreas cancer (see, Example 9).

In addition, the technology provides various panels of markers, e.g., in some embodiments the marker comprises a chromosomal region having an annotation that is ABCB1, ADCY1, BHLHE23 (LOC63930), c13orf18, CACNA1C, chr12.133, CLEC11A, ELMO1, EOMES, GJC1, IHIF1, IKZF1, KCNK12, KCNN2, NDRG4, PCBP3, PRKCB, RSPO3, SCARF2, SLC38A3, ST8SIA1, TWIST1, VWC2, WT1, or ZNF71, and that comprises the marker (see, Tables 1 and 9). In addition, embodiments provide a method of analyzing a DMR from Table 1 that is DMR No. 11, 14, 15, 65, 21, 22, 23, 5, 29, 30, 38, 39, 41, 50, 51, 55, 57, 60, 61, 8, 75, 81, 82, 84, 87, 93, 94, 98, 99, 103, 104, or 107, and/or a DMR corresponding to Chr16:58497395-58497458. Some embodiments provide determining the methylation state of a marker, wherein a chromosomal region having an annotation that is CLEC11A, C13ORF18, KCNN2, ABCB1, SLC38A3, CD1D, IKZF1, ADCY1, CHR12133, RSPO3, MBP3, PRKCB, NDRG4, ELMO, or TWIST' comprises the marker. In some embodiments, the methods comprise determining the methylation state of two markers, e.g., a pair of markers provided in a row of Table 5.

Although the disclosure herein refers to certain illustrated embodiments, it is to be understood that these embodiments are presented by way of example and not by way of limitation.

In particular aspects, the present technology provides compositions and methods for identifying, determining, and/or classifying a cancer such as an upper gastrointestinal cancer (e.g., cancer of the esophagus, pancreas, stomach) or lower gastrointestinal cancer (e.g., adenoma, colorectal cancer). In related aspects, the technology provides compositions and methods for identifying, predicting, and/or detecting the site of a cancer. The methods comprise determining the methylation status of at least one methylation marker in a biological sample isolated from a subject, wherein a change in the methylation state of the marker is indicative of the presence, class, or site of a cancer. Particular embodiments relate to markers comprising a differentially methylated region (DMR, e.g., DMR 1-107, see Table 1, e.g., DMR 1-449, see Table 10) that are used for diagnosis (e.g., screening) of neoplastic cellular proliferative disorders (e.g., cancer), including early detection during the pre-cancerous stages of disease and prediction of a neoplasm site (e.g., by discriminating among cancer types, e.g., upper gastrointestinal cancers and lower gastrointestinal cancers). Furthermore, the markers are used for the differentiation of neoplastic from benign cellular proliferative disorders. In particular aspects, the present technology discloses a method wherein a neoplastic cell proliferative disorder is distinguished from a benign cell proliferative disorder.

The markers of the present technology are particularly efficient in detecting or distinguishing between colorectal and pancreatic proliferative disorders, thereby providing improved means for the early detection, classification, and treatment of said disorders.

In addition to embodiments wherein the methylation analysis of at least one marker, a region of a marker, or a base of a marker comprising a DMR (e.g., DMR 1-107 from Table 1) (e.g., DMR 1-449 from Table 10) provided herein and listed in Table 1 or 10 is analyzed, the technology also provides panels of markers comprising at least one marker, region of a marker, or base of a marker comprising a DMR with utility for the detection of cancers, in particular colorectal, pancreatic cancer, and other upper and lower GI cancers.

Some embodiments of the technology are based upon the analysis of the CpG methylation status of at least one marker, region of a marker, or base of a marker comprising a DMR.

In some embodiments, the present technology provides for the use of the bisulfite technique in combination with one or more methylation assays to determine the methylation status of CpG dinucleotide sequences within at least one marker comprising a DMR (e.g., as provided in Table 1 (e.g., DMR 1-107)) (e.g., as provided in Table 10 (e.g., DMR 1-449)). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of cancers such as upper gastrointestinal cancer (e.g., cancer of the esophagus, pancreas, stomach) or lower gastrointestinal cancer (e.g., adenoma, colorectal cancer).

Combinations of Markers

In some embodiments, the technology relates to assessing the methylation state of combinations of markers comprising a DMR from Table 1 (e.g., 2, 3, 4, 5, 6, 7, 8, 9, 10, 11, 12, 13, 14, 15, 16, 17, 18, 19, 20, 21, 22, 23, 24, 25, 26, 27, 27, 29, 30) or Table 10 (e.g., 2, 3, 4, 5, 6, 7, 8, 9, 10, 11, 12, 13, 14, 15, 16, 17, 18, 19, 20, 21, 22, 23, 24, 25, 26, 27, 27, 29, 30), or more markers comprising a DMR. In some embodiments, assessing the methylation state of more than one marker increases the specificity and/or sensitivity of a screen or diagnostic for identifying a neoplasm in a subject, e.g., an upper gastrointestinal cancer (e.g., esophagus, pancreas, stomach) or a lower gastrointestinal cancer (e.g., adenoma, colorectal). In some embodiments, a marker or a combination of markers discriminates between types and/or locations of a neoplasm. For example, combinations of markers discriminate esophageal neoplasm, stomach neoplasm, pancreatic neoplasm, colorectal neoplasm, and adenomas from each other, from other neoplasms, and/or from normal (e.g., non-cancerous, non-precancerous) tissue.

Various cancers are predicted by various combinations of markers, e.g., as identified by statistical techniques related to specificity and sensitivity of prediction. The technology provides methods for identifying predictive combinations and validated predictive combinations for some cancers.

In some embodiments, combinations of markers (e.g., comprising a DMR) predict the site of a neoplasm. For example, during the development of the technology described herein, statistical analyses were performed to validate the sensitivity and specificity of marker combinations. For example, marker pairs accurately predicted tumor site in >90% of samples, the top 17 marker pairs accurately predicted tumor site in >80% of samples, and the top 49 marker pairs accurately predicted tumor site in 70% of the samples.

Methods for Assaying Methylation State

The most frequently used method for analyzing a nucleic acid for the presence of 5-methylcytosine is based upon the bisulfite method described by Frommer, et al. for the detection of 5-methylcytosines in DNA (Frommer et al. (1992) *Proc. Natl. Acad. Sci. USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uricil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994)

16: 431-36; Grigg G, DNA Seq. (1996) 6: 189-98) or methylation-specific PCR (MSP) as is disclosed, e.g., in U.S. Pat. No. 5,786,146.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) Nucleic Acids Res. 26: 2255.

The bisulfite technique typically involves amplifying short, specific fragments of a known nucleic acid subsequent to a bisulfite treatment, then either assaying the product by sequencing (Olek & Walter (1997) Nat. Genet. 17: 275-6) or a primer extension reaction (Gonzalgo & Jones (1997) Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6; Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can by used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, DMR, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" *Nat Methods* 7: 133-6; Meissner et al. (2005) "Reduced representation bisulfite sequencing for comparative high-resolution DNA methylation analysis" *Nucleic Acids Res.* 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes cleavase to release the flap sequence by cutting between the detection probe and the flap sequence. The flap sequence is complementary to a nonhairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" *Clin Chem* 56: A199; U.S. patent application Ser. Nos. 12/946,737, 12/946,745, 12/946,752, and 61/548,639.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715, which is incorporated by reference in its entirety). It is preferred that the bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). The bisulfite conversion is preferably carried out at a reaction temperature between 30° C. and 70° C., whereby the temperature is increased to over 85° C. for short times during the reaction (see: PCT/EP2004/011715, which is incorporated by reference in its entirety). The bisulfite treated DNA is preferably purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715, which is incorporated by reference in its entirety).

In some embodiments, fragments of the treated DNA are amplified using sets of primer oligonucleotides according to the present invention (e.g., see Table 2) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-107 as provided in Table 1) (e.g., DMR 1-449 as provided in Table 10) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

Methods

In some embodiments the technology, methods are provided that comprise the following steps:

1) contacting a nucleic acid (e.g., genomic DNA, e.g., isolated from a body fluids such as a stool sample or pancreatic tissue) obtained from the subject with at least one reagent or series of reagents that distinguishes between methylated and non-methylated CpG dinucleotides within at least one marker comprising a DMR (e.g., DMR 1-107, e.g., as provided in Table 1) (e.g., DMR 1-449, e.g., as provided in Table 10) and 2) detecting a neoplasm or proliferative disorder (e.g., afforded with a sensitivity of greater than or equal to 80% and a specificity of greater than or equal to 80%).

In some embodiments the technology, methods are provided that comprise the following steps:

1) contacting a nucleic acid (e.g., genomic DNA, e.g., isolated from a body fluids such as a stool sample or pancreatic tissue) obtained from the subject with at least one reagent or series of reagents that distinguishes between methylated and non-methylated CpG dinucleotides within at least one marker selected from a chromosomal region having an annotation selected from the group consisting of ABCB1, ADCY1, BHLHE23 (LOC63930), c13orf18, CACNA1C, chr12 133, CLEC11A, ELMO1, EOMES, CLEC 11, SHH, GJC1, IHIF1, IKZF1, KCNK12, KCNN2, PCBP3, PRKCB, RSPO3, SCARF2, SLC38A3, ST8SIA1, TWIST1, VWC2, WT1, and ZNF71, and
2) detecting pancreatic cancer (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample or esophageal tissue) obtained from the subject with at least one reagent or series of reagents that distinguishes between methylated and non-methylated CpG dinucleotides within at least one marker selected from a chromosomal region having an annotation selected from the group consisting of NDRG4, SFRP1, BMP3, HPP1, and APC, and
2) detecting Barrett's esophagus (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample or pancreatic tissue) obtained from the subject with at least one reagent or series of reagents that distinguishes between methylated and non-methylated CpG dinucleotides within at least one marker selected from a chromosomal region having an annotation selected from the group consisting of ADCY1, PRKCB, KCNK12, C13ORF18, IKZF1, TWIST1, ELMO, 55957, CD1D, CLEC11A, KCNN2, BMP3, and NDRG4, and
2) detecting pancreatic cancer (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a stool sample) obtained from the subject with at least one reagent or series of reagents that distinguishes between methylated and non-methylated CpG dinucleotides within a chromosomal region having a CD1D, and
2) detecting pancreatic cancer (e.g., afforded with a sensitivity of greater than or equal to 80% and a specificity of greater than or equal to 80%).

Preferably, the sensitivity is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-107, e.g., as provided by Table 1) (e.g., DMR 1-449, e.g., as provided by Table 10).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed byt alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-107, e.g., as provided in Table 1) (at least one gene, genomic sequence, or nucleotide from a marker comprising a DMR, e.g., at least one DMR chosen from DMR 1-449, e.g., as provided in Table 10). The method of analysis may be selected from those known in the art, including those listed herein, e.g., QuARTS and MSP as described herein.

Aberrant methylation, more specifically hypermethylation of a marker comprising a DMR (e.g., DMR 1-107, e.g., as provided by Table 1) (e.g., DMR 1-449, e.g., as provided by Table 10) is associated with a cancer and, in some embodiments, predicts tumor site.

The technology relates to the analysis of any sample associated with a cancer of the gastrointestinal system. For example, in some embodiments the sample comprises a tissue and/or biological fluid obtained from a patient. In some embodiments, the sample comprises a secretion. In some embodiments, the sample comprises blood, serum, plasma, gastric secretions, pancreatic juice, a gastrointestinal biopsy sample, microdissected cells from a gastrointestinal biopsy, gastrointestinal cells sloughed into the gastrointestinal lumen, and/or gastrointestinal cells recovered from stool. In some embodiments, the subject is human. These samples may originate from the upper gastrointestinal tract, the lower gastrointestinal tract, or comprise cells, tissues, and/or secretions from both the upper gastrointestinal tract and the lower gastrointestinal tract. The sample may include cells, secretions, or tissues from the liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens.

In some embodiments, the technology relates to a method for treating a patient (e.g., a patient with gastrointestinal cancer, with early stage gastrointestinal cancer, or who may develop gastrointestinal cancer), the method comprising determining the methylation state of one or more DMR as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing a gastrointestinal cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of gastrointestinal cancer, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with gastrointestinal cancer risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome (e.g., suffering from a gastrointestinal cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biamarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with a gastrointestinal cancer. In certain embodiments of the method, a subject is identified as having metaplasia upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having a gastrointestinal cancer if, when compared to a control methylation state, there is a measurable difference in the methylation state of at least one biomarker in the sample. Conversely, when no change in methylation state is identified in the biological sample, the subject can be identified as not having gastrointestinal cancer, not being at risk for the cancer, or as having a low risk of the cancer. In this regard, subjects having the cancer or risk thereof can be differentiated from subjects having low to substantially no cancer or risk thereof. Those subjects having a risk of developing a gastrointestinal cancer can be placed on a more intensive and/or regular screening schedule, including endoscopic surveillance. On the other hand, those subjects having low to substantially no risk may avoid being subjected to an endoscopy, until such time as a future screening, for example, a screening conducted in accordance with the present technology, indicates that a risk of gastrointestinal cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, a gastrointestinal cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like. The presently-disclosed subject matter further includes a system for diagnosing a gastrointestinal cancer in a subject. The system can be provided, for example, as a commercial kit that can be used to screen for a risk of gastrointestinal cancer or diagnose a gastrointestinal cancer in a subject from whom a biological sample has been collected. An exemplary system provided in accordance with the present technology includes assessing the methylation state of a DMR as provided in Table 1.

EXAMPLES

Example 1—Identifying Markers Using RRBS

Collectively, gastrointestinal cancers account for more deaths than those from any other organ system, and the aggregate incidence of upper gastrointestinal cancer and that of colorectal cancer (CRC) are comparable. To maximize the efficiency of screening and diagnosis, molecular markers for gastrointestinal cancer are needed that are site-specific when assayed from distant media such as blood or stool. While broadly informative, aberrantly methylated nucleic acid markers are often common to upper gastrointestinal cancers and CRC.

During the development of the technology provided herein, data were collected from a case-control study to demonstrate that a genome-wide search strategy identifies novel and informative candidate markers. Preliminary experiments demonstrated that stool assay of a methylated gene marker (BMP3) detects PanC. Then, it was shown that a combined assay of methylated BMP3 and mutant KRAS increased detection over either marker alone. However, markers discriminant in tissue proved to be poor markers in stool due to a high background of methylation, e.g., as detected in control specimens.

Study Population, Specimen Acquisition, and Samples

The target population was patients with pancreas cancer seen at the Mayo Clinic. The accessible population includes those who have undergone a distal pancreatectomy, a pancreaticoduodenectomy, or a colectomy with an archived resection specimen and a confirmed pathologic diagnosis. Colonic epithelial DNA was previously extracted from micro-dissected specimens by the Biospecimens Accessioning Processing (BAP) lab using a phenol-chloroform protocol. Data on the matching variables for these samples were used by Pancreas SPORE personnel to select tissue registry samples. These were reviewed by an expert pathologist to confirm case and control status and exclude case neoplasms arising from IPMN, which may have different underlying biology. SPORE personnel arranged for BAP lab microdissection and DNA extraction of the pancreatic case and control samples and provided 500 ng of DNA to lab personnel who were blinded to case and control status. Archival nucleic acid samples included 18 pancreatic adenocarcinomas, 18 normal pancreas, and 18 normal colonic epithelia matched on sex, age, and smoking status.

The sample types were:
1) Mayo Clinic Pancreas SPORE registry PanC tissues limited to AJCC stage I and II:
2) control pancreata free from PanC;
3) archived control colonic epithelium free from PanC; and
4) colonic neoplasm from which DNA had been extracted and stored in the BAP lab.

Cases and controls were matched by sex, age (in 5-year increments), and smoking status (current or former vs. never).

Main Variables

The main variable was the methylation percentage of each individual 101 base-pair amplicon from HCP regions. The methylation percentage in case samples was compared to control samples following RRBS.

Methods

Libraries were prepared according to previously reported methods (see, e.g., Gu et al (2011) "Preparation of reduced representation bisulfite sequencing libraries for genome-scale DNA methylation profiling" Nature Protocols 6: 468-81) by fragmenting genomic DNA (300 ng) by digestion with 10 units of MspI, a methylation-specific restriction enzyme that recognizes CpG containing motifs. This treatment enriches the samples for CpG content and eliminates redundant areas of the genome. Digested fragments were end-repaired and A-tailed with 5 units of Klenow fragment (3'-5' exo) and ligated overnight to Illumina adapters containing one of four barcode sequences to link each fragment to its sample ID. Size selection of 160-340 bp fragments (having 40-220 bp inserts) was performed using SPRI beads/buffer (AMPure XP, Beckman Coulter). Buffer cutoffs were from 0.7× to 1.1× of the sample volume of beads/buffer. Samples were eluted in a volume of 22 µl (EB buffer, Qiagen). qPCR was used to gauge ligation efficiency and fragment quality on a small aliquot of sample. Samples then underwent two rounds of bisulfite conversion using a modified EpiTect protocol (Qiagen). qPCR and conventional PCR (Pfu Turbo Cx hotstart, Agilent), followed by Bioanalyzer 2100 (Agilent) assessment on converted sample aliquots, determined the optimal PCR cycle number prior to amplification of the final library. The final PCR was performed in a volume of 50 µl (5 µl of 10×PCR buffer; 1.25 µl of each dNTP at 10 mM; 5 µl of a primer cocktail at approximately 5 µM, 15 µl of template (sample), 1 µl PfuTurbo Cx hotstart, and 22.75 µl water. Thermal cycling began with initial incubations at 95° C. for 5 minutes and at 98° C. for 30 seconds followed by 16 cycles of 98° C. for 10 seconds, 65° C. for 30 seconds, and at 72° C. for 30 seconds. After cycling, the samples were incubated at 72° C.

for 5 minutes and kept at 4° C. until further workup and analysis. Samples were combined in equimolar amounts into 4-plex libraries based on a randomization scheme and tested with the bioanalyzer for final size verification. Samples were also tested with qPCR using phiX standards and adaptor-specific primers.

For sequencing, samples were loaded onto flow cell lanes according to a randomized lane assignment with additional lanes reserved for internal assay controls. Sequencing was performed by the NGS Core at Mayo's Medical Genome Facility on the Illumina HiSeq 2000. Reads were unidirectional for 101 cycles. Each flow cell lane generated 100-120 million reads, sufficient for a median coverage of 30× to 50× sequencing depth (based on read number per CpG) for aligned sequences. Standard Illumina pipeline software was used to analyze the reads in combination with RRBSMAP (Xi, et al. (2012) "RRBSMAP: a fast, accurate and user-friendly alignment tool for reduced representation bisulfite sequencing" *Bioinformatics* 28: 430-432) and an in-house pipeline (SAAP-RRBS) developed by Mayo Biomedical and Statistics personnel (Sun et al. (2012) "SAAP-RRBS: streamlined analysis and annotation pipeline for reduced representation bisulfite sequencing" *Bioinformatics* 28: 2180-1). The bioinformatic analyses consisted of 1) sequence read assessment and clean-up, 2) alignment to reference genome, 3) methylation status extraction, and 4) CpG reporting and annotation.

Statistical Considerations

The primary comparison evaluated methylation differences between cases and pancreatic controls at each CpG and/or tiled CpG window. The secondary comparison evaluated methylation differences between cases and colon controls. Markers were tested for differential methylation by:
1. Assessing the distributions of methylation percentage for each marker and discarding markers that were more than 1% methylated in 10% of controls;
2. Testing the methylation distribution of the remaining markers between cases and controls using the Wilcoxon rank sum test and ranking markers by p-values; and
3. Using Q-values to estimate false discovery rates (FDR) (Benjamini et al. (1995) "Multiple Testing" *Journal of the Royal Statistical Society. Series B (Methodological)* 57: 289-300; Storey et al. (2003) "Statistical significance for genomewide studies" *Proc Natl Acad Sci USA* 100: 9440-5). At the discovery-level, an FDR up to 25% is acceptable.

Analysis of Data

A data analysis pipeline was developed in the R statistical analysis software package ("R: A Language and Environment for Statistical Computing" (2012), R Foundation for Statistical Computing). The workflow comprised the following steps:
1. Read in all 6,101,049 CpG sites
2. Identify for further analysis only those CpG sites where the total group depth of coverage is 200 reads or more. This cut-off was based on a power assessment to detect a difference of between 20% and 30% methylation between any two groups because anything less than this range has little chance of significance. Group depth of coverage measures the number of reads for all subjects in a group (e.g., if there are 18 subjects per group and each subject as 12 reads then the group depth of coverage is 12×18=216).
3. Estimate the association of disease subtype with the methylation % using variance inflated Poisson regression; the most discriminate CpG sites were determined by comparing the model-fit $X^2$ to the 95th percentile of all fitted models. Exclude all CpG sites where the variance of the methylation percent across the groups is 0 because these sites are non-informative CpG sites.

Applying the filters of 2 and 3 left a total of 1,217,523 CpG sites.
4. Perform logistic regression on the % methylation (based on the actual counts) using groups defined as Normal Colon, Normal Pancreas, and Cancerous Pancreas. Since the variability in the % methylation between subjects is larger than allowed by the binomial assumption, an over-dispersed logistic regression model was used to account for the increased variance. This dispersion parameter was estimated using the Pearson Chi-square of the fit.
5. From these model fits, calculate an overall F-statistic for the group comparison based on the change in deviance between the models with and without each group as a regressor. This deviance was scaled by the estimated dispersion parameter.
6. Create CpG islands on each chromosome based on the distance between CpG site locations. Roughly, when the distance between two CpG locations exceeds 100 bp, each location is defined as an independent island. Some islands were singletons and were excluded.
7. From the island definition above, the average F statistic is calculated. When the F statistic exceeds 95% (i.e., top 5%) of all CpG sites for the particular chromosome, a figure summary is generated.

Further analysis comprised the following selection filters:
1. ANOVA p-value cutoff <0.01
2. Ratios of % methylation PanC to normal pancreas and normal colon >10
3. % methylation of normals <2%
4. Number of contiguous CpGs meeting criteria ≥3

The methylation window was assessed to include additional contiguous CpGs that exhibit significant methylation. Then, the candidates were sorted by gene name for annotated regions and by chromosomal location for nonannotated regions.

Results

Roughly 6 million CpGs were mapped at ≥10× coverage. More than 500 CpG islands met significance criteria for differential methylation. After applying the filter criteria above, 107 differentially methylated regions (DMR) were identified (Table 1).

TABLE 1

| | | DMR | | |
|---|---|---|---|---|
| DMR No. | gene annotation | chromo- some | strand | region on chromosome (starting base-ending base) |
| 1 | none | 1 | F | 35394805-35394875 |
| 2 | none | 1 | F | 240161479-240161546 |
| 3 | none | 1 | R | 156406057-156406118 |
| 4 | AK055957 | 12 | F | 133484978-133485738 |
| 5 | none | 12 | R | 133484979-133485739 |
| 6 | APBA2 | 15 | F | 29131299-29131369 |
| 7 | none | 2 | F | 71503632-71503860 |
| 8 | PCBP3 | 21 | R | 47063793-47064177 |
| 9 | TMEM200A | 6 | F | 130687223-130687729 |
| 10 | none | 9 | R | 120507311-120507354 |
| 11 | ABCB1 | 7 | R | 87229775-87229856 |
| 12 | ADAMTS17 | 15 | R | 100881373-100881437 |
| 13 | ADAMTS18 | 16 | R | 77468655-77468742 |
| 14 | ADCY1 | 7 | F | 45613877-45614564 |
| 15 | ADCY1 | 7 | R | 45613878-45614572 |
| 16 | AGFG2 | 7 | F | 100136884-100137350 |
| 17 | ARHGEF7 | 13 | F | 111767862-111768355 |
| 18 | AUTS2 | 7 | R | 69062531-69062585 |
| 19 | BTBD11 | 12 | F | 107715014-107715095 |

TABLE 1-continued

| DMR No. | DMR gene annotation | chromosome | strand | region on chromosome (starting base-ending base) |
|---|---|---|---|---|
| 20 | BVES | 6 | R | 105584524-105584800 |
| 21 | c13orf18 | 13 | F | 46960770-46961464 |
| 22 | c13orf18 | 13 | R | 46960910-46961569 |
| 23 | CACNA1C | 12 | F | 2800665-2800898 |
| 24 | CBLN1 | 16 | R | 49315846-49315932 |
| 25 | CBS | 21 | F | 44496031-44496378 |
| 26 | CBS | 21 | R | 44495926-44496485 |
| 27 | CD1D | 1 | F | 158150797-158151142 |
| 28 | CELF2 | 10 | F | 11059508-11060151 |
| 29 | CLEC11A | 19 | F | 51228217-51228703 |
| 30 | CLEC11A | 19 | R | 51228325-51228732 |
| 31 | CNR1 | 6 | F | 88876367-88876445 |
| 32 | CNR1 | 6 | R | 88875699-88875763 |
| 33 | CHRH2 | 7 | F | 30721941-30722084 |
| 34 | DBNL | 7 | F | 44084171-44084235 |
| 35 | DBX1 | 11 | R | 20178177-20178304 |
| 36 | DHRS12 | 13 | F | 52378159-52378202 |
| 37 | DLL1 | 6 | F | 170598241-170600366 |
| 38 | ELMO1 | 7 | F | 37487539-37488498 |
| 39 | ELMO1 | 7 | R | 37487540-37488477 |
| 40 | EN1 | 2 | R | 119607676-119607765 |
| 41 | EOMES | 3 | F | 27763358-27763617 |
| 42 | FBLN1 | 22 | R | 45898798-45898888 |
| 43 | FEM1C | 5 | F | 114880375-114880442 |
| 44 | FER1L4 | 20 | R | 34189679-34189687 |
| 45 | FKBP2 | 11 | F | 64008415-64008495 |
| 46 | FLT3 | 13 | F | 28674451-28674629 |
| 47 | FNIP1 | 5 | F | 131132146-131132232 |
| 48 | FOXP2 | 7 | R | 113727624-113727693 |
| 49 | GFRA4 | 20 | R | 3641457-3641537 |
| 50 | GJC1 | 17 | F | 42907705-42907798 |
| 51 | GJC1 | 17 | R | 42907752-42907827 |
| 52 | GRIN2D | 19 | F | 48946755-48946912 |
| 53 | HECW1 | 7 | R | 43152309-43152375 |
| 54 | HOXA1 | 7 | R | 27136030-27136245 |
| 55 | IFIH1 | 2 | R | 163174541-163174659 |
| 56 | IGF2BP1 | 17 | F | 47073394-47073451 |
| 57 | IKZF1 | 7 | R | 50343848-50343927 |
| 58 | INSM1 (region 1) | 20 | F | 20345123-20345150 |
| 59 | INSM1 (region 2) | 20 | F | 20350520-20350532 |
| 60 | KCNK12 | 2 | F | 47797332-47797371 |
| 61 | KCNN2 | 5 | F | 113696984-113697057 |
| 62 | KCTD15 | 19 | R | 34287890-34287972 |
| 63 | LINGO3 | 19 | F | 2290471-2290541 |
| 64 | LOC100126784 | 11 | R | 19733958-19734013 |
| 65 | LOC63930 | 20 | F | 61637950-61638000 |
| 66 | LOC642345 | 13 | R | 88323571-88323647 |
| 67 | MLLT1 | 19 | R | 6236992-6237089 |
| 68 | MPND | 19 | R | 4343896-4242968 |
| 69 | MYEF2 | 15 | F | 48470117-48470606 |
| 70 | NDUFAB1 | 16 | R | 23607524-23607650 |
| 71 | NFASC | 1 | F | 204797781-204797859 |
| 72 | NR5A1 | 9 | F | 127266951-127267032 |
| 73 | PDE6B | 4 | F | 657586-657665 |
| 74 | PLAGL1 | 6 | R | 144384503-144385539 |
| 75 | PRKCB | 16 | R | 23846964-23848004 |
| 76 | PRRT3 | 3 | F | 9988302-9988499 |
| 77 | PTF1A | 10 | F | 23480864-23480913 |
| 78 | RASGRF2 | 5 | F | 80256215-80256313 |
| 79 | RIMKLA | 1 | R | 42846119-42846174 |
| 80 | RNF216 | 7 | F | 5821188-5821283 |
| 81 | RSPO3 | 6 | F | 127440526-127441039 |
| 82 | RSPO3 | 6 | R | 127440492-127440609 |
| 83 | RYBP | 3 | R | 72496092-72496361 |
| 84 | SCARF2 | 22 | F | 20785373-20785464 |
| 85 | SHH | 7 | F | 155597771-155597951 |
| 86 | SLC35E3 | 12 | F | 69140018-69140202 |
| 87 | SLC38A3 | 3 | R | 50243467-50243553 |
| 88 | SLC6A3 | 5 | R | 1445384-1445473 |
| 89 | SPSB4 | 3 | F | 140770135-140770193 |
| 90 | SRCIN1 | 17 | R | 36762706-36762763 |
| 91 | ST6GAL2 | 2 | F | 107502978-107503055 |
| 92 | ST6GAL2 | 2 | R | 107503155-107503391 |
| 93 | ST8SIA1 | 12 | F | 22487528-22487827 |
| 94 | ST8SIA1 | 12 | R | 22487664-22487848 |
| 95 | ST8SIA6 | 10 | F | 17496177-17496310 |
| 96 | SUSD5 | 3 | R | 33260338-33260423 |
| 97 | TOX2 | 20 | F | 42544666-42544874 |
| 98 | TWIST1 | 7 | F | 19156788-19157093 |
| 99 | TWIST1 | 7 | R | 19156815-19157227 |
| 100 | USP3 | 15 | R | 63795435-63795636 |
| 101 | USP44 | 12 | R | 95942179-95942558 |
| 102 | VIM | 10 | F | 17271896-17271994 |
| 103 | VWC2 | 7 | R | 49813182-49814168 |
| 104 | WT1 | 11 | R | 32460759-32460800 |
| 105 | ZFP30 | 19 | F | 38146299-38146397 |
| 106 | ZNF570 | 19 | F | 37958078-37958134 |
| 107 | ZNF71 | 19 | F | 57106617-57106852 |

In Table 1, bases are numbered according to the February 2009 human genome assembly GRCh37/hg19 (see, e.g., Rosenbloom et al. (2012) "ENCODE whole-genome data in the UCSC Genome Browser: update 2012" *Nucleic Acids Research* 40: D912-D917). The marker names BHLHE23 and LOC63930 refer to the same marker.

In these candidates, methylation signatures range from 3 neighboring CpGs to 52 CpGs. Some markers exhibit methylation on both strands; others are hemi-methylated. Since strands are not complimentary after bisulfite conversion, forward and reverse regions were counted separately. While Table 1 indicates the strand on which the marker is found, the technology is not limited to detecting methylation on only the indicated strand. The technology encompasses measuring methylation on either forward or reverse strands and/or on both forward and reverse strands; and/or detecting a change in methylation state on either forward or reverse strands and/or on both forward and reverse strands.

Methylation levels of the pancreatic cancers rarely exceeded 25% at filtered CpGs, which suggested that the cancer tissues may have high levels of contaminating normal cells and/or stroma. To test this, each of the cancers was sequenced for KRAS mutations to verify allele frequencies for the positive samples. For the 50% that harbored a heterozygous KRAS base change, the frequency of the mutant allele was at least 4 times less than the corresponding wild-type allele, in support of contamination by normal cells and/or stroma.

It was found that 7 of the 107 markers are in nonannotated regions and lie in genomic regions without protein coding elements. One marker is adjacent to a ncRNA regulatory sequence (AK055957). Of the remaining 99 candidate markers, approximately 30 have been described as associated with cancer, some of which classify as tumor suppressors. A few examples:

ADCY1 Down-regulated in osteosarcoma
ELMO1 Promotes glioma invasion
HOXA2 Hyper-methylated in cholangioca
RSPO3 Wnt signalling regulator
SUSD5 Mediates bone metastasis in lung cancer
KCNK12 Hypermethylated in colon cancer
CLEC11A Stem cell GF in leukemia
USP3 Required for S-phase progression The 69 other candidate markers have a previously identified weak association with cancer (e.g., mutations and/or copy number alterations observed in genome-wide screens) or have no previously identified cancer associations.

Example 2—Validating Markers

To validate the DMRs as cancer markers, two PCR-based validation studies were performed on expanded sample sets. The first study used samples from patient groups similar to those used in Example 1 (e.g., PanC, normal pancreas, normal colon) and added samples comprising buffy coat-derived DNA from normal patients who had no history of any cancer. The second study used using a selection of pan-GI cancers.

For the first validation study, a combination of previously run RRBS samples and newer banked samples were tested to verify technical accuracy and to confirm biological reproducibility, respectively. Methylation specific PCR (MSP) primers were designed for each of the marker regions, excluding only complementary strands in cases of non-strand specific methylation. Computer software (Methprimer) aided semi-manual design of the MSP primers by experienced personnel; assays were tested and optimized by qPCR with SYBR Green dyes on dilutions of universally methylated and unmethylated genomic DNA controls. The MSP primer sequences, each of which include 2-4 CpGs, were designed to provide a quick means of assessing methylation in the samples and were biased to maximize amplification efficiency. Primer sequences and physical parameters are provided in Table 2a and Table 2b:

TABLE 2a

MSP primers

| Name | Length (nt) | Sequence (5'→3') | GC Content (%) | Tm | Ta | SEQ ID NO: |
|---|---|---|---|---|---|---|
| abcb1f | 21 | GAT TTT GTT CGT CGT TAG TGC | 42.9 | 52.3 | 60.0 | 1 |
| abcb1r | 19 | TCT CTA AAC CCG CGA ACG A | 52.6 | 56.0 | 60.0 | 2 |
| adamts17f | 25 | TTC GAA GTT TCG GGA TAG GAA GCG T | 48.0 | 60.0 | 65.0 | 3 |
| adamts17r | 20 | CCT ACC GAC CTT CGA ACG CG | 65.0 | 60.3 | 65.0 | 4 |
| adamts18f | 21 | GGC GGC GCG TAT TTT TTT CGC | 57.1 | 60.6 | 60.0 | 5 |
| adamts18r | 23 | CGC TAC GAT ATA AAC GAC GAC GA | 47.8 | 56.4 | 60.0 | 6 |
| adcy1f | 19 | GGT TCG GTT GTC GTA GCG C | 63.2 | 59.0 | 65.0 | 7 |
| adcy1r | 20 | CCG ACC GTA ATC CTC GAC GA | 60.0 | 58.6 | 65.0 | 8 |
| agfg2f | 25 | TTA GGT CGG GAA TCG TTA TTG TTT C | 40.0 | 55.1 | 60.0 | 9 |
| agfg2r | 22 | GTA AAT AAC CCC GCG CTA AAC G | 50.0 | 56.5 | 60.0 | 10 |
| arhgef7f | 24 | TTC GTT TGT TTT TCG GGT CGT AGC | 45.8 | 58.1 | 60.0 | 11 |
| arhgef7r | 24 | ACC ACG TAA CGA TTT ACT CGA CGA | 45.8 | 57.8 | 60.0 | 12 |
| auts2f | 23 | CGT TTT CGG ATT TGA AGT CGT TC | 43.5 | 54.8 | 65.0 | 13 |
| auts2r | 19 | CGC CTC GTC TTC CAA CGA A | 57.9 | 57.7 | 65.0 | 14 |
| btbd11f | 19 | AGG GCG TTC GGT TTT AGT C | 52.6 | 55.1 | 60.0 | 15 |
| btbd1r | 22 | AAC CGA AAA CGA CAA AAT CGA T | 36.4 | 53.4 | 60.0 | 16 |
| Bvesf | 21 | TTT GAG CGG CGG TCG TTG ATC | 57.1 | 60.4 | 60.0 | 17 |
| Bvesr | 22 | TCC CCG AAT CTA AAC GCT ACG A | 50.0 | 57.8 | 60.0 | 18 |
| C13orf18f | 25 | TTT AGG GAA GTA AAG CGT CGT TTT C | 40.0 | 55.6 | 60.0 | 19 |
| C13orf18r | 22 | AAC GAC GTC TCG ATA CCT ACG A | 50.0 | 57.1 | 60.0 | 20 |
| cacna1cf | 22 | GGA GAG TAT TTC GGT TTT TCG C | 45.5 | 54.2 | 65.0 | 21 |
| cacna1cr | 24 | ACA AAC AAA ATC GAA AAA CAC CCG | 37.5 | 55.2 | 65.0 | 22 |
| cbln1f | 23 | GTT TTC GTT TCG GTC GAG GTT AC | 47.8 | 56.2 | 60.0 | 23 |
| cbln1r | 25 | GCC ATT AAC TCG ATA AAA AAC GCG A | 40.0 | 56.3 | 60.0 | 24 |
| Cbsf | 25 | GAT TTA ATC GTA GAT TCG GGT CGT C | 44.0 | 55.2 | 65.0 | 25 |
| Cbsr | 22 | CCG AAA CGA ACG AAC TCA AAC G | 50.0 | 56.8 | 65.0 | 26 |
| cd1df | 17 | GCG CGT AGC GGC GTT TC | 70.6 | 60.7 | 60.0 | 27 |
| cd1dr | 19 | CCC ATA TCG CCC GAC GTA A | 57.9 | 56.9 | 60.0 | 28 |
| celf2f | 22 | TCG TAT TTG GCG TTC GGT AGT C | 50.0 | 57.0 | 70.0 | 29 |
| celf2r | 21 | CGA AAT CCA ACG CCG AAA CGA | 52.4 | 58.4 | 70.0 | 30 |

TABLE 2a-continued

MSP primers

| Name | Length (nt) | Sequence (5'→3') | GC Content (%) | Tm | Ta | SEQ ID NO: |
|---|---|---|---|---|---|---|
| chr1 156f | 24 | TTG TCG TTC GTC GAA TTC GAT TTC | 41.7 | 55.8 | 65.0 | 31 |
| chr1 156r | 23 | AAC CCG ACG CTA AAA AAC GAC GA | 47.8 | 59.2 | 65.0 | 32 |
| chr1 240f | 25 | TTG CGT TGG TTA CGT TTT TTT ACG C | 40.0 | 57.3 | 60.0 | 33 |
| chr1 240r | 23 | ACG CCG TAC GAA TAA CGA AAC GA | 47.8 | 58.7 | 60.0 | 34 |
| chr1 353f | 21 | CGT TTT TCG GGT CGG GTT CGC | 61.9 | 61.5 | 60.0 | 35 |
| chr1 353r | 19 | TCC GAC GCT CGA CTC CCG A | 68.4 | 63.1 | 60.0 | 36 |
| chr12 133f | 22 | TCG GCG TAT TTT TCG TAG ACG C | 50.0 | 57.6 | 60.0 | 37 |
| chr12 133r | 24 | CGC AAT CTT AAA CGT ACG CTT CGA | 45.8 | 57.7 | 60.0 | 38 |
| chr15 291 (apba2)f | 24 | GGT TTA TAA AGA GTT CGG TTT CGC | 41.7 | 54.4 | 60.0 | 39 |
| chr15 291 (apba2)r | 24 | AAA ACG CTA AAC TAC CCG AAT ACG | 41.7 | 55.3 | 60.0 | 40 |
| chr2 715f | 19 | TGG GCG GGT TTC GTC GTA C | 63.2 | 60.2 | 65.0 | 41 |
| chr2 715r | 21 | GTC CCG AAA CAT CGC AAA CGA | 52.4 | 58.2 | 65.0 | 42 |
| chr6 130 (TMEM200A)f | 20 | GCG TTT GGA TTT TGC GTT C | 55.0 | 58.0 | 60.0 | 43 |
| chr6 130 (TMEM200A)r | 20 | AAA ATA CGC CGC TAC CGA TA | 55.0 | 60.6 | 60.0 | 44 |
| chr9 120f | 20 | GTT TAG GGA GTC GCG GTT AC | 55.0 | 55.4 | 60.0 | 45 |
| chr9 120r | 23 | CAA ATC CTA CGA ACG AAC GAA CG | 47.8 | 56.2 | 60.0 | 46 |
| clec11af | 22 | AGT TTG GCG TAG TCG GTA GAT | 50.0 | 56.4 | 60.0 | 47 |
| clec11ar | 22 | GCG CGC AAA TAC CGA ATA AAC | 50.0 | 57.5 | 60.0 | 48 |
| cnr1f | 22 | TCG GTT TTT AGC GTT CGT TCG C | 50.0 | 58.4 | 60.0 | 49 |
| cnr1r | 23 | AAA CAA CGA AAC GCC AAT CCC GA | 47.8 | 59.9 | 60.0 | 50 |
| crhr2f | 25 | TAG TTT TTG GGC GTT ATT TTC GGT C | 40.0 | 56.1 | 60.0 | 51 |
| crhr2r | 21 | GCA ACT CCG TAC ACT CGA CGA | 57.1 | 59.0 | 60.0 | 52 |
| Dbn1f | 26 | TTT TTC GTT TGT TTT TCG GTA TTC GC | 34.6 | 55.5 | 60.0 | 53 |
| Dbn1r | 22 | CGA ATC CTA ACG AA AAC TAT CCG A | 45.5 | 53.9 | 60.0 | 54 |
| dbx1f | 25 | TTC GGT GGA TTT TCG TAT TGA TTT C | 36.0 | 54.0 | 60.0 | 55 |
| dbx1r | 24 | AAA CGA AAC CGC GAA CTA AAA CGA | 41.7 | 57.6 | 60.0 | 56 |
| dhrs12f | 22 | TTA CGT GAT AGT TCG GGG TTT C | 45.5 | 54.6 | 60.0 | 57 |
| dhrs12r | 21 | ATA AAA CGA CGC GAC GAA ACG | 47.6 | 56.2 | 60.0 | 58 |
| elmo1f | 24 | TTT CGG GTT TTG CGT TTT ATT CGC | 41.7 | 57.2 | 60.0 | 59 |
| elmo1r | 28 | GAA AAA AAA AAA CGC TAA AAA TAC GAC G | 28.6 | 53.3 | 60.0 | 60 |
| Eomesf | 21 | TAG CGC GTA GTG GTC GTA GTC | 57.1 | 58.4 | 60.0 | 61 |
| Eomesr | 18 | CCT CCG CCG CTA CAA CCG | 72.2 | 61.5 | 60.0 | 62 |
| fbln1f | 22 | TCG TTG TTT TAG GAT CGC GTT C | 45.5 | 55.6 | 60.0 | 63 |
| fbln1r | 22 | GAC GAA CGA TAA ACG ACG ACG A | 50.0 | 56.9 | 60.0 | 64 |
| fem1cf | 21 | TTC GGT CGC GTT GTT CGT TAC | 52.4 | 58.0 | 60.0 | 65 |

TABLE 2a-continued

MSP primers

| Name | Length (nt) | Sequence (5'→3') | GC Content (%) | Tm | Ta | SEQ ID NO: |
|---|---|---|---|---|---|---|
| fem1cr | 25 | AAA CGA AAA ACA ACT CGA ATA ACG A | 32.0 | 53.8 | 60.0 | 66 |
| fer1I4f | 18 | AGT CGG GGT CGG AGT CGC | 72.2 | 62.3 | 60.0 | 67 |
| fer1I4r | 23 | ATA AAT CCC TCC GAA ACC CAC GA | 47.8 | 58.2 | 60.0 | 68 |
| fkbp2f | 21 | TCG GAA GTG ACG TAG GGT AGC | 57.1 | 58.3 | 60.0 | 69 |
| fkbp2r | 19 | CAC ACG CCC GCT AAC ACG A | 63.2 | 60.6 | 60.0 | 70 |
| flt3f | 21 | GCG CGT TCG GGT TTA TAT TGC | 52.4 | 57.2 | 65.0 | 71 |
| flt3r | 20 | GAC CAA CTA CCG CTA CTC GA | 55.0 | 56.1 | 65.0 | 72 |
| fnip1f | 20 | AGG GGA GAA TTT CGC GGT TC | 55.0 | 57.6 | 65.0 | 73 |
| fnip1r | 24 | AAC TAA ATT AAA CCT CAA CCG CCG | 41.7 | 55.9 | 65.0 | 74 |
| gfra4f | 20 | TTA GGA GGC GAG GTT TGC GC | 60.0 | 60.3 | 65.0 | 75 |
| gfra4r | 28 | GAC GAA ACC GTA ACG AAA ATA AAA ACG A | 35.7 | 56.4 | 65.0 | 76 |
| gjc1r | 24 | CGA ACT ATC CGA AAA AAC GAC GAA | 41.7 | 55.6 | 65.0 | 77 |
| glc1f | 22 | GCG ACG CGA GCG TTA ATT TTT C | 50.0 | 57.6 | 65.0 | 78 |
| hecw1f | 23 | TTC GCG TAT ATA TTC GTC GAG TC | 43.5 | 54.2 | 60.0 | 79 |
| hecw1r | 20 | CAC GAC CAC TAT CAC GAC GA | 55.0 | 56.5 | 60.0 | 80 |
| hoxa1f | 22 | GTA CGT CGG TTT AGT TCG TAG C | 50.0 | 55.3 | 60.0 | 81 |
| hoxa1r | 21 | CCG AAA CGC GAT ATC AAC CGA | 52.4 | 57.6 | 60.0 | 82 |
| ifih1f | 20 | CGG GCG GTT AGA GGG TTG TC | 65.0 | 60.4 | 60.0 | 83 |
| ifih1r | 26 | CTC GAA AAT TCG TAA AAA CCC TCC GA | 42.3 | 57.4 | 60.0 | 84 |
| igf2bp1f | 29 | CGA GTA GTT TTT TTT TTT ATC GTT TAG AC | 27.6 | 52.1 | 65.0 | 85 |
| igf2bp1r | 24 | CAA AAA ACG ACA CGT AAA CGA TCG | 41.7 | 55.2 | 65.0 | 86 |
| ikzf1f | 24 | GTT TCG TTT TGC GTT TTT TTG CGC | 41.7 | 57.5 | 65.0 | 87 |
| ikzf1r | 19 | TCC CGA ATC GCT ACT CCG A | 57.9 | 57.8 | 65.0 | 88 |
| insm1 reg1f | 17 | GCG GTT AGG CGG GTT GC | 70.6 | 60.2 | 60.0 | 89 |
| insm1 reg1r | 25 | ATT ATA TCA ATC CCA AAA ACA CGC | 36.0 | 54.3 | 60.0 | 90 |
| insm1 reg2f | 22 | TAT TTT TCG AAT TCG AGT TCG C | 36.4 | 51.7 | 60.0 | 91 |
| insm1 reg2r | 22 | TCA CCC GAT AAA AAC GAA AAC G | 40.9 | 53.8 | 60.0 | 92 |
| kcnk12f | 21 | GCG TCG TTA GTA GTA CGA AGC | 52.4 | 55.3 | 60.0 | 93 |
| kcnk12r | 21 | GCA CCT CAA CGA AAA CAC CGA | 52.4 | 58.2 | 60.0 | 94 |
| kcnn2f | 23 | TCG AGG CGG TTA ATT TTA TTC GC | 43.5 | 55.8 | 65.0 | 95 |
| kcnn2r | 23 | GCT CTA ACC CAA ATA CGC TAC GA | 47.8 | 56.6 | 65.0 | 96 |
| kctd15f | 22 | TCG GTT TCG AGG TAA GTT TAG C | 45.5 | 54.7 | 60.0 | 97 |
| kctd15r | 23 | CAC TTC GAA ACA AAA TTA CGC GA | 39.1 | 54.3 | 60.0 | 98 |
| lingo3f | 20 | GGA AGC GGA CGT TTT CGT TC | 55.0 | 56.8 | 65.0 | 99 |
| lingo3r | 22 | ACC CAA AAT CCG AAA ACG ACG A | 45.5 | 57.3 | 65.0 | 100 |
| LOC100126784 (NAV2)f | 19 | AGG TTG CGG GCG TGA TTT C | 57.9 | 58.8 | 65.0 | 101 |

TABLE 2a-continued

MSP primers

| Name | Length (nt) | Sequence (5'→3') | GC Content (%) | Tm | Ta | SEQ ID NO: |
|---|---|---|---|---|---|---|
| LOC100126784 (NAV2)r | 20 | CCA AAA CCA CGC GAA CAC GA | 55.0 | 58.8 | 65.0 | 102 |
| LOC63930 (bhlhe23)f | 20 | GTT CGG AGT GTC GTA GTC GC | 60.0 | 57.7 | 70.0 | 103 |
| LOC63930 (bhlhe23)r | 21 | AAT CTC GCC TAC GAA ACG ACG | 52.4 | 57.2 | 70.0 | 104 |
| LOC642345f | 22 | GTT TAG GGA CGT TTT CGT TTT C | 40.9 | 52.5 | 65.0 | 105 |
| LOC642345r | 20 | AAC GAA CGC TCG ATA ACC GA | 50.0 | 56.5 | 65.0 | 106 |
| mllt1f | 20 | TTT GGG TCG GGT TAG GTC GC | 60.0 | 59.9 | 60.0 | 107 |
| mllt1r | 25 | GAA ACC AAA AAA ACG CTA ACT CGT A | 36.0 | 54.4 | 60.0 | 108 |
| Mpndf | 20 | CGT TGT TGG AGT TTG GCG TC | 55.0 | 57.1 | 65.0 | 109 |
| Mpndr | 21 | TAC CCG AAC CGC GAT AAA ACG | 52.4 | 57.5 | 65.0 | 110 |
| myef2f | 25 | GGT ATA GTT CGG TTT TTA GTC GTT C | 40.0 | 53.6 | 65.0 | 111 |
| myef2r | 24 | TCT TTT CCT CCG AAA ACC GAA ACG | 45.8 | 57.8 | 65.0 | 112 |
| NDUFAB1f | 23 | GGT TAC GGT TAG TAT TCG GAT TC | 43.5 | 53.0 | 60.0 | 113 |
| NDUFAB1r | 20 | ATA TCA CCG CCT ACC CCG CG | 60.0 | 59.7 | 60.0 | 114 |
| NFASCf | 24 | TTT TGT TTT AAT GCG GCG GTT GGC | 45.8 | 59.6 | 65.0 | 115 |
| NFASCr | 22 | TAT CCG AAC TAT CCG CTA CCG A | 50.0 | 56.9 | 65.0 | 116 |
| pcbp3f | 19 | GGT CGC GTC GTT TTC GAT C | 57.9 | 56.6 | 60.0 | 117 |
| pcbp3r | 17 | GCC GCA AAC GCC GAC GA | 70.6 | 62.4 | 60.0 | 118 |
| PDE6Bf | 21 | AAT CGG CGG TAG TAC GAG TAC | 52.4 | 56.1 | 55.0 | 119 |
| PDE6Br | 26 | AAA CCA AAT CCG TAA CGA TAA TAA CG | 34.6 | 53.9 | 55.0 | 120 |
| PLAGL1f | 26 | GAG TTT TGT TTT CGA AAT TAT TTC GC | 30.8 | 52.4 | 65.0 | 121 |
| PLAGL1r | 18 | CCC GAA TTA CCG ACG ACG | 61.1 | 55.7 | 65.0 | 122 |
| PRKCBf | 21 | AGG TTC GGG TTC GAC GAT TTC | 52.4 | 57.3 | 70.0 | 123 |
| PRKCBr | 21 | AAC TCT ACA ACG CCG AAA CCG | 52.4 | 57.7 | 70.0 | 124 |
| PRRT3f | 23 | TTA GTT CGT TTA GCG ATG GCG TC | 47.8 | 57.4 | 60.0 | 125 |
| PRRT3r | 20 | CCG AAA CTA TCC CGC AAC GA | 55.0 | 57.5 | 60.0 | 126 |
| PTF1Af | 21 | TTC GTC GTT TGG GTT ATC GGC | 52.4 | 57.8 | 60.0 | 127 |
| PTF1Ar | 23 | GCC CTA AAA CTA AAA CAA CCG CG | 47.8 | 57.1 | 60.0 | 128 |
| RASGRF2f | 22 | GGT TGT CGT TTT AGT TCG TCG C | 50.0 | 56.6 | 60.0 | 129 |
| RASGRF2r | 19 | GCG AAA ACG CCC GAA CCG A | 63.2 | 61.4 | 60.0 | 130 |
| RIMKLAf | 22 | TCG TTT GGG AGA CGT ATT CGT C | 50.0 | 56.7 | 60.0 | 131 |
| RIMKLAr | 25 | ACT CGA AAA ATT TCC GAA CTA ACG A | 36.0 | 55.0 | 60.0 | 132 |
| RNF216f | 20 | TCG GCG GTT TTC GTT ATC GC | 55.0 | 58.4 | 60.0 | 133 |
| RNF216r | 21 | CCA CGA AAC TCG CAA CTA CGA | 52.4 | 57.4 | 60.0 | 134 |
| rspo3f | 25 | CGT TTA TTT AGC GTA ATC GTT TCG C | 40.0 | 55.0 | 65.0 | 135 |
| rspo3r | 24 | GAA TAA CGA ACG TTC GAC TAC CGA | 45.8 | 56.6 | 65.0 | 136 |

TABLE 2a-continued

MSP primers

| Name | Length (nt) | Sequence (5'→3') | GC Content (%) | Tm | Ta | SEQ ID NO: |
|---|---|---|---|---|---|---|
| RYBPf | 24 | CGG ACG AGA TTA GTT TTC GTT AGC | 45.8 | 55.7 | 60.0 | 137 |
| RYBPr | 24 | TCG TCA ATC ACT CGA CGA AAA CGA | 45.8 | 58.4 | 60.0 | 138 |
| SCARF2f | 22 | TCG GTT CGT AGG TAT ACG TGT C | 50.0 | 55.8 | 60.0 | 139 |
| SCARF2r | 22 | GCT ACT ACC AAT ACT TCC GCG A | 50.0 | 56.4 | 60.0 | 140 |
| SLC35E3f | 21 | GTT AGA CGG TTT TAG TTT CGC | 42.9 | 51.8 | 60.0 | 141 |
| SLC35E3r | 20 | AAA AAC CCG ACG ACG ATT CG | 50.0 | 55.8 | 60.0 | 142 |
| slc38a3f | 21 | GTT AGA GTT CGC GTA GCG TAC | 52.4 | 55.3 | 65.0 | 143 |
| slc38a3r | 25 | GAA AAA CCA ACC GAA CGA ACG AAA ACG A | 40.0 | 56.9 | 65.0 | 144 |
| slc6a3f | 19 | CGG GGC GTT TCG ATG TCG C | 68.4 | 62.0 | 65.0 | 145 |
| slc6a3r | 24 | CCG AAC GAC CAA ATA AAA CCA ACG | 45.8 | 57.0 | 65.0 | 146 |
| srcin1f | 22 | CGT TTT ATG TTG GGA GCG TTC G | 50.0 | 56.8 | 65.0 | 147 |
| srcin1r | 20 | GAC CGA ACC GCG TCT AAA CG | 60.0 | 58.5 | 65.0 | 148 |
| st6gal12f | 21 | TAC GTA TCG AGG TTG CGT CGC | 57.1 | 59.3 | 65.0 | 149 |
| st6gal2r | 25 | AAA CTC TAA AAC GAA CGA AAC TCG A | 36.0 | 54.9 | 65.0 | 150 |
| st8sia1f | 21 | TCG AGA CGC GTT TTT TGC GTC | 52.4 | 58.7 | 60.0 | 151 |
| st8sia1r | 20 | AAC GAT CCC GAA CCG CCG TA | 60.0 | 61.3 | 60.0 | 152 |
| ST8SIA6f | 21 | CGA GTA GTG CGT TTT TCG GTC | 52.4 | 56.2 | 60.0 | 153 |
| ST8SIA6r | 22 | GAC AAC AAC GAT AAC GAC GAC G | 50.0 | 56.1 | 60.0 | 154 |
| SUSD5f | 22 | AGC GTG CGT TAT TCG GTT TTG C | 50.0 | 59.1 | 65.0 | 155 |
| SUSD5r | 23 | ACC TAC GAT TCG TAA ACC GAA CG | 47.8 | 56.9 | 65.0 | 156 |
| TOX2f | 23 | AGT TCG CGT TTT TTT CGG TCG TC | 47.8 | 58.5 | 70.0 | 157 |
| TOX2r | 21 | AAC CGA CGC ACC GAC TAA CGA | 57.1 | 61.0 | 70.0 | 158 |
| twist1f | 22 | TTG CGT CGT TTG CGT TTT TCG C | 50.0 | 59.9 | 60.0 | 159 |
| twist1r | 20 | CAA CTC GCC AAT CTC GCC GA | 60.0 | 60.2 | 60.0 | 160 |
| USP3f | 18 | TAT TGC GGG GAG GTG TTC | 55.6 | 54.7 | 60.0 | 161 |
| USP3r | 24 | TCA AAA AAT AAT TAA CCG AAC CGA | 29.2 | 51.3 | 60.0 | 162 |
| USP44f | 24 | TTA GTT TTC GAA GTT TTC GTT CGC | 37.5 | 54.4 | 60.0 | 163 |
| USP44r | 19 | TCC GAC CCT ATC CCG ACG A | 63.2 | 59.9 | 60.0 | 164 |
| VIMf | 27 | GAT TAG TTA ATT AAC GAT AAA GTT CGC | 29.6 | 51.0 | 60.0 | 165 |
| VIMr | 23 | CCG AAA ACG CAT AAT ATC CTC GA | 43.5 | 55.0 | 60.0 | 166 |
| vwc2f | 26 | TTG GAG AGT TTT TCG AAT TTT TTC GC | 34.6 | 55.2 | 65.0 | 167 |
| vwc2r | 19 | GAA AAC CAC CCT AAC GCC G | 57.9 | 56.6 | 65.0 | 168 |
| wt1f | 17 | CGC GGG GTT CGT AGG TC | 70.6 | 58.5 | 65.0 | 169 |
| wt1r | 23 | CGA CAA ACA ACA ACG AAA TCG AA | 39.1 | 54.5 | 65.0 | 170 |
| zfp30f | 22 | AGT AGC GGT TAT AGT GGC GTT C | 50.0 | 56.7 | 65.0 | 171 |
| zfp30r | 22 | GCA TTC GCG ACG AAA ACA AAC G | 50.0 | 58.0 | 65.0 | 172 |
| ZNF569f | 20 | GTA TTG AGG TCG GCG TTG TC | 55.0 | 55.9 | 60.0 | 173 |

TABLE 2a-continued

MSP primers

| Name | Length (nt) | Sequence (5'→3') | GC Content (%) | Tm | Ta | SEQ ID NO: |
|---|---|---|---|---|---|---|
| ZNF569r | 19 | CCG CCC GAA TAA ACC GCG A | 63.2 | 60.8 | 60.0 | 174 |
| ZNF71f | 20 | CGT AGT TCG GCG TAG TTC GC | 60.0 | 58.2 | 65.0 | 175 |
| ZNF71r | 21 | AAC CCG CCC GAC GAC AAT ACG | 61.9 | 62.1 | 65.0 | 176 |

In Table 2a, Ta is the optimized annealing temperature and Tm is the melting temperature in °C. in 50 mM NaCl. Primers celf2f and celf2r; LOC63930 (bhlhe23)f and LOC63930 (bhlhe23)r; PRKCBf and PRKCBr; and TOX2f and TOX2r are used in a 2-step reaction.

Specimens

Archived DNA samples from Mayo clinic patients were used for both validations. Cases and controls were blinded and matched by age and sex. The first sample set included DNA from 38 pancreatic adenocarcinomas and controls (20 normal colonic epithelia, 15 normal pancreas, and 10 normal buffy coats). The second sample set included DNA from 38 colorectal neoplasms (20 colorectal adenocarcinomas and 18 adenomas >1 cm), 19 esophageal adenocarcinomas, 10 gastric (stomach) cancers, and 10 cholangiocarcinomas.

Methods

Archived DNA was re-purified using SPRI beads (AMPure XP-Beckman Coulter) and quantified by absorbance. 1-2 μg of sample DNA was then treated with sodium bisulfite and purified using the EpiTect protocol (Qiagen). Eluted material (10-20 ng) was amplified on a Roche 480 LightCycler using 384-well blocks. Each plate accommodated 4 markers (and standards and controls), thus using a total of 23 plates. The 88 MSP assays had differing optimal amplification profiles and were grouped accordingly. Specific annealing temperatures are provided in Table 2. The 20-μl reactions were run using LightCycler 480 SYBR I Master mix (Roche) and 0.5 μmol of primer for 50 cycles and analyzed, generally, by the 2nd-derivative method included with the LightCycler software. The raw data, expressed in genomic copy number, was normalized to the amount of input DNA, and tabulated. Analysis at the tissue level comprised performing PCA (supplemented with k-fold cross validation), elastic net regression, and constructing box plots of non-zero elastic net markers. In this way, markers were collectively ranked. Of these candidates, because of the importance of minimizing normal cellular background methylation for stool and blood-based assays, the ranking was weighed toward those markers which exhibited the highest fold-change differential between cases and controls.

Results

Among the 107 methylated DNA markers with proven discrimination for GI cancers, MSP validation was performed on 88 from which subsets were identified for display of more detailed summary data.

Detection of Pancreatic Cancer

A subset of the methylation markers were particularly discriminant for pancreatic cancer: ABCB1, ADCY1, BHLHE23 (LOC63930), c13orf18, CACNA1C, chr12 133, CLEC11A, ELMO1, EOMES, GJC1, IHIF1, IKZF1, KCNK12, KCNN2, PCBP3, PRKCB, RSPO3, SCARF2, SLC38A3, ST8SIA1, TWIST1, VWC2, WT1, and ZNF71 (see Table 1). Individual AUC values (PanC versus normal pancreas or colon) for these markers were above 0.87, which indicates superior clinical sensitivity and specificity.

Initially, the two best stand-alone markers appeared to be CLEC11A and c13orf18, which were 95% and 82% sensitive for pancreatic cancer, respectively, at 95% specificity. Additional experiments designed additional primers to target the most specific CpGs within specified DMRs of selected markers. These additional primers enhanced discrimination further. For example, design of new MSP for the marker PRKCB (initial sensitivity of 68%) dramatically increased discrimination for pancreatic cancer and achieved sensitivity of 100% at 100% specificity. Moreover, the median methylation signal-to-noise ratio for this marker, comparing cancer to normal tissue, was greater than 8000. This provides a metric critical to the detection of cancer markers in samples with high levels of normal cellular heterogeneity. Having base level methylation profiles of the DMRs from the filtered RRBS data allows for the construction of highly sensitive and specific detection assays. These results obtained from the improved MSP designs demonstrate that similar performance specifications can be obtained from the other 106 DMRs with additional design improvements, validation, and testing formats.

TABLE 2b

MSP primers

| Name | Length (nt) | Sequence (5'→3') | GC Content (%) | Tm | Ta | SEQ ID NO: |
|---|---|---|---|---|---|---|
| dll (sense)r | 20 | GTC GAG CGC GTT CGT TGT AC | 60.0 | 58.9 | 65 | 177 |
| dll (sense)r | 22 | GAC CCG AAA AAT AAA TCC CGA A | 40.9 | 53.3 | 65 | 178 |
| dll (antisense)f | 24 | GAT TTT TTT AGT TTG TTC GAC GGC | 37.5 | 53.5 | 65 | 179 |
| dll (antisense)r | 25 | AAA ATT ACT AAA CGC GAA ATC GAC G | 36.0 | 54.4 | 65 | 180 |
| en1 (sense)f | 26 | TAA TGG GAT GAT AAA TGT ATT CGC GG | 38.5 | 55.2 | 65 | 181 |

TABLE 2b-continued

MSP primers

| Name | Length (nt) | Sequence (5'→3') | GC Content (%) | Tm | Ta | SEQ ID NO: |
|---|---|---|---|---|---|---|
| en1 (sense)r | 26 | ACC GCC TAA TCC AAC TCG AAC TCG TA | 50.0 | 61.2 | 65 | 182 |
| en1 (antisense)f | 22 | GGT GTT TTT AAA GGG TCG TCG T | 45.5 | 55.7 | 65 | 183 |
| en1 (antisense)r | 19 | GAC CCG ACT CCT CCA CGT A | 63.2 | 58.4 | 65 | 184 |
| foxp2 (sense)f | 30 | GGA AGT TTA TAG TGG TTT CGG CGG GTA GGC | 53.3 | 63.6 | 60 | 185 |
| foxp2 (sense)r | 22 | GCG AAA AAC GTT CGA ACC CGC G | 59.1 | 61.9 | 60 | 186 |
| grin2d (sense)f | 28 | TGT CGT CGT CGC GTT ATT TTA GTT GTT C | 42.9 | 59.2 | 60 | 187 |
| grin2d (sense)r | 22 | AAC CGC CGT CCA AAC CAT CGT A | 54.6 | 61.3 | 60 | 188 |
| nr5a1 (sense)f | 25 | GAA GAG TTA GGG TTC GGG ACG CGA G | 60.0 | 62.6 | 65 | 189 |
| nr5a1 (sense)r | 25 | AAC GAC CAA ATA AAC GCC GAA CCG A | 48.0 | 61.1 | 65 | 190 |
| nr5a1 (antisense)f | 25 | CGT AGG AGC GAT TAG GTG GGC GTC G | 64.0 | 64.6 | 60 | 191 |
| nr5a1 (antisense)r | 23 | AAA CCA AAA CCC GAA ACG CGA AA | 43.5 | 58.5 | 60 | 192 |
| shh (sense)f | 26 | CGA TTC GGG GGA TGG ATT AGC GTT GT | 53.9 | 62.6 | 65 | 193 |
| shh (sense)r | 30 | CGA AAT CCC CCT AAC GAA AAT CTC CGA AAA | 43.3 | 60.4 | 65 | 194 |
| shh (antisense)f | 25 | CGG GGT TTT TTT AGC GGG GGT TTT C | 52.0 | 61.0 | 65 | 195 |
| shh (antisense)r | 29 | CGC GAT CCG AAA AAT AAA TTA ACG CTA CT | 37.9 | 57.8 | 65 | 196 |
| spsb4 (sense)f | 20 | AGC GGT TCG AGT TGG GAC GG | 65.0 | 62.3 | 65 | 197 |
| spsb4 (sense)r | 24 | GAA AAA CGC GAT CGC CGA AAA CGC | 54.2 | 61.8 | 65 | 198 |
| spsb4 (antisense)f | 28 | GAA GGT TAT TAA TTT AAT AGT CGC GGA A | 32.1 | 53.7 | 65 | 199 |
| spsb4 (antisense)r | 25 | AAA AAA AAC GTT CCC GAC GAC CGC G | 52.0 | 62.4 | 65 | 200 |
| prkcbf (re-design) | 25 | AGT TGT TTT ATA TAT CGG CGT TCG G | 40.0 | 55.3 | 65 | 201 |
| prkcbr (re-design) | 23 | GAC TAT ACA CGC TTA ACC GCG AA | 47.8 | 56.9 | 65 | 202 |

In Table 2b, Ta is the optimized annealing temperature and Tm is the melting temperature in °C. in 50 mM NaCl.

Detection of Other GI Neoplasms

The markers were then assessed in the 2nd set of samples, which included other GI cancers and precancers as indicated above. The methods, including reaction conditions and platform, were identical to the first validation described above. Data were normalized to the amount of input DNA, allowing copy numbers to be compared between the two validations. Analysis consisted of PCA and k-fold cross-validation, as before.

Some methylation sequences that were identified exhibited extraordinary degrees of discrimination, even as stand-alone markers. For example, IKZF1 had 95% sensitivity for adenoma and 80% sensitivity for CRC, with virtually no background methylation in normal samples. The S/N ratios were in excess of 10,000—a degree of discrimination rarely seen with any class of markers. The chr12.133 assay, specific to a completely un-annotated and un-described stretch of methylated DNA, was also adept at detecting all cancers equally well. Several markers (cd1d, chr12.133, clec11a, elmo1, vwc2, zuf71) individually achieved perfect discrimination for gastric cancer, as did twist1 for colorectal cancer (Table 6).

Tumor Site Prediction

The data collected during the development of embodiments of the technology demonstrate that the methylation states of particular DNA markers accurately predict neoplasm site. In this analysis, a recursive partitioning regression model was used in a decision tree analysis based on combinations of markers with complementary performance to generate a robust site classification.

In particular, statistical analyses were performed to validate the sensitivity and specificity of marker combinations. For example, using a "Random Forest" model (see, e.g., Breiman (2001) "Random Forests" *Machine Learning* 45: 5-32), tree models were constructed using recursive partitioning tree regression, e.g., as implemented by the rPart package in the R statistical software. Recursive partitioning tree regression is a regression technique which tries to minimize a loss function and thus maximize information content for classification problems. The tree is built by the following process: first the single variable is found that best splits the data into two groups. The data is separated, and then this process is applied separately to each sub-group, and so on recursively until the subgroups either reach a minimum size or until no improvement can be made. The second stage of the procedure consists of using cross-validation to trim back the full tree. A cross validated estimate of risk is computed for a nested set of sub trees and a final model is produced from the sub tree with the lowest estimate of risk.

See, e.g., Therneau (2012) "An Introduction to Recursive Partitioning Using RPART Routines", available at The Comprehensive R Archive Network; Breiman et al. (1983) "Classification and Regression Trees" Wadsworth, Belmont, Calif.; Clark et al. (1992) "Tree-based models" in J. M. Chambers and T. J. Hastie, eds., *Statistical Models in S*, chapter 9. Wadsworth and Brooks/Cole, Pacific Grove, Calif.; Therneau (1983) "A short introduction to recursive partitioning" Orion Technical Report 21, Stanford University, Department of Statistics; Therneau et al. (1997) "An introduction to recursive partitioning using the rpart routines" Division of Biostatistics 61, Mayo Clinic.

As used in this analysis, the classification is Upper GI Lesion vs. Lower GI Lesion vs. Normal Samples. At each node of the regression, all variables are considered for entry but only the variable with the greatest decrease in risk of predicted outcome is entered. Subsequent nodes are added to the tree until there is no change in risk. To avoid overfitting, random forest regression was used. In this approach, 500 prediction trees were generated using bootstrapping of samples and random selection of variables. To determine the importance of the i-th variable, the i-th variable is set aside and the corresponding error rates for the full fit (including all data) vs. the reduced fit (all data except the i-th variable) using all 500 predictions are compared.

A forest of 500 trees was constructed to test the predictive power of candidate markers for discriminating among normal tissue, upper gastrointestinal lesions, and lower gastrointestinal lesions. This procedure is done at a very high level of robustness. First, for each tree creation, a bootstrap sample is taken of the dataset to create a training set and all observations not selected are used as a validation set. At each branch in the tree, a random subset of markers is used and evaluated to determine the best marker to use at that particular level of the tree. Consequently, all markers have an equal chance of being selected. The technique provides a rigorous validation and assessment of the relative importance of each marker. Each of the 500 trees is allowed to "vote" on which class a particular sample belongs to with the majority vote winning. The estimated misclassification rate is estimated from all samples not used for a particular tree.

To test the relative importance of a given marker, the validation set is again used. Here, once a tree is fit, the validation data is passed down the tree and the correct classification rate is noted. Then, the marker values are randomly permuted within the m-th marker, they are passed down the tree, and the correct classification is again noted. If a marker has high importance, the actual data provides a better classification than the randomly permuted data. Misclassification by the permuted data is referred to as the Mean Decrease in Accuracy. If a marker is not important, the actual data will provide a similar classification as the randomly permuted data. FIG. 1 is a plot of the marker importance as measured by Mean Decrease in Accuracy. The vertical lines are at 2.5% and 5%. These data indicate that, e.g., for clec11a the estimated Mean Decrease in Accuracy is approximately 12%, indicating that when randomly permuting the results of this marker, the overall accuracy of the prediction decreases by 12%. FIG. 1 lists the markers in order of importance.

The estimated overall misclassification rate of the 500 trees in the forest was 0.0989. The results of the voting process across all 500 trees in the forest is summarized in Table 3 and expanded by subtype in Table 4. In the tables, the tissue sample type is listed in the first column (e.g., non-cancerous ("Normal"), upper gastrointestinal cancer ("Upper"), or lower gastrointestinal cancer ("Lower") in Table 3; adenoma ("Ad"), normal colon ("Colo Normal"), colorectal cancer ("CRC"), esophageal cancer ("Eso C"), pancreatic cancer ("Pan C"), normal pancreas ("Pan Normal"), and stomach cancer ("Stomach C") in Table 4). A quantitative classification of the sample by the analysis is provided as a number is columns 1, 2, or 3, for classification as an upper gastrointestinal cancer (column 1), a lower gastrointestinal cancer (column 2), or a normal tissue (column 3), respectively. The numbers provide a measure indicating the success rate of the classifier (e.g., the number of times the classifier classified the sample type in the first column as the type indicated in the first row).

TABLE 3

|  | 1 | 2 | 3 | class.error |
|---|---|---|---|---|
| Upper | 59.00 | 1.00 | 7.00 | 0.12 |
| Lower | 3.00 | 33.00 | 2.00 | 0.13 |
| Normal | 1.00 | 0.00 | 44.00 | 0.02 | column 1 = upper GI;
column 2 = lower GI;
Column 3 = normal

TABLE 4

| | Predicted by Model | | |
|---|---|---|---|
| Sample type | UGIC* | CRN** | Normal |
| UGIC* | | | |
| Pancreas Cancer | 35 | 0 | 3 |
| Esophagus Cancer | 15 | 0 | 3 |
| Stomach Cancer | 9 | 1 | 0 |
| CRN** | | | |
| Colon Cancer | 2 | 16 | 2 |
| Colon Adenoma | 1 | 17 | 0 |
| Controls | | | |
| Pancreas Normal | 0 | 0 | 15 |
| Colon Normal | 0 | 0 | 20 |
| Buffy Coat Normal | 1 | 0 | 9 |

*UGIC = Upper GI Cancer,
**CRN = CRC + Adenoma ≥1 cm

Additional analysis demonstrated that a combination of two markers accurately predicted tumor site in >90% of samples, the top 17 two-marker combinations accurately predicted tumor site in >80% of samples, and the top 49 combinations accurately predicted tumor site in 70% of the samples. This observation that multiple combinations of DNA methylation markers accurately predict tumor site demonstrates the robustness of the technology.

Using the top two markers in the recursive partition decision tree, all normal tissues were correctly classified as normal, all gastric cancers were correctly classified as upper GI, nearly all esophageal and pancreatic cancers were correctly classified as upper GI, and nearly all colorectal cancers and precancers (adenomas) were correctly classified as lower GI. During the development of embodiments of the technology provided herein, statistical analyses focused on a set of specific markers consisting of clec11a, c13orf18, kcnn2, abcb1, slc38a3, cd1c, ikzf1, adcy1, chr12133, rspo3, and twist1. In particular, statistical analyses described above were directed toward identifying sets of markers (e.g., having two or more markers) that provide increased power to identify cancer and/or discriminate between cancers. Table 5 summarizes the accuracy for each pairwise set of markers, namely clec11a, c13orf18, kcnn2, abcb1, slc38a3, cd1c, ikzf1, adcy1, chr12133, rspo3, and twist1. According to this analysis, the pair of markers consisting of clec11a and twist1 is the most informative, but various other combinations have similar accuracy.

TABLE 5

Accuracy for Site Prediction Using Various Marker Combinations

| accuracy | markers |
|---|---|
| 90.7 | clec11a twist1 |
| 88.7 | clec11a chr12.133 |
| 88.7 | clec11a rspo3 |
| 88 | clec11a ikzf1 |
| 86.7 | clec11a adcy1 |
| 84.7 | twist1 c13orf18 |
| 84 | clec11a cd1d |
| 83.3 | twist1 abcb1 |
| 83.3 | c13orf18 chr12.133 |
| 83.3 | abcb1 chr12.133 |
| 83.3 | abcb1 rspo3 |
| 82 | c13orf18 rspo3 |
| 81.3 | abcb1 ikzf1 |
| 80.7 | abcb1 adcy1 |
| 80 | twist1 kcnn2 |
| 80 | c13orf18 adcy1 |
| 80 | cd1d rspo3 |
| 79.3 | c13orf18 cd1d |
| 79.3 | kcnn2 adcy1 |
| 79.3 | kcnn2 rspo3 |
| 79.3 | cd1d ikzf1 |
| 78.7 | c13orf18 ikzf1 |
| 77.3 | kcnn2 ikzf1 |
| 77.3 | abcb1 cd1d |
| 76.7 | twist1 cd1d |
| 76.7 | kcnn2 chr12.133 |
| 76.7 | chr12.133 rspo3 |
| 76 | cd1d chr12.133 |
| 75.3 | twist1 rspo3 |
| 75.3 | kcnn2 cd1d |
| 74.7 | twist1 ikzf1 |
| 74 | twist1 slc38a3 |
| 74 | slc38a3 ikzf1 |
| 74 | slc38a3 chr12.133 |
| 73.3 | twist1 chr12.133 |
| 73.3 | slc38a3 adcy1 |
| 73.3 | adcy1 rspo3 |
| 72.7 | slc38a3 rspo3 |
| 72 | cd1d adcy1 |
| 72 | ikzf1 chr12.133 |
| 72 | adcy1 chr12.133 |
| 71.3 | ikzf1 adcy1 |
| 70.7 | clec11a c13orf18 |
| 70.7 | clec11a kcnn2 |
| 70.7 | clec11a abcb1 |
| 70.7 | clec11a slc38a3 |
| 70.7 | ikzf1 rspo3 |
| 70 | twist1 adcy1 |
| 70 | kcnn2 abcb1 |
| 68 | slc38a3 cd1d |
| 66.7 | c13orf18 abcb1 |
| 65.3 | c13orf18 kcnn2 |
| 65.3 | kcnn2 slc38a3 |
| 64.7 | c13orf18 slc38a3 |
| 56 | abcb1 slc38a3 |

Example 3—AUC Analysis of Individual Markers

Statistical analysis included principle component analysis to identify uncorrelated linear combinations of the markers whose variance explains the greatest percentage of variability observed in the original data. The analysis determined the relative weights of each marker to discriminate between treatment groups. As a result of this analysis, end-point AUC values were determined for a subset of the markers that measure each marker's power to discriminate a specific cancer (esophageal, stomach, pancreatic, colorectal, and adenoma) from 1) the other cancer types and from 2) normal samples (e.g., not comprising cancer tissue or not from a patient having cancer or who may develop cancer). These data are provided in Table 6.

TABLE 6

AUC values for a subset of markers

| | BMP3 | NDRG4 | abcb1 | adcy1 |
|---|---|---|---|---|
| Eso C. vs. Other | 0.51 | 0.58 | 0.67 | 0.39 |
| Eso C. vs. Normal | 0.82 | 0.86 | 0.83 | 0.63 |
| Stomach C. vs. Other | 0.72 | 0.70 | 0.87 | 0.65 |
| Stomach C. vs. Normal | 0.91 | 0.95 | 1.00 | 0.86 |
| Pan C. vs. Other | 0.59 | 0.66 | 0.73 | 0.69 |
| Pan C. vs. Normal | 0.90 | 0.90 | 0.91 | 0.94 |
| CRC. vs. Other | 0.74 | 0.59 | 0.46 | 0.69 |
| CRC. vs. Normal | 0.91 | 0.87 | 0.72 | 0.86 |
| Ad. vs. Other | 0.74 | 0.71 | 0.35 | 0.71 |
| Ad. vs. Normal | 0.96 | 0.94 | 0.61 | 0.99 |
| | c13orf18 | cacna1c | cd1d | chr12.133 |
| Eso C. vs. Other | 0.60 | 0.27 | 0.52 | 0.52 |
| Eso C. vs. Normal | 0.75 | 0.42 | 0.85 | 0.86 |
| Stomach C. vs. Other | 0.78 | 0.70 | 0.75 | 0.81 |
| Stomach C. vs. Normal | 0.88 | 0.96 | 1.00 | 1.00 |
| Pan C. vs. Other | 0.81 | 0.85 | 0.73 | 0.57 |
| Pan C. vs. Normal | 0.89 | 0.96 | 0.94 | 0.86 |
| CRC. vs. Other | 0.37 | 0.56 | 0.67 | 0.73 |
| CRC. vs. Normal | 0.51 | 0.75 | 0.88 | 0.89 |
| Ad. vs. Other | 0.21 | 0.42 | 0.54 | 0.72 |
| Ad. vs. Normal | 0.35 | 0.53 | 0.88 | 0.99 |
| | clec11a | elmo1 | eomes | glc1 |
| Eso C. vs. Other | 0.55 | 0.46 | 0.37 | 0.51 |
| Eso C. vs. Normal | 0.81 | 0.76 | 0.54 | 0.69 |
| Stomach C. vs. Other | 0.84 | 0.76 | 0.70 | 0.74 |
| Stomach C. vs. Normal | 1.00 | 1.00 | 0.89 | 0.88 |
| Pan C. vs. Other | 0.89 | 0.62 | 0.70 | 0.54 |
| Pan C. vs. Normal | 0.98 | 0.93 | 0.87 | 0.73 |
| CRC. vs. Other | 0.31 | 0.71 | 0.61 | 0.64 |
| CRC. vs. Normal | 0.56 | 0.83 | 0.79 | 0.80 |
| Ad. vs. Other | 0.35 | 0.70 | 0.59 | 0.65 |
| Ad. vs. Normal | 0.59 | 0.92 | 0.77 | 0.82 |
| | ihif1 | kcnk12 | kcnn2 | loc63930 |
| Eso C. vs. Other | 0.11 | 0.39 | 0.68 | 0.40 |
| Eso C. vs. Normal | 0.10 | 0.66 | 0.84 | 0.69 |
| Stomach C. vs. Other | 0.80 | 0.65 | 0.76 | 0.65 |
| Stomach C. vs. Normal | 0.98 | 0.90 | 0.91 | 0.88 |
| Pan C. vs. Other | 0.91 | 0.71 | 0.76 | 0.61 |
| Pan C. vs. Normal | 0.97 | 0.94 | 0.91 | 0.88 |
| CRC. vs. Other | 0.50 | 0.71 | 0.46 | 0.84 |
| CRC. vs. Normal | 0.58 | 0.93 | 0.67 | 0.95 |
| Ad. vs. Other | 0.21 | 0.67 | 0.30 | 0.69 |
| Ad. vs. Normal | 0.22 | 0.92 | 0.47 | 0.93 |
| | prkcb | rspo3 | scarf2 | slc38a3 |
| Eso C. vs. Other | 0.44 | 0.42 | 0.13 | 0.34 |
| Eso C. vs. Normal | 0.62 | 0.68 | 0.21 | 0.50 |
| Stomach C. vs. Other | 0.71 | 0.64 | 0.70 | 0.81 |
| Stomach C. vs. Normal | 0.85 | 0.86 | 0.82 | 0.97 |
| Pan C. vs. Other | 0.74 | 0.57 | 0.93 | 0.83 |
| Pan C. vs. Normal | 0.90 | 0.93 | 0.94 | 0.96 |
| CRC. vs. Other | 0.56 | 0.80 | 0.49 | 0.57 |
| CRC. vs. Normal | 0.71 | 0.93 | 0.57 | 0.73 |
| Ad. vs. Other | 0.46 | 0.82 | 0.26 | 0.32 |
| Ad. vs. Normal | 0.66 | 1.00 | 0.34 | 0.47 |
| | twist1 | vwc2 | wt1 | znf71 |
| Eso C. vs. Other | 0.42 | 0.52 | 0.35 | 0.70 |
| Eso C. vs. Normal | 0.74 | 0.83 | 0.66 | 0.90 |
| Stomach C. vs. Other | 0.58 | 0.78 | 0.70 | 0.89 |
| Stomach C. vs. Normal | 0.92 | 1.00 | 0.91 | 1.00 |
| Pan C. vs. Other | 0.67 | 0.58 | 0.76 | 0.50 |

TABLE 6-continued

AUC values for a subset of markers

| | | | | |
|---|---|---|---|---|
| Pan C. vs. Normal | 0.94 | 0.92 | 0.98 | 0.79 |
| CRC. vs. Other | 0.83 | 0.72 | 0.69 | 0.63 |
| CRC. vs. Normal | 1.00 | 0.90 | 0.92 | 0.91 |
| Ad. vs. Other | 0.70 | 0.76 | 0.64 | 0.64 |
| Ad. vs. Normal | 0.95 | 0.98 | 0.89 | 0.90 |

| | st8sia1 | ikzf1 | pcbp3 | PCA1 |
|---|---|---|---|---|
| Eso C. vs. Other | 0.45 | 0.55 | 0.54 | 0.47 |
| Eso C. vs. Normal | 0.64 | 0.88 | 0.86 | 0.79 |
| Stomach C. vs. Other | 0.77 | 0.74 | 0.76 | 0.81 |
| Stomach C. vs. Normal | 0.92 | 0.97 | 0.97 | 0.99 |
| Pan C. vs. Other | 0.65 | 0.49 | 0.64 | 0.72 |
| Pan C. vs. Normal | 0.93 | 0.85 | 0.86 | 0.96 |
| CRC. vs. Other | 0.58 | 0.81 | 0.67 | 0.68 |
| CRC. vs. Normal | 0.74 | 0.94 | 0.90 | 0.96 |
| Ad. vs. Other | 0.67 | 0.80 | 0.63 | 0.62 |
| Ad. vs. Normal | 0.84 | 0.99 | 0.86 | 0.98 |

Example 4—Barrett's Esophagus and Esophageal Cancer

Development of esophageal cancer is closely linked with Barrett's epithelial metaplasia and pancreatic adenocarcinoma arises from discrete mucous cell metaplasias. See, e.g., Biankin et al (2003) "Molecular pathogenesis of precursor lesions of pancreatic ductal adenocarcinoma" *Pathology* 35:14-24; Cameron et al (1995) "Adenocarcinoma of the esophagogastric junction and Barrett's esophagus" *Gastroenterology* 109: 1541-1546.

To meaningfully curb the rising incidence of esophageal adenocarcinoma, effective methods are needed to screen the population for the critical precursor of Barrett's esophagus (BE). Minimally or non-invasive tools have been proposed for BE screening, but have been hampered by lack of optimally sensitive and specific markers. Desired screening markers discriminate BE from normal esophagogastric mucosa. Certain aberrantly methylated genes are associated as candidate markers for BE (see, e.g., *Gastroenterology* 2011; 140: S-222).

Accordingly, during the development of embodiments of the technology experiments were performed to assess the value of selected methylated DNA markers to discriminate BE from adjacent squamous esophagus (SE) and gastric cardia (GC) and from SE and GC in healthy controls.

Patients with and without known BE were recruited prior to routine upper endoscopy. BE cases had >1 cm length of circumferential columnar mucosa with histologically confirmed intestinal metaplasia: controls had no BE as determined endoscopically. Biopsies were obtained in cases from BE, GC (1 cm below Z-line), and SE (>2 cm above BE) cases, and in controls from GC (as for BE) and SE (5 cm above Z-line), and promptly frozen. Biopsy samples were processed as a batch, and assayed in blinded fashion. Following DNA extraction and bisulfite treatment, methylation on target genes was assayed by methylation-specific PCR for the markers APC, HPP1, SFRP1, and by QuARTS assay for the markers BMP3 and NDRG4. ß-actin was quantified as a control marker for total human DNA.

Among 25 BE cases and 22 controls, the median ages were 67 (range 39-83) and 50 (range 20-78), respectively, and men represented 72% and 46% of the subjects in the BE and control groups, respectively. Median BE length was 6 cm (range 2-14 cm). Except for APC, median levels of methylated markers were significantly and substantially (e.g., 200-1100 times) higher in BE than in adjacent SE and GC or relative to normal SE and GC. Sensitivities for BE at various specificities are shown for each marker (Table 7). Methylated markers were significantly higher in GC adjacent to BE than in GC from normal controls. Methylated APC was higher in BE than SE, but did not distinguish BE from GC. In contrast to methylated markers, ß-actin distributions were similar across tissue groups. Marker levels increased with BE length for NDRG4, SFRP1, BMP3, and HPP1 (p=0.01, 0.01, 0.02, and 0.04, respectively). Factors not significantly affecting marker levels included age, sex, inflammation, and presence of dysplasia (none (8), low grade (6), high grade (11)).

As such, these date demonstrate that the selected methylated DNA markers highly discriminate BE from GC and SE, and provide for useful screening applications.

TABLE 7

| Specificity Cutoff* | Sensitivity for BE, % | | | | |
|---|---|---|---|---|---|
| | NDRG4 | SFRP1 | BMP3 | HPP1 | APC |
| 100% | 96 | 96 | 84 | 84 | 0 |
| 95% | 96 | 96 | 92 | 88 | 8 |
| 90% | 96 | 96 | 92 | 92 | 8 |

*Based on combined SE and GC data from normal controls

Example 5—Methylated DNA Markers in Pancreatic Juice Discriminate Pancreatic Cancer from Chronic Pancreatitis and Normal Controls Pancreatic juice analysis has been explored as a minimally-invasive approach to early detection of pancreatic cancer (PC). However, cytology and many molecular markers in pancreatic juice have proved insensitive or failed to distinguish PC from chronic pancreatitis (see, e.g., *J Clin Oncol* 2005; 23: 4524). Experiments were performed to verify that assay of aberrantly methylated genes may represent a more accurate approach for PC detection from pancreatic juice (see, e.g., *Cancer Res* 2006; 66: 1208). In particular, data were collected to assess selected methylated DNA markers assayed from pancreatic juice to discriminate case patients with PC from controls with chronic pancreatitis (CP) or a normal pancreas (NP).

A panel of 110 patients (66 PC, 22 CP, 22 NP controls) underwent secretin stimulated pancreatic juice collection during endoscopic ultrasound. Diagnoses were histologically confirmed for PC and radiographically-based for CP and NP. Juice was promptly frozen and stored at −80° C. Assays were performed in blinded fashion on samples thawed in batch. Candidate methylated DNA markers were selected by whole methylome sequencing in a separate tissue study. After DNA was extracted from pancreatic juice and bisulfite treated, gene methylation was determined by methylation-specific PCR for CD1D, CLEC11A, and KCNN2, or by QuARTS for BMP3 and NDRG4. KRAS mutations (7 total) were assayed by QuARTS (presence of any KRAS mutation was considered to be a positive). ß-actin, a marker for human DNA, was also assayed by QuARTS, to provide for control of DNA amount.

Respectively for PC, CP, and NP, the median age was 67 (range 43-90), 64 (range 44-86), and 60 (range 35-78); men represented 56, 68, and 21% of these groups respectively. All markers discriminated PC from NP but to a variable extent. The AUC was 0.91 (95% CI, 0.85-0.97), 0.85 (0.77-0.94), 0.85 (0.76-0.94), 0.78 (0.67-0.89), and 0.75 (0.64-

0.87) for methylated CD1D, NDRG4, CLEC11A, KCNN2, and BMP3, respectively, and 0.75 (0.64-0.86) for mutant KRAS. Discrimination for PC by CD1D was significantly higher than by KRAS (p=0.01), KCNN2 (p=0.02), or BMP3 (p<0.01). Positivity rates in PC and CP are shown for each marker at 95 and 100% normal specificity cutoffs (Table 8); the positivity rate in CP (false-positives) was lowest with CD1D and highest with KRAS. Marker levels were not significantly affected by PC site (head, body, tail) or stage (N0 vs. N1). ß-actin levels were similar across patient groups.

These data show that methylated DNA markers discriminate PC from CP and NP when assayed from pancreatic juice, e.g., secretin-stimulated pancreatic juice. In particular, methylated CD1D was significantly more sensitive for PC and showed substantially fewer false-positives with CP than did mutant KRAS.

TABLE 8

| | Positivity Rates, % | | | |
|---|---|---|---|---|
| | At 95% Specificity* | | At 100% Specificity* | |
| | PC | CP | PC | CP |
| Methylation Markers | | | | |
| CD1D | 75 | 9 | 63 | 5 |
| NDRG4 | 67 | 14 | 56 | 5 |
| CLEC11A | 56 | 18 | 38 | 5 |
| KCNN2 | 33 | 18 | 33 | 18 |
| BMP3 | 31 | 9 | 23 | 5 |
| Mutation Marker | | | | |
| KRAS | 55 | 41 | 53 | 32 |

*Specificity cutoffs based on NP data

Example 6—Sensitive DNA Marker Panel for Detection of Pancreatic Cancer by Assay in Pancreatic Juice Pancreatic juice analysis represents a minimally-invasive approach to detection of pancreatic cancer (PC) and precancer. It has been found that specific methylated DNA markers in pancreatic juice discriminate PC from chronic pancreatitis (CP) and normal pancreas (Gastroenterology 2013; 144:S-90), but new markers and marker combinations remain unexplored.

Experiments were performed to assess the value of recently discovered methylated DNA markers and mutant KRAS assayed alone and combined in pancreatic juice to discriminate PC from chronic pancreatitis (CP) and reference controls (CON).

167 patients (85 PC, 30 CP, 23 premalignant intraductal mucinous neoplasm (IPMN), 29 CON) who had undergone secretin stimulated pancreatic juice collection during EUS were studied. Diagnoses were histologically based for PC, radiographically for CP, and histologically or radiographically for IPMN. Specificity was based on CON, which included patients with risk factors for PC, elevated pancreatic enzymes, or GI symptoms but radiographically-normal pancreas. Juice samples archived at −80° C. were blindly batch assayed. On DNA extracted from 200 µL pancreatic juice, gene methylation was determined by bisulfite treatment by quantitative allele-specific real-time target and signal amplification (QuARTS) for assay of ADCY1, CD1D, BMP3, PRKCB, KCNK12, C13ORF18, IKZF1, CLEC11A, TWIST1, NDRG4, ELMO, and 55957 Mutant ERAS mutations (7 total) and ß-actin (a marker for total human DNA) were also assayed by QuARTS. From quantitative data, an algorithm was followed to achieve optimal discrimination by a panel combining all markers.

Respectively for PC, CP, IPMN, and CON: median age was 67 (IQR 60-77), 66 (55-77), 66 (60-76) and 70 (62-77); men comprised 52, 53, 49, and 72%. At respective specificity cutoffs of 90% and 95%: the combined marker panel achieved highest PC sensitivities (88% and 77%); ADCY1, the most sensitive single marker, detected 84% and 71%. Other single markers detected PC but to variable extents (table). Overall discrimination by area under ROC curve was higher by panel than by any single marker (p<0.05), except ADCY1 (table). At 90% specificity, panel detected 44% of all IPMNs and 75% (¾) of subset with high grade dysplasia. Positivity rates were substantially lower in CP than in PC for all markers shown in Table 7 (p<0.0001). At 100% specificity, the panel was positive in 58% PC, 17% IPMN, and 13% CP. Accordingly, these results demonstrate that a panel of novel methylated DNA markers and mutant KRAS assayed from pancreatic juice achieves high sensitivity for PC.

TABLE 7

Marker positivity rates in pancreatic juice of patients with pancreatic cancer (PC), intraductal papillary mucinous neoplasm (IPMN), and chronic pancreatitis (CP).

| | | Positivity Rates, % | | | | | |
|---|---|---|---|---|---|---|---|
| | AUC | At 90% Specificity* | | | At 95% Specificity* | | |
| | (PC vs Con) | PC | IPMN | CP | PC | IPMN | CP |
| Methylation Markers** | | | | | | | |
| ADCY1 | 0.89 | 84 | 39 | 30 | 71 | 35 | 17 |
| C13ORF18 | 0.82 | 67 | 17 | 13 | 52 | 13 | 3 |
| PRKCB | 0.82 | 62 | 9 | 20 | 42 | 4 | 17 |
| CD1D | 0.82 | 61 | 22 | 10 | 46 | 17 | 10 |
| KCNK12 | 0.82 | 54 | 17 | 10 | 25 | 13 | 3 |
| BMP3 | 0.81 | 49 | 13 | 7 | 27 | 13 | 0 |
| IKZF1 | 0.80 | 71 | 22 | 20 | 54 | 22 | 17 |
| Mutation Marker | | | | | | | |
| KRAS | 0.80 | 59 | 22 | 13 | 58 | 17 | 10 |
| All Markers | | | | | | | |
| Panel*** | 0.91 | 88 | 44 | 37 | 77 | 39 | 23 |

*Specificity cutoffs based on reference control (CON) data.
**Top 7 individual methylated DNA markers shown.
***Except for ADCY1, the Panel had significantly higher AUC than individual methylated DNA markers (p < 0.05).

Example 7—Detecting Pancreatic Cancer within Stool Sample Using CD1D Marker

Stool samples from 45 individuals having pancreatic cancer and 45 individuals not having pancreatic cancer were collected and tested for the presence of the CD1D marker. Pancreatic cancer was successfully detected using CD1D marker from stool.

Example 8—Novel DNA Methylation Markers Associated with Early-Stage Pancreatic Cancer Study Overview:

In independent case-control tissue studies, experiments were performed to identify novel and highly discriminant methylation markers for PanC using RRBS for the discovery phase and methylation-specific PCR (MSP) for the validation phase.

Study Population:

After approval by the Mayo Clinic Institutional Review Board, tissue samples were identified from existing cancer registries. The accessible population included those who underwent distal pancreatectomy, pancreaticoduodenectomy, colectomy or colon biopsy with a frozen archived specimen. All tissues were reviewed by an expert gastrointestinal pathologist to confirm correct classification. The PanC case samples included pancreatic ductal adenocarcinoma tissues limited to early-stage disease (AJCC stage I and II) (Edge SBB, D. R.; Compton, C. C.; Fritz, A. G.; Greene, F. L.; Trotti, A. (Eds.), editor. AJCC Cancer Staging Manual. 7th ed: Springer, New York; 2010). Neoplasms arising from IPMN lesions were excluded. There were two control groups studied. The first, termed "normal pancreas," included the histologically normal resection margins of low risk (serous cystadenoma) or focal pancreatic neoplasms (neuroendocrine tumors). The second control group included colonic epithelial tissues from patients confirmed to be free from PanC or colonic neoplasm. Cases and both controls were matched by sex, age (in 5-year increments) and smoking status (current or former vs. never). In a central core laboratory, case and control tissues were microdissected and DNA was extracted using a phenol-chloroform technique, yielding at least 500 ng of DNA. Case identification, matching and DNA extraction were performed by independent personnel to maintain blinding of laboratory personnel to case and control status.

Reduced Representation Bisulfite Sequencing:

Library preparation (Gu H, Bock C, Mikkelsen T S, Jager N, Smith Z D, Tomazou E, et al. Genome-scale DNA methylation mapping of clinical samples at single-nucleotide resolution. Nat Methods. 2010; 7:133-6): Genomic DNA (300 ng) was fragmented by digestion with 10 Units of MspI, a methylation-specific restriction enzyme which recognizes CpG containing motifs. This enriches the samples for CpG content and eliminates redundant areas of the genome. Digested fragments were end-repaired and A-tailed with 5 Units of Klenow fragment (3'-5' exo-), and ligated overnight to methylated TruSeq adapters (Illumina, San Diego Calif.) containing one of four barcode sequences (to link each fragment to its sample ID.) Size selection of 160-340 bp fragments (40-220 bp inserts) was performed using Agencourt AMPure XP SPRI beads/buffer (Beckman Coulter, Brea Calif.). Buffer cutoffs were 0.7× to 1.1× sample volumes of beads/buffer. Final elution volume was 22 uL (EB buffer-Qiagen, Germantown Md.) qPCR was used to gauge ligation efficiency and fragment quality on a small aliquot of sample. Samples then underwent bisulfite conversion (twice) using a modified EpiTect protocol (Qiagen). qPCR and conventional PCR (PfuTurbo Cx hotstart-Agilent, Santa Clara Calif.) followed by Bioanalyzer 2100 (Agilent) assessment on converted sample aliquots determined the optimal PCR cycle number prior to amplification of the final library. Conditions for final PCR: 50 uL rxn: 5 uL of 10× buffer, 1.25 uL of 10 mM each dNTP's, 5 uL primer cocktail (~5 uM), 15 uL template (sample), 1 uL PfuTurbo Cx hotstart, 22.75 water. 95C-5 min; 98C-30 sec; 16 cycles of 98C-10 sec, 65C-30 sec, 72C-30 sec; 72C-5 min; 4C. Samples were combined (equimolar) into 4-plex libraries based on the randomization scheme and tested with the bioanalyzer for final size verification, and with qPCR using phiX standards and adaptor-specific primers.

Sequencing and Bioinformatics:

Samples were loaded onto flow cell lanes according to a randomized lane assignment with additional lanes reserved for internal assay controls. Sequencing was performed by the Next Generation Sequencing Core at the Mayo Clinic Medical Genome Facility on the Illumina HiSeq 2000. Reads were unidirectional for 101 cycles. Each flow cell lane generated 100-120 million reads, sufficient for a median coverage of 30-50 fold sequencing depth (read number per CpG) for aligned sequences. Standard Illumina pipeline software was used for base calling and sequence read generation in the fastq format. As described previously (Sun Z, Baheti S, Middha S, Kanwar R, Zhang Y, Li X, et al. SAAP-RRBS: streamlined analysis and annotation pipeline for reduced representation bisulfite sequencing. Bioinformatics. 2012; 28:2180-1), SAAP-RRBS, a streamlined analysis and annotation pipeline for reduced representation bisulfite sequencing, was used for sequence alignment and methylation extraction.

Validation Studies by Methylation-Specific PCR:

Overview: Two MSP-based validation studies were performed on expanded sample sets to confirm the accuracy and reproducibility of the observed differentially methylated candidates. The first, an internal validation study, was performed on unmatched, unblinded samples using biological and technical replicates of PanC and normal colon and technical replicates of normal pancreas. This step was performed to ensure that the sites of differential methylation identified by the RRBS data filtration, where % methylation was the unit of analysis, would be reflected in MSP, where the unit of analysis is the absolute genomic copy number of the target sequence, corrected by the concentration of input DNA for each sample. The second, external validation experiment, utilized MSP to test the top candidates in randomly allocated, matched, blinded, independent PanC, benign pancreas and normal colon samples.

Primer design: Primers for each marker were designed to target the bisulfite-modified methylated sequences of each target gene (IDT, Coralville Iowa) and a region without cytosine-phosphate-guanine sites in the ß-actin gene, as a reference of bisulfite treatment and DNA input. The design was done by either Methprimer software (University of California, San Francisco Calif.) or by semi-manual methods (by H.Z and W.R.T). Assays were then tested and optimized by running qPCR with SYBR Green (Life Technologies, Grand Island N.Y.) dyes on dilutions of universally methylated and unmethylated genomic DNA controls.

Methylation specific PCR: MSP reactions were performed on tissue-extracted DNA as previously described (Kisiel J B, Yab T C, Taylor W R, Chari S T, Petersen G M, Mahoney D W, et al. Stool DNA testing for the detection of pancreatic cancer: assessment of methylation marker candidates. Cancer. 2012; 118:2623-31). Briefly, DNA was bisulfite treated using the EZ DNA Methylation Kit (Zymo Research, Orange, Calif.) and eluted in buffer. One µl bisulfite-treated DNA was used as a template for methylation quantification with a fluorescence-based real-time PCR, performed with SYBR Green master mix (Roche, Mannheim Germany). Reactions were run on Roche 480 LightCyclers (Indianapolis, Ind.), where bisulfite-treated CpGenome Universal Methylated DNA (Millipore, Billerica, Mass.) was used as a positive control, and serially diluted to create standard curves for all plates. Oligonucleotide sequences and annealing temperatures are available upon request.

Statistical Analysis

RRBS: The primary comparison of interest was the methylation difference between cases and pancreatic controls at each mapped CpG. CpG islands are biochemically defined by an observed to expected CpG ratio exceeding 0.6 (Gardiner-Garden M, Frommer M. CpG islands in vertebrate genomes. Journal of molecular biology 1987; 196:261-82). However, for this model, tiled units of CpG analysis "differentially methylated region (DMR)" were created based on the distance between CpG site locations for each chromosome. As the distance between any given CpG exceeded the previous or next location by more than 100 bps, a new island identifier was created. Islands with only a single CpG were excluded. The secondary outcome was the same comparison between cases and colon controls. Individual CpG sites were considered for differential analysis only if the total depth of coverage per disease group was ≥200 reads (roughly equating to an average of 10 reads per subject) and the variance of % methylation was greater than zero (non-informative CpG sites with 0 variance were excluded). The criteria for read depth were based on the desired statistical power to detect a difference of 10% in the methylation rate between any two groups in which the sample size of individuals for each group was 18.

Statistical significance was determined by logistic regression on the % methylation per DMR (using the actual counts) with the groups defined as PanC, normal pancreas, and normal colon. To account for varying read depths across individual subjects, an over-dispersed logistic regression model was used, where dispersion parameter was estimated using the Pearson Chi-square statistic of the residuals from fitted model. To assess strand specific methylation, forward and reverse regions were analyzed separately. The DMRs were then ranked according to their significance level and were considered as a viable marker region if the methylation rate in the controls was ≤1% but ≥10% in PanC. Each significant DMR was considered as a candidate marker.

For the internal validation study, the primary outcome was the area under the receiver operating characteristics curve (AUC) for each marker. This was calculated using logistic regression (JMP version 9.0.1, SAS Institute, Cary N.C.) to model the strength of the concentration-corrected copy number of each marker with PanC in comparison to normal pancreas and normal colon. The markers with the highest AUC values and widest ratio of median genomic copy number between cases and controls were selected for the external validation study. The primary outcome for the external validation experiment was the AUC for each marker plotted against the signal strength of each marker, measured by the log of the ratio of median corrected copy number in cases compared to controls. With eighteen cases there is >80% power to detect an area under the curve of 0.85 or higher from the null hypothesis of 0.5 at a two-sided significance level 0.05. The secondary endpoint was the AUC of two-marker combinations, measured by logistic regression, in which both markers were required to independently associate with PanC cases.

RRBS Marker Discovery

Matched, blinded, randomly allocated DNA extracts from 18 pancreatic cancer tumors, 18 benign pancreatic control tissues and 18 normal colon epithelial tissues were sequenced by RRBS. Median age was 61 (interquartile range 52-65), 61% were women, and 44% were current or former smokers. A total of 6,101,049 CpG sites were captured in any of the samples with at least 10× coverage. After selecting only CpG sites where group coverage and variance criteria were met, a total of 1,217,523 CpG sites were further considered for analysis. Approximately 500 DMRs met significance criteria for differential methylation. Among these, we identified 107 candidate regions with sufficient methylation signatures for MSP primer design. Methylation signatures ranged from 3 neighboring CpGs to 52 CpGs. Methylation levels of the pancreatic cancers rarely exceeded 25% at filtered CpGs, reflecting high levels of contaminating stromal cells. This was confirmed after sequencing each of the cancers for KRAS mutations to verify allele frequencies for the positive samples; for the 50% of PanC specimens which harbored a heterozygous KRAS base change, the frequency of the mutant allele was at least 4 times less than the corresponding wild-type allele.

Internal Validation

Based on the number of neighboring CpGs in each candidate gene methylation signature, primers were designed for 87 of the 107 candidate markers. MSP was then used to assay the candidates in sample of DNA from an additional 20 unblinded PanC lesions, 10 additional normal colonic epithelial samples (biologic replicates) as well as, remaining DNA samples from the 18 sequenced PanC lesions, 15 of the sequenced benign pancreatic tissues and 10 of the sequenced normal colon samples (technical replicates). With first-pass primer designs, 74 of 87 markers successfully amplified. With re-design, the remaining 13 primers successfully amplified and were tested in 12 unblinded PanC samples and 10 normal colon samples. ß-actin amplified in all samples. With either first or second-pass MSP, 31 of 87 candidate markers had an AUC>0.85. Based on the magnitude of difference in median genomic copy number between cases and controls for each candidate marker, 23 were selected for external validation in independent samples. These were ABCB1, ADCY1, BMP3, C13ORF18, CACNA1C, CD1D, CHR12:133484978-133485738 (CHR12 133), CLEC11A, ELMO1, FOXP2, GRIN2D, IKZF1, KCNK12, KCNN2, NDRG4, PRKCB, RSPO3, SCARF2, SHH, SLC38A3, TWIST1, VWC3 and WT1.

External Validation

Matched, blinded, randomly allocated DNA from 18 PanC, 18 benign pancreatic and 36 normal colon epithelial samples were assayed by MSP for the 23 top candidates. The median age of this subset was 60 (interquartile range 54-64). The majority (55%) of samples came from men and 61% were current or former smokers. ß-actin amplified in all samples. 9 of 23 candidates showed excellent association with PanC. The individual AUC values for CACNA1C, CHR12.133, WT1, GRIN2D, ELMO1, TWIST1, C13ORF18, KCNN2, and CLEC11A were 0.95, 0.95, 0.94, 0.94, 0.93, 0.92, 0.91, 0.90 and 0.90, respectively. Good association was seen with 9 other candidates; the AUC values for PRKCB, CD1D, SLC38A3, ABCB1, KCNK12, VWC2, RSPO3, SHH and ADCY1 were 0.89, 0.88, 0.86, 0.86, 0.86, 0.85, 0.85, 0.85 and 0.84 respectively.

The log ratio of the median case and control values for each marker was plotted against the AUC. Eight markers, SHH, KCNK12, PRKCB, CLEC11, C13ORF18, TWIST1, ELMO1 and CHR12.133 each had an AUC greater than 0.85, and showed greater than 1.5 log (>30-fold) greater genomic copy number among cases than controls. KCNK12, PRKCB, ELMO1 and CHR12.133 showed greater than 2 log (>100-fold) difference.

Complementarity Analysis

Among all 231 possible 2-marker combinations, both markers remained highly significant in 30 (13%) pair-wise models of association with PanC. Of those, 18 (8%) showed improvement of the AUC. Noteworthy among several complementary markers, C13ORF18 improved the accuracy of CACNA1C, WT1, GRIND2D, SLC38A3 and SCARF2 with AUCs of 0.99, 0.99, 0.97, 0.96, and 0.95, respectively, for each combination. Though the AUC for SHH as an individual marker was 0.85, it improved the performance of 6 other markers when paired. The AUC of CACNA1C, WT1, SLC38A3, ABCB1, VWC2 and RSPO3 improved to 0.96, 0.95, 0.92, 0.98, 0.88 and 0.95, respectively when combined in models with SHH. Of the 18 most robust marker combinations, 9 combinations could be tested in pair-wise comparisons from the internal validation data set. Of these, 7 pairs (78%) remained highly significant in both data sets.

Example 9—Highly Discriminant Methylated DNA Markers for Detection of Barrett's Esophagus To curb the rising incidence of esophageal adenocarcinoma, effective methods are needed to screen the population for the critical precursor-Barrett's esophagus (BE). Minimally or non-invasive tools have been proposed but hampered by lack of optimally sensitive and specific markers. Experiments were performed and aberrantly methylated BMP3 and NDRG4 were identified as discriminant candidate markers for BE.

An aim of such experiments was to prospectively assess the accuracy of methylated BMP3 and NDRG4 to identify BE using endoscopic biopsies (Phase 1) and brushings from the whole esophagus and cardia to simulate non-endoscopic sampling devices (Phase 2).

Cases with and controls without BE were recruited prior to endoscopy. BE cases had >1 cm of circumferential columnar mucosa with confirmed intestinal metaplasia; controls had no BE endoscopically. In Phase 1, biopsies were obtained in cases from BE, gastric cardia ((GC); 1 cm below Z-line) and squamous epithelium ((SE); >2 cm above BE) and in controls from GC (as for BE) and SE (5 cm above Z-line); then promptly frozen. Biopsy samples were processed as a batch, and assayed in blinded fashion. In Phase 2, specimens were obtained using a high capacity endoscopic cytology brush (Hobbs Medical, Stafford Springs Conn.); the cardia, BE (in cases), and full esophageal length were brushed to simulate a swallowed sponge sampling device. Following DNA extraction and bisulfite treatment, methylation on target genes was assayed by quantitative allele-specific real-time target and signal amplification. ß-actin was also quantified as a marker for total human DNA.

Figure 2:
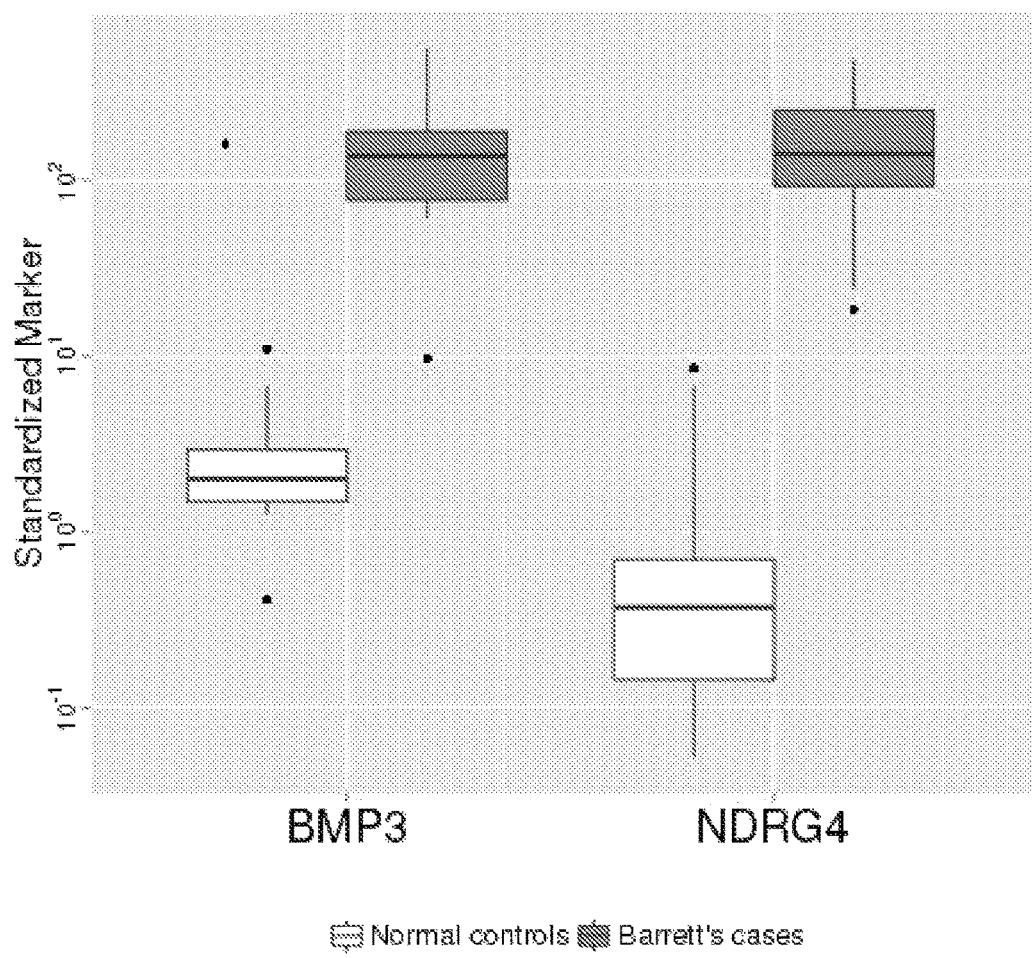
FIG. 2 shows marker levels of BMP3 and NDRG4 in brushings (cardia+whole esophagus) in Barrett's cases and controls as described in Example 8.

100 subjects were prospectively studied. Phase 1: Among 40 BE cases and 40 controls: median age was 65 (quartiles 55-77) and 54 (37-69) and men comprised 78% and 48%, respectively. Median BE length was 6 cm (range 3-10). Median levels of methylated markers were substantially higher (34-600 times) in BE than in adjacent SE and GC or than in normal SE and GC (Table). In contrast to methylated markers, ß-actin distributions were similar across tissue groups. Both marker levels increased with BE length and age, p<0.001 whereas only NDRG4 increased significantly with presence of dysplasia (none (19), low grade (9), high grade (11); p=0.003). Factors not significantly affecting marker levels included sex and inflammation. Phase 2: Among 10 BE cases and 10 controls, median age was 64 (59-70) and 66 (49, 71) and men comprised 80 and 30% respectively. Median BE length was 2 cm (range 1-4). Discrimination of BE by markers was extraordinary with AUC of 1.0 for NDRG4 and 0.99 for BMP3; levels were >100 times higher in cases than controls (FIG. 2).

These experiments demonstrate that selected methylated DNA markers highly discriminate BE from normal GC and SE, both in biopsy and brushed specimens. Table 9 shows the function and cancer biology associations of the selected methylated DNA markers.

TABLE 8

Marker levels (copy numbers of markers adjusted for beta actin) for BMP3 and NDRG4 biopsies from BE cases (cardia, Barrett's, squamous) and controls (cardia, squamous).

| | BMP3 | | NDRG4 | |
|---|---|---|---|---|
| | Normal controls | Barrett's cases | Normal controls | Barrett's cases |
| Squamous | 0.8 | 5.6 | 1.0 | 4.9 |
| Q1, Q3 | 0.3, 2.2 | 0.7, 14.8 | 0.5, 2.7 | 1.5, 10.9 |
| P90, P95 | 7.0, 23.0 | 25.5, 50.3 | 5.0, 13.7 | 32.0, 64.1 |
| BE | | 300.2 | | 390.6 |
| Q1, Q3 | | 137.1, 659.5 | | 146.6, 763.5 |
| P90, P95 | | 1083.1, 1219.0 | | 921.8, 1006.6 |
| Cardia | 0.5 | 8.2 | 2.3 | 11.5 |
| Q1, Q3 | 0.3, 1.9 | 2.8, 40.3 | 1.0, 6.3 | 5.0, 48.3 |
| P90, P95 | 10.3, 16.4 | 190.7, 431.5 | 13.1, 15.4 | 116.7, 345.0 |
| Composite | 1.3 | 131.4 | 2.3 | 136.5 |
| Q1, Q3 | 0.4, 3.8 | 67.1, 242.7 | 1.1, 5.3 | 68.9, 272.3 |
| P90, P95 | 10.0, 15.3 | 402.9, 417.9 | 8.1, 12.5 | 344.0, 383.3 |
| Pvalue | <0.0001 | | <0.0001 | |

TABLE 9

Function and cancer biology associations of top candidate markers

| DMR | Symbol | Gene name | Protein Function | Cancer association | Reference (complete reference below table) |
|---|---|---|---|---|---|
| Chr7: 87229775-87229856 | ABCB1 | ATP-binding cassette, sub-family B, member 1 | Membrane-associated transporter protein | Multi-drug resistance to chemotherapy | Lee, et al. 2013 |
| Chr7: 45613877-45614564 | ADCY1 | Adenylate cyclase 1 | Transmembrane signalling | Methylation associated with pancreatic cancer | Vincent, et al. 2011 |
| Chr13: 46960770-46961464 | C13ORF18 | KIAA0226-like | Uncharacterized | Methylation associated with pancreatic cancer, cervical neoplasia | Vincent, et al. 2011; Van, et al. 2009 |

TABLE 9-continued

Function and cancer biology associations of top candidate markers

| DMR | Symbol | Gene name | Protein Function | Cancer association | Reference (complete reference below table) |
|---|---|---|---|---|---|
| Chr12: 2800665-2800898 | CACNA1C | Calcium channel, voltage-dependent, L type, alpha 1C subunit | Mediates cellular calcium ion influx | Methylation associated with pancreatic cancer | Vincent, et al. 2011 |
| Chr1: 158150797-158151142 | CD1D | CD1D molecule | Transmembrane glycoprotein mediating presentation of antigens to T cells | Target for novel immunotherapy-based cancer treatment; expressed by medulloblastoma | Liu, et al. |
| Chr19: 51228217-51228703 | CLEC11 | C-type lectin-11 | C-type lectin domain, uncharacterized | None | — |
| Chr12: 133484978-133485738 | (Chr12- 133) | — | Uncharacterized | — | — |
| Chr7: 37487539-37488498 | ELMO1 | Engulfment and cell motility 1 | Interaction with cytokinesis proteins, promotion of cell motility and phagocytosis | Promotion of metastatic spread | Li, et al. |
| Chr7: 113727624-113727693 | FOXP2 | Forkhead box P2 | Transcription factor, expressed in brain, lung, gut | Expressed in subsets of prostate cancer, lymphoma and multiple myeloma | Stumm, et al., Campbell, et al. |
| Chr19: 48946755-48946912 | GRIN2D | Glutamate receptor, ionotropic, N-methyl D-aspartate 2D | NMDA receptor, neurotransmission | Methylation associated with pancreatic cancer, mutant in breast cancer | Vincent, et al. 2011, Jiao, et al. |
| Chr7: 50343848-50343927 | IKZF1 | IKAROS family zinc finger 1 | DNA binding protein associated with chromatin remodeling | Mutant in leukemias | Asai, et al. |
| Chr2: 47797332-47797371 | KCNK12 | Potassium channel, sub-family K, member 12 | Non-functioning potassium channel | Methylation associated with pancreatic and colon cancer | Vincent, et al. 2011, Kober, et al. |
| Chr5: 113696984-113697057 | KCNN2 | Potassium intermediate/small conductance calcium-activated channel, subfamily N, member 2 | Potassium channel, voltage-gated, calcium activated | Overexpressed in prostate cancer | Camões, et al. |
| Chr16: 58497395-58497458 | NDRG4 | N-myc downregulated gene, family member 4 | Cytosolic signalling protein required for cell cycle progression | Methylated in pancreatic, colon cancer | Kisiel, et al., Ahlquist, et al. |
| Chr16: 23846964-23848004 | PRKCB | Protein kinase C, beta | Serine- and threonine specific kinase involved in cell signalling | Methylation associated with pancreatic cancer, druggable target in Ewing sarcoma | Vincent, et al. 2011, Surdez, et al. |
| Chr6: 127440526-127441039 | RSPO3 | R-spondin, type 3 | Regulatory protein in Wnt/β-catenin signalling pathway | Methylation associated with pancreatic cancer, elevated expression in colon cancers | Vincent, et al. 2011, Seshigiri, et al. |

TABLE 9-continued

Function and cancer biology associations of top candidate markers

| DMR | Symbol | Gene name | Protein Function | Cancer association | Reference (complete reference below table) |
|---|---|---|---|---|---|
| Chr22: 20785373-20785464 | SCARF2 | Scavenger receptor class F, member 2 | Mediates binding and degradation of low density lipoproteins | Methylation associated with pancreatic cancer, methylation and reduced expression in gastric cancer | Vincent, et al. 2011, Zhao, et al. |
| Chr7: 155597771-155597951 | SHH | Sonic hedgehog | Embryogenesis | Methylation associated with pancreatic cancer, epigenetically repressed in MEN1 syndrome; hedgehog signalling mediates pancreatic cancer invasion | Vincent, et al. 2011, Gurung, et al. |
| Chr3: 50243467-50243553 | SLC38A3 | Solute carrier, family 38, member 3 | Uncharacterized | Decreased expression in lung cancer | Person, et al. |
| Chr7: 19156788-19157093 | TWIST1 | Twist basic helix-loop-helix transcription factor 1 | Transcription factor expressed in placental and mesodermal tissue | Methylation associated with pancreatic cancer, biliary cancer, urothelial cancer | Vincent, et al. 2011, Shin, et al. |
| Chr7: 49813182-49814168 | VWC2 | von Willebrand factor C domain containing 2 | Secreted bone morphogenic protein antagonist | Methylation associated with pancreatic cancer | Vincent, et al. 2011 |
| Chr11: 32460759-32460800 | WT1 | Wilms tumor 1 | Zinc finger motif transcription factor | Methylation associated with pancreatic, prostate, ovarian and breast cancers | Vincent, et al. 2011, Jacobs, et al. |

Lee W K, Chakraborty P K, Thevenod F. Pituitary homeobox 2 (PITX2) protects renal cancer cell lines against doxorubicin toxicity by transcriptional activation of the multidrug transporter ABCB1. International journal of cancer Journal international du cancer. 2013; 133:556-67.

Vincent A, Omura N, Hong S M, Jaffe A, Eshleman J, Goggins M. Genome-wide analysis of promoter methylation associated with gene expression profile in pancreatic adenocarcinoma. Clinical cancer research: an official journal of the American Association for Cancer Research. 2011; 17:4341-54.

Yang N, Eijsink J J, Lendvai A, Volders H H, Klip H, Buikema H J, et al. Methylation markers for CCNA1 and C13ORF18 are strongly associated with high-grade cervical intraepithelial neoplasia and cervical cancer in cervical scrapings. Cancer epidemiology, biomarkers & prevention: a publication of the American Association for Cancer Research, cosponsored by the American Society of Preventive Oncology. 2009; 18:3000-7.

Liu D, Song L, Brawley V S, Robison N, Wei J, Gao X, et al. Medulloblastoma expresses CD1d and can be targeted for immunotherapy with NKT cells. Clin Immunol. 2013; 149:55-64. Li H, Yang L, Fu H, Yan J, Wang Y, Guo H, et al. Association between Galphai2 and ELMO1/Dock180 connects chemokine signalling with Rac activation and metastasis. Nat Commun. 2013; 4:1706.

Stumm L, Burkhardt L, Steurer S, Simon R, Adam M, Becker A, et al. Strong expression of the neuronal transcription factor FOXP2 is linked to an increased risk of early PSA recurrence in ERG fusion-negative cancers. Journal of clinical pathology. 2013; 66:563-8.

Campbell A J, Lyne L, Brown P J, Launchbury R J, Bignone P, Chi J, et al. Aberrant expression of the neuronal transcription factor FOXP2 in neoplastic plasma cells. British journal of haematology. 2010; 149:221-30.

Jiao X, Wood L D, Lindman M, Jones S, Buckhaults P, Polyak K, et al. Somatic mutations in the Notch, NF-KB, PIK3CA, and Hedgehog pathways in human breast cancers. Genes, chromosomes & cancer. 2012; 51:480-9.

Asai D, Imamura T, Suenobu S, Saito A, Hasegawa D, Deguchi T, et al. IKZF1 deletion is associated with a poor outcome in pediatric B-cell precursor acute lymphoblastic leukemia in Japan. Cancer Med. 2013; 2:412-9.

Kober P, Bujko M, Oledzki J, Tysarowski A, Siedlecki J A. Methyl-CpG binding column-based identification of nine genes hypermethylated in colorectal cancer. Molecular carcinogenesis. 2011; 50:846-56.

Camoes M J, Paulo P, Ribeiro F R, Barros-Silva J D, Almeida M, Costa V L, et al. Potential downstream target genes of aberrant ETS transcription factors are differentially affected in Ewing's sarcoma and prostate carcinoma. PLoS ONE. 2012; 7:e49819.

Kisiel J B, Yab T C, Taylor W R, Chari S T, Petersen G M, Mahoney D W, et al. Stool DNA testing for the detection of pancreatic cancer: assessment of methylation marker candidates. Cancer. 2012; 118:2623-31.

Ahlquist D A, Zou H, Domanico M, Mahoney D W, Yab T C, Taylor W R, et al. Next-Generation Stool DNA Test Accurately Detects Colorectal Cancer and Large Adenomas. Gastroenterology. 2012; 142:248-56.

Surdez D, Benetkiewicz M, Perrin V, Han Z Y, Pierron G, Ballet S, et al. Targeting the EWSR1-FLI1 oncogene-induced protein kinase PKC-beta abolishes ewing sarcoma growth. Cancer research. 2012; 72:4494-503.

Seshagiri S, Stawiski E W, Durinck S, Modrusan Z, Storm E E, Conboy C B, et al. Recurrent R-spondin fusions in colon cancer. Nature. 2012; 488:660-4.

Zhao J, Liang Q, Cheung K F, Kang W, Lung R W, Tong J H, et al. Genome-wide identification of Epstein-Barr virus-driven promoter methylation profiles of human genes in gastric cancer cells. Cancer. 2013; 119:304-12.

Gurung B, Feng Z, Iwamoto D V, Thiel A, Jin G, Fan C M, et al. Menin epigenetically represses Hedgehog signaling in MEN1 tumor syndrome. Cancer research. 2013; 73:2650-8.

Person R J, Tokar E J, Xu Y, Orihuela R, Ngalame N N, Waalkes M P. Chronic cadmium exposure in vitro induces cancer cell characteristics in human lung cells. Toxicol Appl Pharmacol. 2013.

Shin S H, Lee K, Kim B H, Cho N Y, Jang J Y, Kim Y T, et al. Bile-based detection of extrahepatic cholangiocarcinoma with quantitative DNA methylation markers and its high sensitivity. The Journal of molecular diagnostics: JMD. 2012; 14:256-63.

Jacobs D I, Mao Y, Fu A, Kelly W K, Zhu Y. Dysregulated methylation at imprinted genes in prostate tumor tissue detected by methylation microarray. BMC Urol. 2013; 13:37.

Example 9—a Stool-Based microRNA and DNA Marker Panel for the Detection of Pancreatic Cancer Given the extraordinary lethality of pancreatic cancer (PC), practical non-invasive methods for pre-symptomatic screen detection are needed. MicroRNAs (miRNAs) have altered expression in PC.

Experiments were performed with having an aim to explore the feasibility of stool miR-1290 for detection of PC.

Archival stool samples from 58 PC cases and 64 healthy controls matched on age, gender, and smoking history were analyzed. Detection of miRNA was performed by a stem-loop quantitative reverse transcription polymerase chain reaction (qRT-PCR) approach. Quantitation of miRNA was based on measuring the absolute copies per nanogram of extracted RNA. DNA markers (methylated BMP3, mutant KRAS and β-actin) were hybrid captured and amplified as described (Cancer 2012, 118:2623). A step-wise logistic regression model, limited to 5 variables, was used to build an optimized marker panel based on miR-1290, DNA markers, and age. The age adjusted areas under the ROC curve (AUCs) for each of the models were compared using the methods of DeLong et al. The association of miR-1290 with clinical factors was assessed using the Wilcoxon Rank Sums test.

Figure 3:
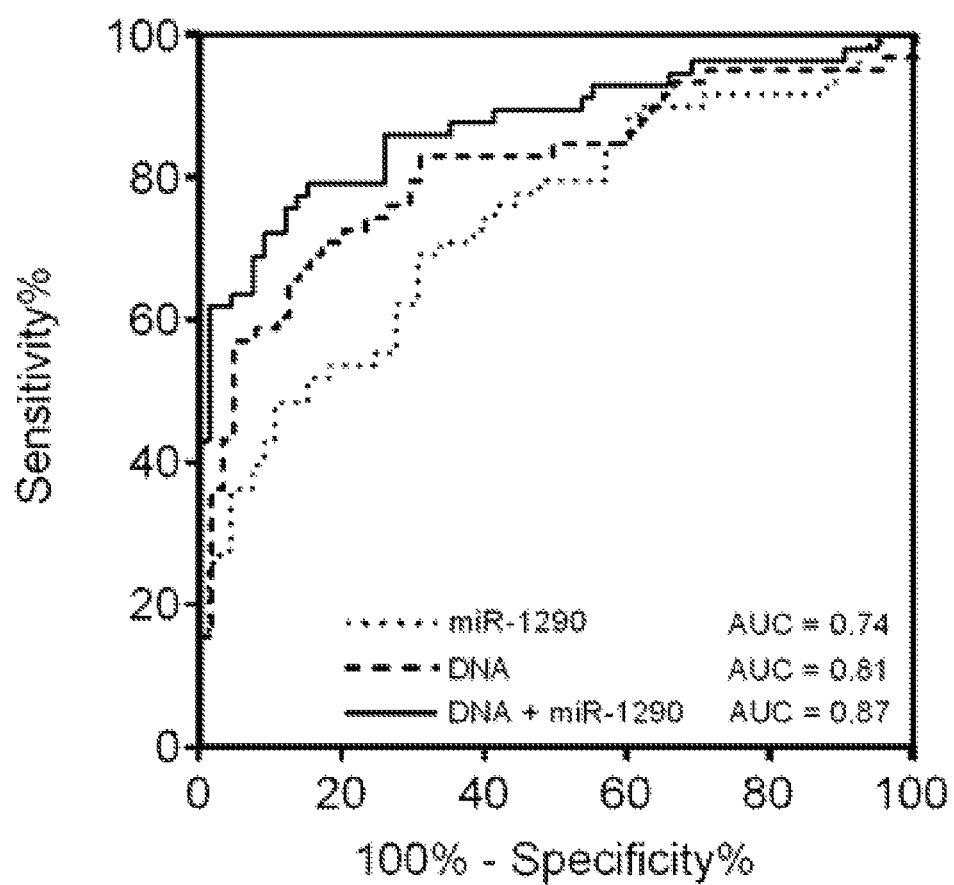
FIG. 3 shows AUC of stool miR-1290 as described in Example 9.

Distributions of miR-1290 were significantly higher in stools from PC cases than from controls (P=0.0002). Stool miR-1290 levels were not affected by age, sex, tumor site or tumor stage. AUC of stool miR-1290 was 0.74 (95% CI: 0.65-0.82, FIG. 3) for PC detection compared to an AUC of 0.81 (0.73-0.89) by the stool DNA marker panel. The addition of miR-1290 to DNA markers proved incremental (P=0.0007) with an AUC of 0.87 (0.81-0.94). Adding miR-1290 to the DNA panel increased the sensitivity of the test across the entire range of specificities including the critical region of 90-100%. PC sensitivity of the combined marker panel was 64% (50%-76%) at 95% (87%-99%) specificity, and 79% (67%-89%) at 85% (74%-92%) specificity.

These experiments identified stool miR-1290 as a marker for PC.

Example 11—Identifying Markers Using RRBS

During the development of the technology provided herein, data were collected from a case-control study to demonstrate that a genome-wide search strategy identifies novel and informative markers.

Study Population, Specimen Acquisition, and Samples

The target population was patients with pancreas cancer seen at the Mayo Clinic. The accessible population includes those who have undergone a distal pancreatectomy, a pancreaticoduodenectomy, or a colectomy with an archived resection specimen and a confirmed pathologic diagnosis. Colonic epithelial DNA was previously extracted from micro-dissected specimens by the Biospecimens Accessioning Processing (BAP) lab using a phenol-chloroform protocol. Data on the matching variables for these samples were used by Pancreas SPORE personnel to select tissue registry samples. These were reviewed by an expert pathologist to confirm case and control status and exclude case neoplasms arising from IPMN, which may have different underlying biology. SPORE personnel arranged for BAP lab microdissection and DNA extraction of the pancreatic case and control samples and provided 500 ng of DNA to lab personnel who were blinded to case and control status. Archival nucleic acid samples included 18 pancreatic adenocarcinomas, 18 normal pancreas, and 18 normal colonic epithelia matched on sex, age, and smoking status.

The sample types were:
1) Mayo Clinic Pancreas SPORE registry PanC tissues limited to AJCC stage I and II;
2) control pancreata free from PanC;
3) archived control colonic epithelium free from PanC; and
4) colonic neoplasm from which DNA had been extracted and stored in the BAP lab.

Cases and controls were matched by sex, age (in 5-year increments), and smoking status (current or former vs. never).

Methods

Libraries were prepared according to previously reported methods (see, e.g., Gu et al (2011) "Preparation of reduced representation bisulfite sequencing libraries for genome-scale DNA methylation profiling" Nature Protocols 6: 468-81) by fragmenting genomic DNA (300 ng) by digestion with 10 units of MspI, a methylation-specific restriction enzyme that recognizes CpG containing motifs. This treatment enriches the samples for CpG content and eliminates redundant areas of the genome. Digested fragments were end-repaired and A-tailed with 5 units of Klenow fragment (3'-5' exo) and ligated overnight to Illumina adapters containing one of four barcode sequences to link each fragment to its sample ID. Size selection of 160-340 bp fragments (having 40-220 bp inserts) was performed using SPRI beads/buffer (AMPure XP, Beckman Coulter). Buffer cutoffs were from 0.7× to 1.1× of the sample volume of beads/ buffer. Samples were eluted in a volume of 22 µl (EB buffer, Qiagen). qPCR was used to gauge ligation efficiency and fragment quality on a small aliquot of sample. Samples then underwent two rounds of bisulfite conversion using a modified EpiTect protocol (Qiagen). qPCR and conventional PCR (Pfu Turbo Cx hotstart, Agilent), followed by Bioanalyzer 2100 (Agilent) assessment on converted sample aliquots, determined the optimal PCR cycle number prior to amplification of the final library. The final PCR was performed in a volume of 50 µl (5 µl of 10×PCR buffer; 1.25 µl of each dNTP at 10 mM; 5 µl of a primer cocktail at approximately 5 µM, 15 µl of template (sample), 1 µl PfuTurbo Cx hotstart, and 22.75 µl water. Thermal cycling began with initial incubations at 95° C. for 5 minutes and at 98° C. for 30 seconds followed by 16 cycles of 98° C. for 10 seconds, 65° C. for 30 seconds, and at 72° C. for 30 seconds. After cycling, the samples were incubated at 72° C. for 5 minutes and kept at 4° C. until further workup and analysis. Samples were combined in equimolar amounts into 4-plex libraries based on a randomization scheme and tested with the bioanalyzer for final size verification. Samples were also tested with qPCR using phiX standards and adaptor-specific primers.

For sequencing, samples were loaded onto flow cell lanes according to a randomized lane assignment with additional lanes reserved for internal assay controls. Sequencing was performed by the NGS Core at Mayo's Medical Genome Facility on the Illumina HiSeq 2000. Reads were unidirectional for 101 cycles. Each flow cell lane generated 100-120 million reads, sufficient for a median coverage of 30× to 50× sequencing depth (based on read number per CpG) for aligned sequences. Standard Illumina pipeline software was used to analyze the reads in combination with RRBSMAP (Xi, et al. (2012) "RRBSMAP: a fast, accurate and user-friendly alignment tool for reduced representation bisulfite sequencing" *Bioinformatics* 28: 430-432) and an in-house pipeline (SAAP-RRBS) developed by Mayo Biomedical and Statistics personnel (Sun et al. (2012) "SAAP-RRBS: streamlined analysis and annotation pipeline for reduced representation bisulfite sequencing" *Bioinformatics* 28: 2180-1). The bioinformatic analyses consisted of 1) sequence read assessment and clean-up, 2) alignment to reference genome, 3) methylation status extraction, and 4) CpG reporting and annotation.

Statistical Considerations:
The primary comparison of interest is methylation differences between cases and disease controls at each CpG and/or tiled CpG window. The secondary outcome is the same comparison between cases and normal buffy coat and colon controls. Markers were tested for differential methylation by:
1. Assessing the distributions of methylation percentage for each marker and discarding markers with more than 2.5% methylated background in colon controls and normal buffy coat
2. Testing the distribution of methylation of remaining markers between cases and controls using the Wilcoxon rank sum test and ranking markers by p-values.
3. Using Q-values to estimate the False Discovery Rates (FDR) (Benjamini et al. (1995) "Multiple Testing" *Journal of the Royal Statistical Society. Series B (Methodological)* 57: 289-300; Storey et al. (2003) "Statistical significance for genomewide studies" *Proc Natl Acad Sci USA* 100: 9440-5). At the discovery-level, an FDR up to 25% is acceptable.

Analysis of Data
A data analysis pipeline was developed in the R statistical analysis software package ("R: A Language and Environment for Statistical Computing" (2012), R Foundation for Statistical Computing). The workflow comprised the following steps:
1. Read in all CpG sites
2. Considered only those CpG sites where the total group depth of coverage was 200 reads or more. This is based on the power assessment to detect a difference between 20% and 30% methylation between any two groups; anything less has little chance of significance. So, if there are 18 subjects per group and each subject has 12 reads, the group depth of coverage is 12*18=216.
3. Excluded all the CpG sites where the variance of the % methylation across the groups was 0 (non-informative CpG sites).
4. Performed an over-dispersed logistic regression on the % methylation (using the actual counts) with the groups defined as Normal Colon/Buffy coat, disease specific control, and specific cancer of interest (cases) to determine the statistical significance of the % methylation for the primary and secondary analyses. An over-dispersed logistic model was used since the variability in the % methylation between subjects is larger than what the binomial assumption allows. This dispersion parameter was estimated using the Pearson Chi-square of the fit.
5. Generated area under the Receiver Operating Characteristic curve (ROC) values. Area under the ROC curve is a measure of predictive accuracy of subject specific % methylation and was estimated for the primary analysis (cases vs. disease control) and the secondary analysis (cases vs. normal colon/buffy coat), separately.
6. In a similar fashion to #5, the fold-change (FC, a measure of the separation between cases and controls) for the primary and secondary analysis was also estimated using the ratio of mean % methylation between cases and corresponding control group.
7. 4-6 above was conducted on individual CpG sites as well as methylated CpG regions. These regions were defined for each chromosome as a group of at least 5 CpG sites within roughly 100 base pairs (bps) distance with a mean % methylation<2.5% in normal colon/buffy coat controls
8. CpG regions showing promise for technical and biological validation were identified as having a statistical significant methylation difference, a large FC, and a high AUC for either the primary or secondary analyses.

Post-R Analysis:
1. Sorted individual CpGs and CpG regions by p-value, FC, and AUC. Cut-offs were <0.01, >20, and >0.85 respectively, although these were often adjusted depending on the robustness of the data. For example, highly heterogeneous neoplastic tissue results in lower % methylation values, which in turn affects the filtering. Primary and secondary comparisons can be sorted together or separately depending on the specificity requirements of the application. Normal colonic epithelia are included as a control for uncovering markers suitable for stool assay. If pancreatic juice is being tested, colonic tissue is unnecessary. This can result in a completely different set of markers.
2. Ranked marker regions based on assay platform requirements. Currently, methylation-specific PCR (MSP), or similar amplification platforms where discrimination is based on the specificity of primer annealing, is the platform of choice. For this methodology, it is imperative to have 2-5 discriminate CpGs per oligo within an amplifiable stretch of DNA. For stool assays, this requirement is even more stringent in that amplicons must be short (<100 bp). Marker selection, therefore, needs to made on the basis of short contiguous stretches of highly discriminate CpGs. If the platform evolves to a sequence-based technology, the CpG distribution requirements within a region may be entirely different.

Results

Matched, blinded, randomly allocated DNA extracts from 18 pancreatic cancer tumors, 18 benign pancreatic control tissues and 18 normal colonic epithelial tissues were sequenced by RRBS. Median age was 61 (interquartile range 52-65), 61% were women, and 44% were current or former smokers. Roughly 6 million CpGs were mapped at ≥10× coverage. More than 2000 CpG regions met significance criteria for differential methylation. After applying the filter criteria above, 449 differentially methylated regions (DMR) were identified (Table 10). Table 11 presents the identified 449 differentially methylated regions (DMR) ranked by decreasing area under the ROC curve (AUC).

In these markers, methylation signatures range from 3 neighboring CpGs to 56 CpGs. Methylation levels of the pancreatic cancers rarely exceeded 25% at filtered CpGs, which suggested that the cancer tissues may have high levels of contaminating normal cells and/or stroma. To test this, each of the cancers was sequenced for KRAS mutations to verify allele frequencies for the positive samples. For the 50% that harbored a heterozygous KRAS base change, the frequency of the mutant allele was at least 4 times less than the corresponding wild-type allele, in support of contamination by normal cells and/or stroma.

It was found that 58 of the 449 markers are in nonannotated regions and lie in genomic regions without protein coding elements. Of the remaining 391 candidate markers, approximately 225 have been described as associated with cancer, some of which classify as tumor suppressors. The 166 other candidate markers have a previously identified weak association with cancer (e.g., mutations and/or copy number alterations observed in genome-wide screens) or have no previously identified cancer associations.

TABLE 10

DMR

| Marker # | Chromosome | Chromosome Coordinates | Annotation |
|---|---|---|---|
| 1 | chr7 | 87229775-87229856 | ABCB1 |
| 2 | chr2 | 207307687-207307794 | ADAM23 |
| 3 | chr15 | 100881373-100881437 | ADAMTS17 |
| 4 | chr16 | 77468655-77468742 | ADAMTS18 |
| 5 | chr19 | 41224781-41225006 | ADCK4 |
| 6 | chr7 | 45613877-45614572 | ADCY1 |
| 7 | chr2 | 70994498-70994755 | ADD2 |
| 8 | chr14 | 105190863-105191031 | ADSSL1 |
| 9 | chr10 | 116064516-116064600 | AFAP1L2 |
| 10 | chr4 | 87934353-87934488 | AFF1 |
| 11 | chr2 | 100720494-100720679 | AFF3 |
| 12 | chr7 | 100136884-100137350 | AGFG2 |
| 13 | chr9 | 116151083-116151315 | ALAD |
| 14 | chr14 | 103396870-103396920 | AMN |
| 15 | chr19 | 10206736-10206757 | ANGPTL6 |
| 16 | chr19 | 17438929-17438974 | ANO8 |
| 17 | chr15 | 90358267-90358400 | ANPEP |
| 18 | chr15 | 29131299-29131369 | APBA2 |
| 19 | chr19 | 45430362-45430458 | APOC1P1 |
| 20 | chr13 | 111767862-111768355 | ARHGEF7 |
| 21 | chr7 | 98990897-98990989 | ARPC1B |
| 22 | chr22 | 51066374-51066431 | ARSA |
| 23 | chr9 | 120175665-120176057 | ASTN2 |
| 24 | chr1 | 203619509-203619829 | ATP2B4 |
| 25 | chr7 | 69062853-69062972 | AUTS2 |
| 26 | chr8 | 104152963-104152974 | BAALC |
| 27 | chr11 | 64052053-64052132 | BAD |
| 28 | chr10 | 121411207-121411375 | BAG3 |
| 29 | chr7 | 98029116-98029383 | BAIAP2L1 |
| 30 | chr9 | 135462730-135462765 | BARHL1 |
| 31 | chr10 | 133795124-133795423 | BNIP3 |
| 32 | chr12 | 107715014-107715095 | BTBD11 |
| 33 | chr6 | 105584524-105584800 | BVES |
| 34 | chr10 | 21816267-21816490 | C10orf140 |
| 35 | chr12 | 21680381-21680438 | C12orf39 |
| 36 | chr12 | 21680681-21680817 | C12orf39 |
| 37 | chr12 | 117174873-117175030 | C12orf49 |
| 38 | chr13 | 46960767-46961669 | C13orf18 |
| 39 | chr14 | 50099743-50099930 | C14orf104 |
| 40 | chr19 | 16772631-16772712 | C19orf42 |
| 41 | chr20 | 31061389-31061649 | C20orf112 |
| 42 | chr5 | 175665232-175665311 | C5orf25 |
| 43 | chr6 | 42858890-42859092 | C6orf226 |
| 44 | chr9 | 139735581-139735683 | C9orf172 |
| 45 | chr12 | 2800756-2800899 | CACNA1C |
| 46 | chr3 | 54156904-54156987 | CACNA2D3 |
| 47 | chr11 | 115373179-115373281 | CADM1 |
| 48 | chr16 | 89007413-89007432 | CBFA2T3 |
| 49 | chr16 | 49316205-49316258 | CBLN1 |

TABLE 10-continued

| Marker # | Chromosome | Chromosome Coordinates | Annotation |
|---|---|---|---|
| | | DMR | |
| 50 | chr21 | 44495919-44495933 | CBS |
| 51 | chr17 | 77810085-77810206 | CBX4 |
| 52 | chr17 | 8649567-8649665 | CCDC42 |
| 53 | chr11 | 64110001-64110069 | CCDC88B |
| 54 | chr14 | 91883473-91883674 | CCDC88C |
| 55 | chr14 | 99946756-99946806 | CCNK |
| 56 | chr1 | 158150797-158151205 | CD1D |
| 57 | chr5 | 175969660-175969699 | CDHR2 |
| 58 | chr7 | 39989959-39990020 | CDK13 |
| 59 | chr16 | 80837397-80837505 | CDYL2 |
| 60 | chr10 | 11059508-11060151 | CELF2 |
| 61 | chr22 | 47130339-47130459 | CERK |
| 62 | chr2 | 233389020-233389049 | CHRND |
| 63 | chr7 | 73245708-73245798 | CLDN4 |
| 64 | chr19 | 51228217-51228732 | CLEC11A |
| 65 | chr3 | 139654045-139654132 | CLSTN2 |
| 66 | chr7 | 155302557-155302639 | CNPY1 |
| 67 | chr6 | 88875699-88875763 | CNR1 |
| 68 | chr6 | 88876367-88876445 | CNR1 |
| 69 | chr6 | 88876701-88876726 | CNR1 |
| 70 | chr2 | 165698520-165698578 | COBLL1 |
| 71 | chr6 | 75794978-75795024 | COL12A1 |
| 72 | chr12 | 48398051-48398093 | COL2A1 |
| 73 | chr12 | 48398306-48398375 | COL2A1 |
| 74 | chr18 | 449695-449798 | COLEC12 |
| 75 | chr7 | 30721980-30722020 | CRHR2 |
| 76 | chr16 | 84875643-84875772 | CRISPLD2 |
| 77 | chr7 | 151127086-151127195 | CRYGN |
| 78 | chr10 | 126812450-126812653 | CTBP2 |
| 79 | chr20 | 56089440-56089547 | CTCFL |
| 80 | chr2 | 219261190-219261327 | CTDSP1 |
| 81 | chr2 | 80530326-80530374 | CTNNA2 |
| 82 | chr22 | 43044555-43044737 | CYB5R3 |
| 83 | chr19 | 1406516-1406625 | DAZAP1 |
| 84 | chr7 | 44084171-44084235 | DBNL |
| 85 | chr11 | 20178177-20178304 | DBX1 |
| 86 | chr4 | 151000325-151000356 | DCLK2 |
| 87 | chr4 | 151000358-151000403 | DCLK2 |
| 88 | chr4 | 183817058-183817157 | DCTD |
| 89 | chr13 | 52378159-52378202 | DHRS12 |
| 90 | chr8 | 13014567-13014682 | DLC1 |
| 91 | chr11 | 84432067-84432186 | DLG2 |
| 92 | chr6 | 170598276-170598782 | DLL1 |
| 93 | chr19 | 39989824-39989852 | DLL3 |
| 94 | chr19 | 12996198-12996321 | DNASE2 |
| 95 | chr2 | 230578698-230578802 | DNER |
| 96 | chr2 | 225907414-225907537 | DOCK10 |
| 97 | chr18 | 32073971-32074004 | DTNA |
| 98 | chr2 | 233352345-233352605 | ECEL1 |
| 99 | chr7 | 37487539-37488596 | ELMO1 |
| 100 | chr20 | 39995010-39995051 | EMILIN3 |
| 101 | chr19 | 48833763-48833967 | EMP3 |
| 102 | chr2 | 119607676-119607765 | EN1 |
| 103 | chr3 | 27763358-27763617 | EOMES |
| 104 | chr3 | 27763909-27763981 | EOMES |
| 105 | chr12 | 132435207-132435428 | EP400 |
| 106 | chr19 | 16473958-16474095 | EPS15L1 |
| 107 | chr6 | 152129293-152129450 | ESR1 |
| 108 | chr3 | 185825887-185826002 | ETV5 |
| 109 | chr9 | 140201493-140201583 | EXD3 |
| 110 | chr6 | 133562127-133562229 | EYA4 |
| 111 | chr1 | 160983607-160983768 | F11R |
| 112 | chr20 | 821836-821871 | FAM110A |
| 113 | chr22 | 45898798-45898888 | FBLN1 |
| 114 | chr9 | 97401449-97401602 | FBP1 |
| 115 | chr16 | 750679-750715 | FBXL16 |
| 116 | chr5 | 15500208-15500399 | FBXL7 |
| 117 | chr5 | 15500663-15500852 | FBXL7 |
| 118 | chr5 | 114880375-114880442 | FEM1C |
| 119 | chr20 | 34189488-34189693 | FER1L4 |
| 120 | chr14 | 53417493-53417618 | FERMT2 |
| 121 | chr2 | 219849962-219850042 | FEV |
| 122 | chr17 | 7339280-7339492 | FGF11 |
| 123 | chr19 | 49256413-49256451 | FGF21 |
| 124 | chr10 | 103538848-103539033 | FGF8 |
| 125 | chr11 | 64008415-64008495 | FKBP2 |

TABLE 10-continued

| Marker # | Chromosome | Chromosome Coordinates | Annotation |
|---|---|---|---|
| 126 | chr11 | 128564106-128564209 | FLI1 |
| 127 | chr10 | 102985059-102985130 | FLJ41350 |
| 128 | chr13 | 28674451-28674629 | FLT3 |
| 129 | chr1 | 240255240-240255264 | FMN2 |
| 130 | chr5 | 131132146-131132232 | FNIP1 |
| 131 | chr6 | 108882636-108882682 | FOXO3 |
| 132 | chr3 | 71478053-71478206 | FOXP1 |
| 133 | chr7 | 113724864-113725006 | FOXP2 |
| 134 | chr7 | 113727624-113727693 | FOXP2 |
| 135 | chr5 | 160975098-160975142 | GABRB2 |
| 136 | chr12 | 51786085-51786218 | GALNT6 |
| 137 | chr5 | 179780839-179780955 | GFPT2 |
| 138 | chr20 | 3641457-3641537 | GFRA4 |
| 139 | chr17 | 4462834-4463034 | GGT6 |
| 140 | chr17 | 4463796-4464037 | GGT6 |
| 141 | chr17 | 42907549-42907807 | GJC1 |
| 142 | chr8 | 144358251-144358266 | GLI4 |
| 143 | chr16 | 4377510-4377615 | GLIS2 |
| 144 | chr12 | 56881329-56881414 | GLS2 |
| 145 | chr6 | 24776486-24776667 | GMNN |
| 146 | chr19 | 3095019-3095055 | GNA11 |
| 147 | chr22 | 19710910-19710984 | GP1BB |
| 148 | chr22 | 19711364-19711385 | GP1BB |
| 149 | chr2 | 131485151-131485219 | GPR148 |
| 150 | chr2 | 165477564-165477609 | GRB14 |
| 151 | chr2 | 165477839-165477886 | GRB14 |
| 152 | chr17 | 73390467-73390597 | GRB2 |
| 153 | chr19 | 48918266-48918311 | GRIN2D |
| 154 | chr19 | 48946755-48946912 | GRIN2D |
| 155 | chr13 | 114018369-114018421 | GRTP1 |
| 156 | chr12 | 13254503-13254606 | GSG1 |
| 157 | chr7 | 43152309-43152375 | HECW1 |
| 158 | chr7 | 139440133-139440341 | HIPK2 |
| 159 | chr6 | 34205664-34206018 | HMGA1 |
| 160 | chr12 | 121416542-121416670 | HNF1A |
| 161 | chr20 | 42984244-42984427 | HNF4A |
| 162 | chr20 | 43040031-43040119 | HNF4A |
| 163 | chr5 | 177632203-177632260 | HNRNPAB |
| 164 | chr7 | 27136030-27136245 | HOXA1 |
| 165 | chr2 | 176971915-176971968 | HOXD11 |
| 166 | chr19 | 35540057-35540200 | HPN |
| 167 | chr2 | 163174366-163174659 | IFIH1 |
| 168 | chr17 | 47073421-47073440 | IGF2BP1 |
| 169 | chr11 | 133797643-133797789 | IGSF9B |
| 170 | chr7 | 50343838-50344029 | IKZF1 |
| 171 | chr7 | 50344414-50344453 | IKZF1 |
| 172 | chr20 | 20345123-20345150 | INSM1 |
| 173 | chr20 | 20350520-20350532 | INSM1 |
| 174 | chr15 | 76632356-76632462 | ISL2 |
| 175 | chr2 | 182321880-182322022 | ITGA4 |
| 176 | chr2 | 182322168-182322198 | ITGA4 |
| 177 | chr2 | 173293542-173293644 | ITGA6 |
| 178 | chr19 | 2097386-2097437 | IZUMO4 |
| 179 | chr21 | 27011846-27011964 | JAM2 |
| 180 | chr2 | 47797260-47797371 | KCNK12 |
| 181 | chr10 | 79397895-79397945 | KCNMA1 |
| 182 | chr5 | 113696524-113696682 | KCNN2 |
| 183 | chr5 | 113696971-113697058 | KCNN2 |
| 184 | chr1 | 154733071-154733232 | KCNN3 |
| 185 | chr8 | 99439457-99439482 | KCNS2 |
| 186 | chr19 | 34287890-34287972 | KCTD15 |
| 187 | chr12 | 121905558-121905792 | KDM2B |
| 188 | chr8 | 136469529-136469873 | KHDRBS3 |
| 189 | chr16 | 85646495-85646594 | KIAA0182 |
| 190 | chr18 | 46190841-46190970 | KIAA0427 |
| 191 | chr4 | 37245694-37245718 | KIAA1239 |
| 192 | chr17 | 72350351-72350403 | KIF19 |
| 193 | chr2 | 149633039-149633137 | KIF5C |
| 194 | chr22 | 50987245-50987312 | KLHDC7B |
| 195 | chr12 | 53298237-53298384 | KRT8 |
| 196 | chr19 | 54974004-54974086 | LENG9 |
| 197 | chr1 | 180198528-180198542 | LHX4 |
| 198 | chr19 | 2290471-2290541 | LINGO3 |
| 199 | chr11 | 19733958-19734013 | LOC100126784 |
| 200 | chr19 | 58513829-58513851 | LOC100128398 |
| 201 | chr17 | 43324999-43325188 | LOC100133991 |

TABLE 10-continued

| Marker # | Chromosome | Chromosome Coordinates | Annotation |
|---|---|---|---|
| | | DMR | |
| 202 | chr17 | 43325784-43325960 | LOC100133991 |
| 203 | chr2 | 109745715-109745742 | LOC100287216 |
| 204 | chr1 | 178063099-178063167 | LOC100302401 |
| 205 | chr12 | 53447992-53448072 | LOC283335 |
| 206 | chr1 | 45769962-45770141 | LOC400752 |
| 207 | chr20 | 61637950-61638000 | LOC63930 |
| 208 | chr13 | 88323571-88323647 | LOC642345 |
| 209 | chr6 | 111873064-111873162 | LOC643749 |
| 210 | chr5 | 87956937-87956996 | LOC645323 |
| 211 | chr5 | 87970260-87970568 | LOC645323 |
| 212 | chr5 | 87970751-87970850 | LOC645323 |
| 213 | chr12 | 85430135-85430175 | LRRIQ1 |
| 214 | chr19 | 497878-497933 | MADCAM1 |
| 215 | chr5 | 71404528-71404563 | MAP1B |
| 216 | chr2 | 39665069-39665282 | MAP4K3 |
| 217 | chr1 | 156406057-156406118 | MAX.chr1.156406057-156406118 |
| 218 | chr1 | 23894874-23894919 | MAX.chr1.23894874-23894919 |
| 219 | chr1 | 240161479-240161546 | MAX.chr1.240161479-240161546 |
| 220 | chr1 | 244012804-244012986 | MAX.chr1.244012804-244012986 |
| 221 | chr1 | 35394690-35394876 | MAX.chr1.35394690-35394876 |
| 222 | chr1 | 35395179-35395201 | MAX.chr1.35395179-35395201 |
| 223 | chr1 | 39044345-39044354 | MAX.chr1.39044345-39044354 |
| 224 | chr10 | 101282185-101282257 | MAX.chr10.101282185-101282257 |
| 225 | chr10 | 127033272-127033428 | MAX.chr10.127033272-127033428 |
| 226 | chr11 | 120382450-120382498 | MAX.chr11.120382450-120382498 |
| 227 | chr11 | 47421719-47421776 | MAX.chr11.47421719-47421776 |
| 228 | chr12 | 133484978-133485066 | MAX.chr12.133484978-133485066 |
| 229 | chr12 | 133485702-133485739 | MAX.chr12.133485702-133485739 |
| 230 | chr12 | 54151078-54151153 | MAX.chr12.54151078-54151153 |
| 231 | chr12 | 58259413-58259475 | MAX.chr12.58259413-58259475 |
| 232 | chr13 | 25322044-25322165 | MAX.chr13.25322044-25322165 |
| 233 | chr13 | 29394692-29394771 | MAX.chr13.29394692-29394771 |
| 234 | chr14 | 100751586-100751695 | MAX.chr14.100751586-100751695 |
| 235 | chr14 | 61123624-61123707 | MAX.chr14.61123624-61123707 |
| 236 | chr14 | 89507100-89507162 | MAX.chr14.89507100-89507162 |
| 237 | chr15 | 40361431-40361644 | MAX.chr15.40361431-40361644 |
| 238 | chr15 | 89942904-89943197 | MAX.chr15.89942904-89943197 |
| 239 | chr16 | 25042924-25043187 | MAX.chr16.25042924-25043187 |
| 240 | chr16 | 85230248-85230405 | MAX.chr16.85230248-85230405 |
| 241 | chr17 | 1835463-1835690 | MAX.chr17.1835463-1835690 |
| 242 | chr17 | 60218266-60218449 | MAX.chr17.60218266-60218449 |
| 243 | chr17 | 76337726-76337824 | MAX.chr17.76337726-76337824 |
| 244 | chr19 | 11805543-11805639 | MAX.chr19.11805543-11805639 |
| 245 | chr19 | 22034747-22034887 | MAX.chr19.22034747-22034887 |
| 246 | chr19 | 32715650-32715707 | MAX.chr19.32715650-32715707 |
| 247 | chr19 | 5805881-5805968 | MAX.chr19.5805881-5805968 |
| 248 | chr2 | 127783183-127783233 | MAX.chr2.127783183-127783233 |
| 249 | chr2 | 232530964-232531124 | MAX.chr2.232530964-232531124 |
| 250 | chr2 | 239957125-239957163 | MAX.chr2.239957125-239957163 |
| 251 | chr2 | 43153331-43153424 | MAX.chr2.43153331-43153424 |
| 252 | chr2 | 71503632-71503860 | MAX.chr2.71503632-71503860 |
| 253 | chr20 | 43948422-43948484 | MAX.chr20.43948422-43948484 |
| 254 | chr21 | 47063798-47063877 | MAX.chr21.47063798-47063877 |
| 255 | chr22 | 17849540-17849622 | MAX.chr22.17849540-17849622 |
| 256 | chr22 | 38732124-38732211 | MAX.chr22.38732124-38732211 |
| 257 | chr22 | 42764974-42765049 | MAX.chr22.42764974-42765049 |
| 258 | chr22 | 46974925-46975007 | MAX.chr22.46974925-46975007 |
| 259 | chr22 | 50342922-50343232 | MAX.chr22.50342922-50343232 |
| 260 | chr3 | 132273353-132273532 | MAX.chr3.132273353-132273532 |
| 261 | chr3 | 193858771-193858843 | MAX.chr3.193858771-193858843 |
| 262 | chr3 | 24563009-24563117 | MAX.chr3.24563009-24563117 |
| 263 | chr3 | 75411368-75411473 | MAX.chr3.75411368-75411473 |
| 264 | chr4 | 26828422-26828522 | MAX.chr4.26828422-26828522 |
| 265 | chr4 | 8965831-8965868 | MAX.chr4.8965831-8965868 |
| 266 | chr5 | 142100518-142100780 | MAX.chr5.142100518-142100780 |
| 267 | chr6 | 169613138-169613249 | MAX.chr6.169613138-169613249 |
| 268 | chr6 | 64168133-64168268 | MAX.chr6.64168133-64168268 |
| 269 | chr7 | 129794337-129794536 | MAX.chr7.129794337-129794536 |
| 270 | chr7 | 1705957-1706065 | MAX.chr7.1705957-1706065 |
| 271 | chr7 | 28893550-28893569 | MAX.chr7.28893550-28893569 |
| 272 | chr7 | 47650711-47650882 | MAX.chr7.47650711-47650882 |
| 273 | chr7 | 64408106-64408135 | MAX.chr7.64408106-64408135 |
| 274 | chr9 | 108418404-108418453 | MAX.chr9.108418404-108418453 |
| 275 | chr9 | 120507310-120507354 | MAX.chr9.120507310-120507354 |
| 276 | chr5 | 89769002-89769411 | MBLAC2 |
| 277 | chr12 | 51319165-51319319 | METTL7A |

TABLE 10-continued

| | | DMR | |
|---|---|---|---|
| Marker # | Chromosome | Chromosome Coordinates | Annotation |
| 278 | chr2 | 191272534-191272765 | MFSD6 |
| 279 | chr19 | 6236947-6237089 | MLLT1 |
| 280 | chr6 | 168333306-168333467 | MLLT4 |
| 281 | chr8 | 89339567-89339662 | MMP16 |
| 282 | chr17 | 2300399-2300476 | MNT |
| 283 | chr7 | 156802460-156802490 | MNX1 |
| 284 | chr19 | 4343896-4242968 | MPND |
| 285 | chr16 | 56715756-56716025 | MT1X |
| 286 | chr15 | 48470062-48470503 | MYEF2 |
| 287 | chr15 | 48470606-48470725 | MYEF2 |
| 288 | chr5 | 16936010-16936058 | MYO10 |
| 289 | chr3 | 39851068-39851989 | MYRIP |
| 290 | chr13 | 33001061-33001251 | N4BP2L1 |
| 291 | chr4 | 2060477-2060624 | NAT8L |
| 292 | chr12 | 125002129-125002192 | NCOR2 |
| 293 | chr16 | 23607524-23607650 | NDUFAB1 |
| 294 | chr10 | 105338596-105338843 | NEURL |
| 295 | chr1 | 204797773-204797785 | NFASC |
| 296 | chr2 | 233877877-233878027 | NGEF |
| 297 | chr18 | 31803017-31803114 | NOL4 |
| 298 | chr9 | 139438534-139438629 | NOTCH1 |
| 299 | chr5 | 32714270-32714325 | NPR3 |
| 300 | chr9 | 127266951-127267032 | NR5A1 |
| 301 | chr11 | 124615979-124616029 | NRGN |
| 302 | chr11 | 124616860-124617005 | NRGN |
| 303 | chr20 | 327754-327871 | NRSN2 |
| 304 | chr8 | 99952501-99952533 | OSR2 |
| 305 | chr5 | 76926598-76926703 | OTP |
| 306 | chr3 | 8809858-8809865 | OXTR |
| 307 | chr19 | 14172823-14172948 | PALM3 |
| 308 | chr6 | 52268531-52268702 | PAQR8 |
| 309 | chr20 | 21686466-21686563 | PAX1 |
| 310 | chr21 | 47063793-47064177 | PCBP3 |
| 311 | chr7 | 100203461-100203600 | PCOLCE |
| 312 | chr4 | 657555-657666 | PDE6B |
| 313 | chr7 | 544848-545022 | PDGFA |
| 314 | chr2 | 239194812-239194946 | PER2 |
| 315 | chr19 | 43979400-43979435 | PHLDB3 |
| 316 | chr6 | 144384503-144385539 | PLAGL1 |
| 317 | chr2 | 28844174-28844270 | PLB1 |
| 318 | chr1 | 242687719-242687746 | PLD5 |
| 319 | chr12 | 6419210-6419489 | PLEKHG6 |
| 320 | chr22 | 50745629-50745727 | PLXNB2 |
| 321 | chr2 | 105471752-105471787 | POU3F3 |
| 322 | chr13 | 79177868-79177951 | POU4F1 |
| 323 | chr1 | 203044913-203044929 | PPFIA4 |
| 324 | chr22 | 50825886-50825981 | PPP6R2 |
| 325 | chr17 | 74519328-74519457 | PRCD |
| 326 | chr7 | 601162-601552 | PRKAR1B |
| 327 | chr16 | 23846964-23847339 | PRKCB |
| 328 | chr16 | 23847507-23847617 | PRKCB |
| 329 | chr16 | 23847825-23848168 | PRKCB |
| 330 | chr22 | 18923785-18923823 | PRODH |
| 331 | chr22 | 45099093-45099304 | PRR5 |
| 332 | chr3 | 9988302-9988499 | PRRT3 |
| 333 | chr1 | 11538685-11538738 | PTCHD2 |
| 334 | chr1 | 11539396-11539540 | PTCHD2 |
| 335 | chr10 | 23480864-23480913 | PTF1A |
| 336 | chr19 | 5340273-5340743 | PTPRS |
| 337 | chr2 | 1747034-1747126 | PXDN |
| 338 | chr2 | 1748338-1748444 | PXDN |
| 339 | chr7 | 4923056-4923107 | RADIL |
| 340 | chr19 | 15568448-15568639 | RASAL3 |
| 341 | chr5 | 80256215-80256313 | RASGRF2 |
| 342 | chr17 | 77179784-77179887 | RBFOX3 |
| 343 | chr4 | 40516823-40516984 | RBM47 |
| 344 | chr4 | 57775698-57775771 | REST |
| 345 | chr10 | 43572798-43572896 | RET |
| 346 | chr10 | 121302439-121302501 | RGS10 |
| 347 | chr16 | 318717-318893 | RGS11 |
| 348 | chr1 | 241520322-241520334 | RGS7 |
| 349 | chr1 | 42846119-42846174 | RIMKLA |
| 350 | chr21 | 43189031-43189229 | RIPK4 |
| 351 | chr7 | 5821188-5821283 | RNF216 |
| 352 | chr19 | 23941063-23941142 | RPSAP58 |
| 353 | chr19 | 23941384-23941670 | RPSAP58 |

TABLE 10-continued

| Marker # | Chromosome | Chromosome Coordinates | Annotation |
|---|---|---|---|
| 354 | chr16 | 29118636-29118891 | RRN3P2 |
| 355 | chr6 | 127440492-127441039 | RSPO3 |
| 356 | chr17 | 42392669-42392701 | RUNDC3A |
| 357 | chr6 | 45345446-45345595 | RUNX2 |
| 358 | chr6 | 45387405-45387456 | RUNX2 |
| 359 | chr3 | 72496092-72496361 | RYBP |
| 360 | chr22 | 20785373-20785464 | SCARF2 |
| 361 | chr8 | 145561664-145561696 | SCRT1 |
| 362 | chr7 | 54826636-54826706 | SEC61G |
| 363 | chr10 | 38691448-38691521 | SEPT7L |
| 364 | chr4 | 154712157-154712232 | SFRP2 |
| 365 | chr7 | 155597793-155597973 | SHH |
| 366 | chr4 | 77610781-77610824 | SHROOM3 |
| 367 | chr21 | 38120336-38120558 | SIM2 |
| 368 | chr15 | 68115602-68115675 | SKOR1 |
| 369 | chr17 | 6949717-6949778 | SLC16A11 |
| 370 | chr11 | 35441199-35441260 | SLC1A2 |
| 371 | chr19 | 59025337-59025385 | SLC27A5 |
| 372 | chr2 | 27486089-27486170 | SLC30A3 |
| 373 | chr12 | 69140018-69140206 | SLC35E3 |
| 374 | chr12 | 46661132-46661306 | SLC38A1 |
| 375 | chr3 | 50243467-50243553 | SLC38A3 |
| 376 | chr7 | 150760388-150760530 | SLC4A2 |
| 377 | chr5 | 1445384-1445473 | SLC6A3 |
| 378 | chr2 | 40679298-40679326 | SLC8A1 |
| 379 | chr5 | 506178-506343 | SLC9A3 |
| 380 | chr20 | 61284095-61284194 | SLCO4A1 |
| 381 | chr5 | 101631546-101631731 | SLCO4C1 |
| 382 | chr10 | 98945242-98945493 | SLIT1 |
| 383 | chr13 | 88330094-88330355 | SLITRK5 |
| 384 | chr15 | 66999854-67000014 | SMAD6 |
| 385 | chr10 | 112064230-112064280 | SMNDC1 |
| 386 | chr6 | 84419007-84419072 | SNAP91 |
| 387 | chr17 | 36508733-36508891 | SOCS7 |
| 388 | chr4 | 7367687-7367825 | SORCS2 |
| 389 | chr17 | 70116754-70116823 | SOX9 |
| 390 | chr4 | 57687746-57687764 | SPINK2 |
| 391 | chr3 | 140770014-140770193 | SPSB4 |
| 392 | chr17 | 36762706-36762763 | SRCIN1 |
| 393 | chr6 | 43141954-43142058 | SRF |
| 394 | chr7 | 105029460-105029585 | SRPK2 |
| 395 | chr16 | 70415312-70415673 | ST3GAL2 |
| 396 | chr2 | 107502978-107503055 | ST6GAL2 |
| 397 | chr2 | 107503155-107503391 | ST6GAL2 |
| 398 | chr12 | 22487528-22487848 | ST8SIA1 |
| 399 | chr10 | 17496177-17496310 | ST8SIA6 |
| 400 | chr2 | 242447608-242447724 | STK25 |
| 401 | chr3 | 120626999-120627116 | STXBP5L |
| 402 | chr3 | 33260338-33260423 | SUSD5 |
| 403 | chr16 | 19179713-19179744 | SYT17 |
| 404 | chr12 | 115122614-115122632 | TBX3 |
| 405 | chr19 | 3606372-3606418 | TBXA2R |
| 406 | chr10 | 70359250-70359439 | TET1 |
| 407 | chr16 | 4310204-4310233 | TFAP4 |
| 408 | chr21 | 32930371-32930409 | TIAM1 |
| 409 | chr4 | 942190-942382 | TMEM175 |
| 410 | chr6 | 130686773-130686820 | TMEM200a |
| 411 | chr6 | 130687200-130687735 | TMEM200a |
| 412 | chr3 | 185215700-185215782 | TMEM41A |
| 413 | chr20 | 42544780-42544835 | TOX2 |
| 414 | chr9 | 140091343-140091644 | TPRN |
| 415 | chr8 | 126441476-126441519 | TRIB1 |
| 416 | chr5 | 14143759-14143880 | TRIO |
| 417 | chr22 | 38148620-38148716 | TRIOBP |
| 418 | chr7 | 19156788-19157227 | TWIST1 |
| 419 | chr7 | 19157436-19157533 | TWIST1 |
| 420 | chr4 | 41259387-41259594 | UCHL1 |
| 421 | chr15 | 63795401-63795636 | USP3 |
| 422 | chr17 | 9548120-9548325 | USP43 |
| 423 | chr12 | 95942077-95942558 | USP44 |
| 424 | chr10 | 17271896-17271994 | VIM |
| 425 | chr7 | 49813135-49814168 | VWC2 |
| 426 | chr7 | 151078646-151078674 | WDR86 |
| 427 | chr12 | 49372205-49372274 | WNT1 |
| 428 | chr11 | 32460759-32460800 | WT1 |
| 429 | chr19 | 4061206-4061360 | ZBTB7A |

TABLE 10-continued

| Marker # | Chromosome | Chromosome Coordinates | Annotation |
|---|---|---|---|
| 430 | chr8 | 144623045-144623088 | ZC3H3 |
| 431 | chr2 | 145274698-145274874 | ZEB2 |
| 432 | chr19 | 38146299-38146397 | ZFP30 |
| 433 | chr16 | 88521287-88521377 | ZFPM1 |
| 434 | chr4 | 2298384-2298498 | ZFYVE28 |
| 435 | chr4 | 2415252-2415286 | ZFYVE28 |
| 436 | chr20 | 45986341-45986684 | ZMYND8 |
| 437 | chr22 | 22862957-22862983 | ZNF280B |
| 438 | chr6 | 43336449-43336545 | ZNF318 |
| 439 | chr19 | 53661819-53662279 | ZNF347 |
| 440 | chr16 | 88497041-88497148 | ZNF469 |
| 441 | chr19 | 57019064-57019137 | ZNF471 |
| 442 | chr19 | 2842178-2842235 | ZNF555 |
| 443 | chr19 | 37958078-37958134 | ZNF570 |
| 444 | chr8 | 125985552-125985847 | ZNF572 |
| 445 | chr19 | 53696101-53696195 | ZNF665 |
| 446 | chr19 | 53696497-53696704 | ZNF665 |
| 447 | chr19 | 20149796-20149923 | ZNF682 |
| 448 | chr19 | 57106617-57106967 | ZNF71 |
| 449 | chr7 | 6655380-6655652 | ZNF853 |

In Table 10, bases are numbered according to the February 2009 human genome assembly GRCh37/hg19 (see, e.g., Rosenbloom et al. (2012) "ENCODE whole-genome data in the UCSC Genome Browser: update 2012" *Nucleic Acids Research* 40: D912-D917). The marker names BHLHE23 and LOC63930 refer to the same marker.

TABLE 11

| Chromosome | Chromosome Coordinates | Annotation | Area under the ROC Curve |
|---|---|---|---|
| chr12 | 53298237-53298384 | KRT8 | 1.00 |
| chr7 | 129794337-129794536 | MAX.chr7.129794337-129794536 | 1.00 |
| chr10 | 101282185-101282257 | MAX.chr10.101282185-101282257 | 0.99 |
| chr10 | 126812450-126812653 | CTBP2 | 0.99 |
| chr9 | 116151083-116151315 | ALAD | 0.99 |
| chr8 | 13014567-13014682 | DLC1 | 0.99 |
| chr7 | 139440133-139440341 | HIPK2 | 0.99 |
| chr3 | 39851068-39851989 | MYRIP | 0.99 |
| chr19 | 4061206-4061360 | ZBTB7A | 0.99 |
| chr16 | 84875643-84875772 | CRISPLD2 | 0.99 |
| chr6 | 52268531-52268702 | PAQR8 | 0.99 |
| chr2 | 239194812-239194946 | PER2 | 0.99 |
| chr17 | 1835463-1835690 | MAX.chr17.1835463-1835690 | 0.99 |
| chr5 | 506178-506343 | SLC9A3 | 0.99 |
| chr20 | 31061389-31061649 | C20orf112 | 0.98 |
| chr9 | 139438534-139438629 | NOTCH1 | 0.98 |
| chr15 | 48470606-48470725 | MYEF2 | 0.98 |
| chr12 | 125002129-125002192 | NCOR2 | 0.98 |
| chr4 | 7367687-7367825 | SORCS2 | 0.98 |
| chr19 | 6236947-6237089 | MLLT1 | 0.98 |
| chr7 | 544848-545022 | PDGFA | 0.98 |
| chr7 | 98029116-98029383 | BAIAP2L1 | 0.98 |
| chr4 | 2415252-2415286 | ZFYVE28 | 0.98 |
| chr12 | 6419210-6419489 | PLEKHG6 | 0.98 |
| chr22 | 50825886-50825981 | PPP6R2 | 0.97 |
| chr20 | 45986341-45986684 | ZMYND8 | 0.97 |
| chr5 | 142100518-142100780 | MAX.chr5.142100518-142100780 | 0.97 |
| chr19 | 16473958-16474095 | EPS15L1 | 0.97 |
| chr16 | 29118636-29118891 | RRN3P2 | 0.97 |
| chr6 | 75794978-75795024 | COL12A1 | 0.97 |
| chr9 | 139735581-139735683 | C9orf172 | 0.97 |
| chr17 | 4462834-4463034 | GGT6 | 0.97 |
| chr17 | 4463796-4464037 | GGT6 | 0.96 |
| chr12 | 95942077-95942558 | USP44 | 0.96 |
| chr20 | 42984244-42984427 | HNF4A | 0.96 |
| chr7 | 47650711-47650882 | MAX.chr7.47650711-47650882 | 0.96 |
| chr4 | 942190-942382 | TMEM175 | 0.96 |
| chr7 | 73245708-73245798 | CLDN4 | 0.96 |
| chr22 | 46974925-46975007 | MAX.chr22.46974925-46975007 | 0.96 |
| chr10 | 127033272-127033428 | MAX.chr10.127033272-127033428 | 0.96 |
| chr3 | 132273353-132273532 | MAX.chr3.132273353-132273532 | 0.96 |
| chr4 | 26828422-26828522 | MAX.chr4.26828422-26828522 | 0.96 |
| chr20 | 61284095-61284194 | SLCO4A1 | 0.96 |

TABLE 11-continued

| Chromosome | Chromosome Coordinates | Annotation | Area under the ROC Curve |
|---|---|---|---|
| chr19 | 35540057-35540200 | HPN | 0.96 |
| chr22 | 45099093-45099304 | PRR5 | 0.95 |
| chr17 | 60218266-60218449 | MAX.chr17.60218266-60218449 | 0.95 |
| chr6 | 168333306-168333467 | MLLT4 | 0.95 |
| chr10 | 105338596-105338843 | NEURL | 0.95 |
| chr9 | 120175665-120176057 | ASTN2 | 0.95 |
| chr4 | 183817058-183817157 | DCTD | 0.95 |
| chr6 | 108882636-108882682 | FOXO3 | 0.95 |
| chr7 | 27136030-27136245 | HOXA1 | 0.95 |
| chr19 | 14172823-14172948 | PALM3 | 0.95 |
| chr3 | 75411368-75411473 | MAX.chr3.75411368-75411473 | 0.94 |
| chr6 | 64168133-64168268 | MAX.chr6.64168133-64168268 | 0.94 |
| chr16 | 318717-318893 | RGS11 | 0.94 |
| chr20 | 43040031-43040119 | HNF4A | 0.94 |
| chr7 | 49813135-49814168 | VWC2 | 0.94 |
| chr16 | 85230248-85230405 | MAX.chr16.85230248-85230405 | 0.94 |
| chr22 | 38148620-38148716 | TRIOBP | 0.94 |
| chr5 | 89769002-89769411 | MBLAC2 | 0.94 |
| chr1 | 158150797-158151205 | CD1D | 0.93 |
| chr19 | 1406516-1406625 | DAZAP1 | 0.93 |
| chr12 | 121416542-121416670 | HNF1A | 0.93 |
| chr17 | 76337726-76337824 | MAX.chr17.76337726-76337824 | 0.93 |
| chr13 | 88330094-88330355 | SLITRK5 | 0.93 |
| chr19 | 54974004-54974086 | LENG9 | 0.93 |
| chr22 | 47130339-47130459 | CERK | 0.92 |
| chr7 | 601162-601552 | PRKAR1B | 0.92 |
| chr2 | 70994498-70994755 | ADD2 | 0.92 |
| chr15 | 40361431-40361644 | MAX.chr15.40361431-40361644 | 0.92 |
| chr19 | 15568448-15568639 | RASAL3 | 0.92 |
| chr6 | 24776486-24776667 | GMNN | 0.92 |
| chr18 | 449695-449798 | COLEC12 | 0.92 |
| chr7 | 150760388-150760530 | SLC4A2 | 0.92 |
| chr21 | 38120336-38120558 | SIM2 | 0.91 |
| chr15 | 66999854-67000014 | SMAD6 | 0.91 |
| chr2 | 28844174-28844270 | PLB1 | 0.91 |
| chr11 | 115373179-115373281 | CADM1 | 0.91 |
| chr21 | 47063793-47064177 | PCBP3 | 0.91 |
| chr2 | 1748338-1748444 | PXDN | 0.91 |
| chr21 | 47063798-47063877 | MAX.chr21.47063798-47063877 | 0.91 |
| chr16 | 56715756-56716025 | MT1X | 0.90 |
| chr4 | 87934353-87934488 | AFF1 | 0.90 |
| chr9 | 140091343-140091644 | TPRN | 0.90 |
| chr5 | 15500208-15500399 | FBXL7 | 0.90 |
| chr19 | 48833763-48833967 | EMP3 | 0.90 |
| chr6 | 43141954-43142058 | SRF | 0.90 |
| chr3 | 185215700-185215782 | TMEM41A | 0.90 |
| chr1 | 160983607-160983768 | F11R | 0.90 |
| chr12 | 58259413-58259475 | MAX.chr12.58259413-58259475 | 0.90 |
| chr2 | 47797260-47797371 | KCNK12 | 0.89 |
| chr16 | 4377510-4377615 | GLIS2 | 0.89 |
| chr15 | 63795401-63795636 | USP3 | 0.89 |
| chr13 | 33001061-33001251 | N4BP2L1 | 0.89 |
| chr3 | 120626999-120627116 | STXBP5L | 0.89 |
| chr7 | 19156788-19157227 | TWIST1 | 0.89 |
| chr18 | 46190841-46190970 | KIAA0427 | 0.89 |
| chr7 | 100203461-100203600 | PCOLCE | 0.88 |
| chr19 | 51228217-51228732 | CLEC11A | 0.88 |
| chr19 | 17438929-17438974 | ANO8 | 0.88 |
| chr12 | 2800756-2800899 | CACNA1C | 0.88 |
| chr6 | 34205664-34206018 | HMGA1 | 0.88 |
| chr15 | 76632356-76632462 | ISL2 | 0.88 |
| chr6 | 111873064-111873162 | LOC643749 | 0.88 |
| chr10 | 70359250-70359439 | TET1 | 0.88 |
| chr2 | 39665069-39665282 | MAP4K3 | 0.88 |
| chr2 | 43153331-43153424 | MAX.chr2.43153331-43153424 | 0.87 |
| chr22 | 17849540-17849622 | MAX.chr22.17849540-17849622 | 0.87 |
| chr2 | 233877877-233878027 | NGEF | 0.87 |
| chr8 | 89339567-89339662 | MMP16 | 0.87 |
| chr13 | 46960767-46961669 | C13orf18 | 0.87 |
| chr6 | 170598276-170598782 | DLL1 | 0.87 |
| chr4 | 40516823-40516984 | RBM47 | 0.87 |
| chr3 | 139654045-139654132 | CLSTN2 | 0.87 |
| chr2 | 27486089-27486170 | SLC30A3 | 0.87 |
| chr17 | 74519328-74519457 | PRCD | 0.86 |
| chr2 | 163174366-163174659 | IFIH1 | 0.86 |
| chr4 | 41259387-41259594 | UCHL1 | 0.86 |
| chr7 | 45613877-45614572 | ADCY1 | 0.86 |

TABLE 11-continued

| Chromosome | Chromosome Coordinates | Annotation | Area under the ROC Curve |
|---|---|---|---|
| chr7 | 98990897-98990989 | ARPC1B | 0.86 |
| chr3 | 54156904-54156987 | CACNA2D3 | 0.86 |
| chr16 | 49316205-49316258 | CBLN1 | 0.86 |
| chr3 | 71478053-71478206 | FOXP1 | 0.86 |
| chr5 | 87956937-87956996 | LOC645323 | 0.86 |
| chr21 | 43189031-43189229 | RIPK4 | 0.86 |
| chr12 | 22487528-22487848 | ST8SIA1 | 0.86 |
| chr20 | 42544780-42544835 | TOX2 | 0.86 |
| chr20 | 821836-821871 | FAM110A | 0.86 |
| chr16 | 4310204-4310233 | TFAP4 | 0.86 |
| chr11 | 64110001-64110069 | CCDC88B | 0.85 |
| chr8 | 136469529-136469873 | KHDRBS3 | 0.85 |
| chr10 | 102985059-102985130 | FLJ41350 | 0.85 |
| chr2 | 176971915-176971968 | HOXD11 | 0.85 |
| chr12 | 51319165-51319319 | METTL7A | 0.85 |
| chr22 | 50342922-50343232 | MAX.chr22.50342922-50343232 | 0.85 |
| chr7 | 155597793-155597973 | SHH | 0.85 |
| chr4 | 154712157-154712232 | SFRP2 | 0.84 |
| chr19 | 57019064-57019137 | ZNF471 | 0.84 |
| chr5 | 87970260-87970568 | LOC645323 | 0.84 |
| chr6 | 130686773-130686820 | TMEM200a | 0.84 |
| chr9 | 140201493-140201583 | EXD3 | 0.84 |
| chr12 | 53447992-53448072 | LOC283335 | 0.84 |
| chr22 | 43044555-43044737 | CYB5R3 | 0.84 |
| chr19 | 49256413-49256451 | FGF21 | 0.84 |
| chr17 | 77810085-77810206 | CBX4 | 0.84 |
| chr7 | 156802460-156802490 | MNX1 | 0.84 |
| chr7 | 151127086-151127195 | CRYGN | 0.83 |
| chr6 | 169613138-169613249 | MAX.chr6.169613138-169613249 | 0.83 |
| chr2 | 71503632-71503860 | MAX.chr2.71503632-71503860 | 0.83 |
| chr20 | 21686466-21686563 | PAX1 | 0.83 |
| chr2 | 173293542-173293644 | ITGA6 | 0.83 |
| chr7 | 87229775-87229856 | ABCB1 | 0.83 |
| chr2 | 207307687-207307794 | ADAM23 | 0.83 |
| chr12 | 21680381-21680438 | C12orf39 | 0.83 |
| chr15 | 89942904-89943197 | MAX.chr15.89942904-89943197 | 0.83 |
| chr10 | 43572798-43572896 | RET | 0.83 |
| chr19 | 5805881-5805968 | MAX.chr19.5805881-5805968 | 0.83 |
| chr19 | 53661819-53662279 | ZNF347 | 0.83 |
| chr22 | 38732124-38732211 | MAX.chr22.38732124-38732211 | 0.83 |
| chr11 | 124615979-124616029 | NRGN | 0.83 |
| chr2 | 100720494-100720679 | AFF3 | 0.83 |
| chr19 | 497878-497933 | MADCAM1 | 0.82 |
| chr5 | 14143759-14143880 | TRIO | 0.82 |
| chr18 | 32073971-32074004 | DTNA | 0.82 |
| chr15 | 48470062-48470503 | MYEF2 | 0.82 |
| chr3 | 50243467-50243553 | SLC38A3 | 0.82 |
| chr16 | 70415312-70415673 | ST3GAL2 | 0.82 |
| chr11 | 35441199-35441260 | SLC1A2 | 0.82 |
| chr12 | 51786085-51786218 | GALNT6 | 0.82 |
| chr2 | 232530964-232531124 | MAX.chr2.232530964-232531124 | 0.81 |
| chr22 | 19710910-19710984 | GP1BB | 0.81 |
| chr19 | 2097386-2097437 | IZUMO4 | 0.81 |
| chr11 | 20178177-20178304 | DBX1 | 0.81 |
| chr7 | 37487539-37488596 | ELMO1 | 0.81 |
| chr11 | 128564106-128564209 | FLI1 | 0.81 |
| chr7 | 105029460-105029585 | SRPK2 | 0.81 |
| chr10 | 103538848-103539033 | FGF8 | 0.81 |
| chr11 | 124616860-124617005 | NRGN | 0.81 |
| chr19 | 57106617-57106967 | ZNF71 | 0.81 |
| chr9 | 97401449-97401602 | FBP1 | 0.81 |
| chr5 | 113696971-113697058 | KCNN2 | 0.80 |
| chr19 | 53696497-53696704 | ZNF665 | 0.80 |
| chr1 | 45769962-45770141 | LOC400752 | 0.80 |
| chr14 | 91883473-91883674 | CCDC88C | 0.80 |
| chr17 | 43324999-43325188 | LOC100133991 | 0.80 |
| chr16 | 23846964-23847339 | PRKCB | 0.80 |
| chr19 | 11805543-11805639 | MAX.chr19.11805543-11805639 | 0.80 |
| chr12 | 117174873-117175030 | C12orf49 | 0.80 |
| chr20 | 39995010-39995051 | EMILIN3 | 0.80 |
| chr5 | 87970751-87970850 | LOC645323 | 0.80 |
| chr7 | 4923056-4923107 | RADIL | 0.80 |
| chr19 | 23941063-23941142 | RPSAP58 | 0.80 |
| chr6 | 45387405-45387456 | RUNX2 | 0.80 |
| chr17 | 6949717-6949778 | SLC16A11 | 0.80 |
| chr2 | 165477564-165477609 | GRB14 | 0.80 |
| chr20 | 34189488-34189693 | FER1L4 | 0.80 |

TABLE 11-continued

| Chromosome | Chromosome Coordinates | Annotation | Area under the ROC Curve |
|---|---|---|---|
| chr22 | 50745629-50745727 | PLXNB2 | 0.79 |
| chr7 | 155302557-155302639 | CNPY1 | 0.79 |
| chr7 | 19157436-19157533 | TWIST1 | 0.79 |
| chr1 | 203619509-203619829 | ATP2B4 | 0.79 |
| chr2 | 230578698-230578802 | DNER | 0.79 |
| chr19 | 23941384-23941670 | RPSAP58 | 0.79 |
| chr17 | 73390467-73390597 | GRB2 | 0.79 |
| chr15 | 68115602-68115675 | SKOR1 | 0.79 |
| chr17 | 2300399-2300476 | MNT | 0.79 |
| chr13 | 79177868-79177951 | POU4F1 | 0.79 |
| chr19 | 59025337-59025385 | SLC27A5 | 0.79 |
| chr9 | 135462730-135462765 | BARHL1 | 0.78 |
| chr8 | 125985552-125985847 | ZNF572 | 0.78 |
| chr5 | 175665232-175665311 | C5orf25 | 0.78 |
| chr6 | 42858890-42859092 | C6orf226 | 0.78 |
| chr12 | 21680681-21680817 | C12orf39 | 0.78 |
| chr14 | 50099743-50099930 | C14orf104 | 0.78 |
| chr5 | 175969660-175969699 | CDHR2 | 0.78 |
| chr16 | 80837397-80837505 | CDYL2 | 0.78 |
| chr19 | 12996198-12996321 | DNASE2 | 0.78 |
| chr13 | 28674451-28674629 | FLT3 | 0.78 |
| chr1 | 154733071-154733232 | KCNN3 | 0.78 |
| chr1 | 35395179-35395201 | MAX.chr1.35395179-35395201 | 0.78 |
| chr19 | 5340273-5340743 | PTPRS | 0.78 |
| chr3 | 33260338-33260423 | SUSD5 | 0.78 |
| chr2 | 145274698-145274874 | ZEB2 | 0.78 |
| chr13 | 25322044-25322165 | MAX.chr13.25322044-25322165 | 0.78 |
| chr2 | 80530326-80530374 | CTNNA2 | 0.78 |
| chr12 | 56881329-56881414 | GLS2 | 0.78 |
| chr3 | 24563009-24563117 | MAX.chr3.24563009-24563117 | 0.78 |
| chr7 | 6655380-6655652 | ZNF853 | 0.78 |
| chr4 | 2298384-2298498 | ZFYVE28 | 0.77 |
| chr5 | 177632203-177632260 | HNRNPAB | 0.77 |
| chr22 | 19711364-19711385 | GP1BB | 0.77 |
| chr2 | 165477839-165477886 | GRB14 | 0.77 |
| chr13 | 29394692-29394771 | MAX.chr13.29394692-29394771 | 0.77 |
| chr14 | 103396870-103396920 | AMN | 0.77 |
| chr12 | 132435207-132435428 | EP400 | 0.77 |
| chr8 | 99439457-99439482 | KCNS2 | 0.77 |
| chr7 | 5821188-5821283 | RNF216 | 0.77 |
| chr17 | 9548120-9548325 | USP43 | 0.77 |
| chr3 | 185825887-185826002 | ETV5 | 0.77 |
| chr12 | 121905558-121905792 | KDM2B | 0.77 |
| chr3 | 193858771-193858843 | MAX.chr3.193858771-193858843 | 0.77 |
| chr19 | 53696101-53696195 | ZNF665 | 0.77 |
| chr7 | 69062853-69062972 | AUTS2 | 0.77 |
| chr1 | 242687719-242687746 | PLD5 | 0.76 |
| chr20 | 43948422-43948484 | MAX.chr20.43948422-43948484 | 0.76 |
| chr6 | 84419007-84419072 | SNAP91 | 0.76 |
| chr17 | 43325784-43325960 | LOC100133991 | 0.76 |
| chr19 | 41224781-41225006 | ADCK4 | 0.76 |
| chr5 | 15500663-15500852 | FBXL7 | 0.76 |
| chr20 | 20350520-20350532 | INSM1 | 0.76 |
| chr1 | 23894874-23894919 | MAX.chr1.23894874-23894919 | 0.76 |
| chr1 | 11538685-11538738 | PTCHD2 | 0.76 |
| chr14 | 105190863-105191031 | ADSSL1 | 0.76 |
| chr22 | 22862957-22862983 | ZNF280B | 0.76 |
| chr17 | 72350351-72350403 | KIF19 | 0.76 |
| chr7 | 50343838-50344029 | IKZF1 | 0.76 |
| chr2 | 191272534-191272765 | MFSD6 | 0.76 |
| chr17 | 47073421-47073440 | IGF2BP1 | 0.76 |
| chr10 | 133795124-133795423 | BNIP3 | 0.75 |
| chr5 | 101631546-101631731 | SLCO4C1 | 0.75 |
| chr12 | 133485702-133485739 | MAX.chr12.133485702-133485739 | 0.75 |
| chr22 | 18923785-18923823 | PRODH | 0.75 |
| chr20 | 56089440-56089547 | CTCFL | 0.75 |
| chr6 | 43336449-43336545 | ZNF318 | 0.75 |
| chr14 | 61123624-61123707 | MAX.chr14.61123624-61123707 | 0.75 |
| chr7 | 30721980-30722020 | CRHR2 | 0.75 |
| chr17 | 7339280-7339492 | FGF11 | 0.75 |
| chr11 | 84432067-84432186 | DLG2 | 0.75 |
| chr2 | 233352345-233352605 | ECEL1 | 0.75 |
| chr3 | 27763358-27763617 | EOMES | 0.75 |
| chr5 | 160975098-160975142 | GABRB2 | 0.75 |
| chr1 | 244012804-244012986 | MAX.chr1.244012804-244012986 | 0.75 |
| chr16 | 25042924-25043187 | MAX.chr16.25042924-25043187 | 0.75 |
| chr4 | 57775698-57775771 | REST | 0.75 |

TABLE 11-continued

| Chromosome | Chromosome Coordinates | Annotation | Area under the ROC Curve |
|---|---|---|---|
| chr6 | 127440492-127441039 | RSPO3 | 0.75 |
| chr8 | 145561664-145561696 | SCRT1 | 0.75 |
| chr8 | 144623045-144623088 | ZC3H3 | 0.75 |
| chr12 | 48398051-48398093 | COL2A1 | 0.75 |
| chr2 | 182321880-182322022 | ITGA4 | 0.75 |
| chr9 | 120507310-120507354 | MAX.chr9.120507310-120507354 | 0.74 |
| chr6 | 133562127-133562229 | EYA4 | 0.74 |
| chr2 | 127783183-127783233 | MAX.chr2.127783183-127783233 | 0.74 |
| chr11 | 47421719-47421776 | MAX.chr11.47421719-47421776 | 0.74 |
| chr19 | 10206736-10206757 | ANGPTL6 | 0.74 |
| chr2 | 225907414-225907537 | DOCK10 | 0.74 |
| chr1 | 35394690-35394876 | MAX.chr1.35394690-35394876 | 0.74 |
| chr4 | 2060477-2060624 | NAT8L | 0.74 |
| chr2 | 1747034-1747126 | PXDN | 0.74 |
| chr6 | 45345446-45345595 | RUNX2 | 0.74 |
| chr7 | 50344414-50344453 | IKZF1 | 0.74 |
| chr1 | 180198528-180198542 | LHX4 | 0.74 |
| chr14 | 53417493-53417618 | FERMT2 | 0.74 |
| chr17 | 77179784-77179887 | RBFOX3 | 0.74 |
| chr10 | 98945242-98945493 | SLIT1 | 0.74 |
| chr2 | 40679298-40679326 | SLC8A1 | 0.74 |
| chr12 | 48398306-48398375 | COL2A1 | 0.74 |
| chr22 | 50987245-50987312 | KLHDC7B | 0.73 |
| chr12 | 54151078-54151153 | MAX.chr12.54151078-54151153 | 0.73 |
| chr7 | 28893550-28893569 | MAX.chr7.28893550-28893569 | 0.73 |
| chr10 | 38691448-38691521 | SEPT7L | 0.73 |
| chr1 | 203044913-203044929 | PPFIA4 | 0.73 |
| chr22 | 51066374-51066431 | ARSA | 0.73 |
| chr7 | 113724864-113725006 | FOXP2 | 0.73 |
| chr12 | 13254503-13254606 | GSG1 | 0.73 |
| chr11 | 19733958-19734013 | LOC100126784 | 0.73 |
| chr1 | 39044345-39044354 | MAX.chr1.39044345-39044354 | 0.73 |
| chr3 | 9988302-9988499 | PRRT3 | 0.73 |
| chr22 | 20785373-20785464 | SCARF2 | 0.73 |
| chr6 | 130687200-130687735 | TMEM200a | 0.73 |
| chr12 | 46661132-46661306 | SLC38A1 | 0.73 |
| chr19 | 20149796-20149923 | ZNF682 | 0.73 |
| chr11 | 133797643-133797789 | IGSF9B | 0.73 |
| chr2 | 105471752-105471787 | POU3F3 | 0.72 |
| chr5 | 179780839-179780955 | GFPT2 | 0.72 |
| chr8 | 99952501-99952533 | OSR2 | 0.72 |
| chr19 | 16772631-16772712 | C19orf42 | 0.72 |
| chr2 | 119607676-119607765 | EN1 | 0.72 |
| chr12 | 49372205-49372274 | WNT1 | 0.72 |
| chr5 | 113696524-113696682 | KCNN2 | 0.72 |
| chr17 | 8649567-8649665 | CCDC42 | 0.72 |
| chr7 | 1705957-1706065 | MAX.chr7.1705957-1706065 | 0.71 |
| chr2 | 149633039-149633137 | KIF5C | 0.71 |
| chr19 | 2842178-2842235 | ZNF555 | 0.71 |
| chr10 | 121302439-121302501 | RGS10 | 0.71 |
| chr21 | 44495919-44495933 | CBS | 0.71 |
| chr10 | 11059508-11060151 | CELF2 | 0.71 |
| chr19 | 48946755-48946912 | GRIN2D | 0.71 |
| chr12 | 133484978-133485066 | MAX.chr12.133484978-133485066 | 0.71 |
| chr5 | 16936010-16936058 | MYO10 | 0.71 |
| chr17 | 42392669-42392701 | RUNDC3A | 0.71 |
| chr16 | 88521287-88521377 | ZFPM1 | 0.71 |
| chr4 | 37245694-37245718 | KIAA1239 | 0.71 |
| chr16 | 23847507-23847617 | PRKCB | 0.71 |
| chr5 | 76926598-76926703 | OTP | 0.71 |
| chr18 | 31803017-31803114 | NOL4 | 0.71 |
| chr2 | 182322168-182322198 | ITGA4 | 0.70 |
| chr15 | 90358267-90358400 | ANPEP | 0.70 |
| chr12 | 107715014-107715095 | BTBD11 | 0.70 |
| chr16 | 89007413-89007432 | CBFA2T3 | 0.70 |
| chr4 | 151000325-151000356 | DCLK2 | 0.70 |
| chr6 | 152129293-152129450 | ESR1 | 0.70 |
| chr19 | 38146299-38146397 | ZFP30 | 0.70 |
| chr1 | 204797773-204797785 | NFASC | 0.70 |
| chr22 | 42764974-42765049 | MAX.chr22.42764974-42765049 | 0.70 |
| chr2 | 165698520-165698578 | COBLL1 | 0.70 |
| chr8 | 144358251-144358266 | GLI4 | 0.70 |
| chr2 | 219261190-219261327 | CTDSP1 | 0.70 |
| chr2 | 239957125-239957163 | MAX.chr2.239957125-239957163 | 0.70 |
| chr10 | 121411207-121411375 | BAG3 | 0.69 |
| chr2 | 233389020-233389049 | CHRND | 0.69 |
| chr14 | 99946756-99946806 | CCNK | 0.69 |

TABLE 11-continued

| Chromosome | Chromosome Coordinates | Annotation | Area under the ROC Curve |
|---|---|---|---|
| chr11 | 120382450-120382498 | MAX.chr11.120382450-120382498 | 0.69 |
| chr16 | 750679-750715 | FBXL16 | 0.69 |
| chr15 | 100881373-100881437 | ADAMTS17 | 0.69 |
| chr1 | 11539396-11539540 | PTCHD2 | 0.69 |
| chr2 | 242447608-242447724 | STK25 | 0.69 |
| chr16 | 23847825-23848168 | PRKCB | 0.69 |
| chr17 | 42907549-42907807 | GJC1 | 0.69 |
| chr19 | 48918266-48918311 | GRIN2D | 0.69 |
| chr10 | 79397895-79397945 | KCNMA1 | 0.69 |
| chr5 | 71404528-71404563 | MAP1B | 0.69 |
| chr19 | 43979400-43979435 | PHLDB3 | 0.69 |
| chr17 | 70116754-70116823 | SOX9 | 0.69 |
| chr16 | 88497041-88497148 | ZNF469 | 0.69 |
| chr2 | 131485151-131485219 | GPR148 | 0.69 |
| chr8 | 126441476-126441519 | TRIB1 | 0.68 |
| chr4 | 151000358-151000403 | DCLK2 | 0.68 |
| chr19 | 39989824-39989852 | DLL3 | 0.68 |
| chr14 | 89507100-89507162 | MAX.chr14.89507100-89507162 | 0.68 |
| chr12 | 115122614-115122632 | TBX3 | 0.68 |
| chr19 | 58513829-58513851 | LOC100128398 | 0.68 |
| chr5 | 32714270-32714325 | NPR3 | 0.68 |
| chr3 | 140770014-140770193 | SPSB4 | 0.68 |
| chr6 | 88875699-88875763 | CNR1 | 0.68 |
| chr4 | 657555-657666 | PDE6B | 0.68 |
| chr16 | 19179713-19179744 | SYT17 | 0.67 |
| chr3 | 8809858-8809865 | OXTR | 0.67 |
| chr10 | 116064516-116064600 | AFAP1L2 | 0.67 |
| chr4 | 77610781-77610824 | SHROOM3 | 0.67 |
| chr6 | 88876367-88876445 | CNR1 | 0.67 |
| chr7 | 151078646-151078674 | WDR86 | 0.67 |
| chr2 | 109745715-109745742 | LOC100287216 | 0.67 |
| chr14 | 100751586-100751695 | MAX.chr14.100751586-100751695 | 0.67 |
| chr21 | 32930371-32930409 | TIAM1 | 0.67 |
| chr4 | 57687746-57687764 | SPINK2 | 0.67 |
| chr2 | 219849962-219850042 | FEV | 0.66 |
| chr20 | 327754-327871 | NRSN2 | 0.66 |
| chr1 | 178063099-178063167 | LOC100302401 | 0.66 |
| chr19 | 45430362-45430458 | APOC1P1 | 0.66 |
| chr13 | 111767862-111768355 | ARHGEF7 | 0.66 |
| chr19 | 37958078-37958134 | ZNF570 | 0.66 |
| chr19 | 32715650-32715707 | MAX.chr19.32715650-32715707 | 0.66 |
| chr8 | 104152963-104152974 | BAALC | 0.66 |
| chr19 | 3095019-3095055 | GNA11 | 0.66 |
| chr19 | 3606372-3606418 | TBXA2R | 0.66 |
| chr12 | 69140018-69140206 | SLC35E3 | 0.66 |
| chr4 | 8965831-8965868 | MAX.chr4.8965831-8965868 | 0.66 |
| chr17 | 36508733-36508891 | SOCS7 | 0.66 |
| chr16 | 85646495-85646594 | KIAA0182 | 0.65 |
| chr7 | 54826636-54826706 | SEC61G | 0.65 |
| chr9 | 108418404-108418453 | MAX.chr9.108418404-108418453 | 0.65 |
| chr7 | 64408106-64408135 | MAX.chr7.64408106-64408135 | 0.65 |
| chr10 | 21816267-21816490 | C10orf140 | 0.65 |
| chr7 | 39989959-39990020 | CDK13 | 0.65 |
| chr1 | 240255240-240255264 | FMN2 | 0.65 |
| chr13 | 114018369-114018421 | GRTP1 | 0.65 |
| chr13 | 88323571-88323647 | LOC642345 | 0.65 |
| chr5 | 80256215-80256313 | RASGRF2 | 0.65 |
| chr10 | 112064230-112064280 | SMNDC1 | 0.65 |
| chr12 | 85430135-85430175 | LRRIQ1 | 0.65 |
| chr1 | 241520322-241520334 | RGS7 | 0.65 |
| chr19 | 22034747-22034887 | MAX.chr19.22034747-22034887 | 0.65 |
| chr21 | 27011846-27011964 | JAM2 | 0.65 |
| chr11 | 64052053-64052132 | BAD | 0.65 |
| chr1 | 42846119-42846174 | RIMKLA | 0.64 |
| chr10 | 17271896-17271994 | VIM | 0.64 |
| chr13 | 52378159-52378202 | DHRS12 | 0.63 |
| chr3 | 27763909-27763981 | EOMES | 0.63 |
| chr7 | 100136884-100137350 | AGFG2 | 0.62 |
| chr6 | 88876701-88876726 | CNR1 | 0.62 |
| chr19 | 2290471-2290541 | LINGO3 | 0.62 |
| chr6 | 105584524-105584800 | BVES | 0.61 |
| chr16 | 23607524-23607650 | NDUFAB1 | 0.61 |
| chr11 | 64008415-64008495 | FKBP2 | 0.60 |
| chr20 | 3641457-3641537 | GFRA4 | 0.59 |
| chr19 | 4343896-4242968 | MPND | 0.59 |
| chr2 | 107503155-107503391 | ST6GAL2 | 0.59 |
| chr1 | 240161479-240161546 | MAX.chr1.240161479-240161546 | 0.57 |

TABLE 11-continued

| Chromosome | Chromosome Coordinates | Annotation | Area under the ROC Curve |
|---|---|---|---|
| chr6 | 144384503-144385539 | PLAGL1 | 0.57 |
| chr3 | 72496092-72496361 | RYBP | 0.57 |
| chr5 | 131132146-131132232 | FNIP1 | 0.55 |
| chr17 | 36762706-36762763 | SRCIN1 | 0.55 |
| chr11 | 32460759-32460800 | WT1 | 0.55 |
| chr9 | 127266951-127267032 | NR5A1 | 0.53 |
| chr7 | 44084171-44084235 | DBNL | 0.46 |
| chr15 | 29131299-29131369 | APBA2 | 0.44 |
| chr5 | 114880375-114880442 | FEM1C | 0.44 |
| chr19 | 34287890-34287972 | KCTD15 | 0.44 |
| chr16 | 77468655-77468742 | ADAMTS18 | |
| chr22 | 45898798-45898888 | FBLN1 | |
| chr7 | 113727624-113727693 | FOXP2 | |
| chr7 | 43152309-43152375 | HECW1 | |
| chr20 | 20345123-20345150 | INSM1 | |
| chr20 | 61637950-61638000 | LOC63930 | |
| chr1 | 156406057-156406118 | MAX.chr1.156406057-156406118 | |
| chr10 | 23480864-23480913 | PTF1A | |
| chr5 | 1445384-1445473 | SLC6A3 | |
| chr2 | 107502978-107503055 | ST6GAL2 | |
| chr10 | 17496177-17496310 | ST8SIA6 | |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method for measuring the methylation level of one or more CpG sites in CLEC11A comprising:
   a) extracting genomic DNA from a biological sample of a human individual suspected of having or having a gastrointestinal neoplasm, a pancreas neoplasm, a stomach neoplasm and/or an esophagus neoplasm,
   b) treating the extracted genomic DNA with bisulfite,
   c) amplifying the bisulfite-treated genomic DNA with primers consisting of a pair of primers specific for CLEC11A, and
   d) measuring the methylation level of one or more CpG sites in CLEC11A by methylation-specific PCR, quantitative methylation-specific PCR, methylation sensitive DNA restriction enzyme analysis or bisulfite genomic sequencing PCR.

2. The method of claim 1 wherein the sample is a stool sample, an esophageal tissue sample, a tissue sample, a pancreatic juice sample, a pancreatic cyst fluid sample, a blood sample, or a urine sample.

3. The method of claim 1 wherein the pair of primers specific for CLEC11A consists of SEQ ID Nos: 47 and 48.

* * * * *

```
                     SEQUENCE LISTING

<160> NUMBER OF SEQ ID NOS: 202

<210> SEQ ID NO 1
<211> LENGTH: 21
<212> TYPE: DNA
<213> ORGANISM: Artificial sequence
<220> FEATURE:
<223> OTHER INFORMATION: Synthetic

<400> SEQUENCE: 1
gattttgttc gtcgttagtg c                                           21

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
tctctaaacc cgcgaacga                                              19

<210> SEQ ID NO 3
<211> LENGTH: 25
<212> TYPE: DNA
<213> ORGANISM: Artificial sequence
<220> FEATURE:
<223> OTHER INFORMATION: Synthetic

<400> SEQUENCE: 3
ttcgaagttt cgggatagga agcgt                                       25
```

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
cctaccgacc ttcgaacgcg					20

<210> SEQ ID NO 5
<211> LENGTH: 21
<212> TYPE: DNA
<213> ORGANISM: Artificial sequence
<220> FEATURE:
<223> OTHER INFORMATION: Synthetic

<400> SEQUENCE: 5
ggcggcgcgt atttttttcg c					21

<210> SEQ ID NO 6
<211> LENGTH: 23
<212> TYPE: DNA
<213> ORGANISM: Artificial sequence
<220> FEATURE:
<223> OTHER INFORMATION: Synthetic

<400> SEQUENCE: 6
cgctacgata taaacgacga cga				23

<210> SEQ ID NO 7
<211> LENGTH: 19
<212> TYPE: DNA
<213> ORGANISM: Artificial sequence
<220> FEATURE:
<223> OTHER INFORMATION: Synthetic

<400> SEQUENCE: 7
ggttcggttg tcgtagcgc					19

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
ccgaccgtaa tcctcgacga					20

<210> SEQ ID NO 9
<211> LENGTH: 25
<212> TYPE: DNA
<213> ORGANISM: Artificial sequence
<220> FEATURE:
<223> OTHER INFORMATION: Synthetic

<400> SEQUENCE: 9
ttaggtcggg aatcgttatt gtttc				25

<210> SEQ ID NO 10
<211> LENGTH: 22
<212> TYPE: DNA
<213> ORGANISM: Artificial sequence
<220> FEATURE:
<223> OTHER INFORMATION: Synthetic

<400> SEQUENCE: 10
gtaaataacc ccgcgctaaa cg							22

<210> SEQ ID NO 11
<211> LENGTH: 24
<212> TYPE: DNA
<213> ORGANISM: Artificial sequence
<220> FEATURE:
<223> OTHER INFORMATION: Synthetic

<400> SEQUENCE: 11
ttcgtttgtt tttcgggtcg tagc							24

<210> SEQ ID NO 12
<211> LENGTH: 24
<212> TYPE: DNA
<213> ORGANISM: Artificial sequence
<220> FEATURE:
<223> OTHER INFORMATION: Synthetic

<400> SEQUENCE: 12
accacgtaac gatttactcg acga							24

<210> SEQ ID NO 13
<211> LENGTH: 23
<212> TYPE: DNA
<213> ORGANISM: Artificial sequence
<220> FEATURE:
<223> OTHER INFORMATION: Synthetic

<400> SEQUENCE: 13
cgttttcgga tttgaagtcg ttc							23

<210> SEQ ID NO 14
<211> LENGTH: 19
<212> TYPE: DNA
<213> ORGANISM: Artificial sequence
<220> FEATURE:
<223> OTHER INFORMATION: Synthetic

<400> SEQUENCE: 14
cgcctcgtct tccaacgaa							19

<210> SEQ ID NO 15
<211> LENGTH: 19
<212> TYPE: DNA
<213> ORGANISM: Artificial sequence
<220> FEATURE:
<223> OTHER INFORMATION: Synthetic

<400> SEQUENCE: 15
agggcgttcg gttttagtc							19

<210> SEQ ID NO 16
<211> LENGTH: 22
<212> TYPE: DNA
<213> ORGANISM: Artificial sequence
<220> FEATURE:
<223> OTHER INFORMATION: Synthetic

<400> SEQUENCE: 16
aaccgaaaac gacaaaatcg at							22

<210> SEQ ID NO 17
<211> LENGTH: 21

```
<212> TYPE: DNA
<213> ORGANISM: Artificial sequence
<220> FEATURE:
<223> OTHER INFORMATION: Synthetic

<400> SEQUENCE: 17
tttgagcggc ggtcgttgat c                                              21

<210> SEQ ID NO 18
<211> LENGTH: 22
<212> TYPE: DNA
<213> ORGANISM: Artificial sequence
<220> FEATURE:
<223> OTHER INFORMATION: Synthetic

<400> SEQUENCE: 18
tccccgaatc taaacgctac ga                                             22

<210> SEQ ID NO 19
<211> LENGTH: 25
<212> TYPE: DNA
<213> ORGANISM: Artificial sequence
<220> FEATURE:
<223> OTHER INFORMATION: Synthetic

<400> SEQUENCE: 19
tttagggaag taaagcgtcg ttttc                                          25

<210> SEQ ID NO 20
<211> LENGTH: 22
<212> TYPE: DNA
<213> ORGANISM: Artificial sequence
<220> FEATURE:
<223> OTHER INFORMATION: Synthetic

<400> SEQUENCE: 20
aacgacgtct cgatacctac ga                                             22

<210> SEQ ID NO 21
<211> LENGTH: 22
<212> TYPE: DNA
<213> ORGANISM: Artificial sequence
<220> FEATURE:
<223> OTHER INFORMATION: Synthetic

<400> SEQUENCE: 21
ggagagtatt tcggtttttc gc                                             22

<210> SEQ ID NO 22
<211> LENGTH: 24
<212> TYPE: DNA
<213> ORGANISM: Artificial sequence
<220> FEATURE:
<223> OTHER INFORMATION: Synthetic

<400> SEQUENCE: 22
acaaacaaaa tcgaaaaaca cccg                                           24

<210> SEQ ID NO 23
<211> LENGTH: 23
<212> TYPE: DNA
<213> ORGANISM: Artificial sequence
<220> FEATURE:
<223> OTHER INFORMATION: Synthetic

<400> SEQUENCE: 23
```
gttttcgttt cggtcgaggt tac                                    23

<210> SEQ ID NO 24
<211> LENGTH: 25
<212> TYPE: DNA
<213> ORGANISM: Artificial sequence
<220> FEATURE:
<223> OTHER INFORMATION: Synthetic

<400> SEQUENCE: 24
gccattaact cgataaaaaa cgcga                                  25

<210> SEQ ID NO 25
<211> LENGTH: 25
<212> TYPE: DNA
<213> ORGANISM: Artificial sequence
<220> FEATURE:
<223> OTHER INFORMATION: Synthetic

<400> SEQUENCE: 25
gatttaatcg tagattcggg tcgtc                                  25

<210> SEQ ID NO 26
<211> LENGTH: 22
<212> TYPE: DNA
<213> ORGANISM: Artificial sequence
<220> FEATURE:
<223> OTHER INFORMATION: Synthetic

<400> SEQUENCE: 26
ccgaaacgaa cgaactcaaa cg                                     22

<210> SEQ ID NO 27
<211> LENGTH: 17
<212> TYPE: DNA
<213> ORGANISM: Artificial sequence
<220> FEATURE:
<223> OTHER INFORMATION: Synthetic

<400> SEQUENCE: 27
gcgcgtagcg gcgtttc                                           17

<210> SEQ ID NO 28
<211> LENGTH: 19
<212> TYPE: DNA
<213> ORGANISM: Artificial sequence
<220> FEATURE:
<223> OTHER INFORMATION: Synthetic

<400> SEQUENCE: 28
cccatatcgc ccgacgtaa                                         19

<210> SEQ ID NO 29
<211> LENGTH: 22
<212> TYPE: DNA
<213> ORGANISM: Artificial sequence
<220> FEATURE:
<223> OTHER INFORMATION: Synthetic

<400> SEQUENCE: 29
tcgtatttgg cgttcggtag tc                                     22

<210> SEQ ID NO 30
<211> LENGTH: 21
<212> TYPE: DNA
<213> ORGANISM: Artificial sequence

```
<220> FEATURE:
<223> OTHER INFORMATION: Synthetic

<400> SEQUENCE: 30
cgaaatccaa cgccgaaacg a                                          21

<210> SEQ ID NO 31
<211> LENGTH: 24
<212> TYPE: DNA
<213> ORGANISM: Artificial sequence
<220> FEATURE:
<223> OTHER INFORMATION: Synthetic

<400> SEQUENCE: 31
ttgtcgttcg tcgaattcga tttc                                       24

<210> SEQ ID NO 32
<211> LENGTH: 23
<212> TYPE: DNA
<213> ORGANISM: Artificial sequence
<220> FEATURE:
<223> OTHER INFORMATION: Synthetic

<400> SEQUENCE: 32
aacccgacgc taaaaaacga cga                                        23

<210> SEQ ID NO 33
<211> LENGTH: 25
<212> TYPE: DNA
<213> ORGANISM: Artificial sequence
<220> FEATURE:
<223> OTHER INFORMATION: Synthetic

<400> SEQUENCE: 33
ttgcgttggt tacgttttt tacgc                                       25

<210> SEQ ID NO 34
<211> LENGTH: 23
<212> TYPE: DNA
<213> ORGANISM: Artificial sequence
<220> FEATURE:
<223> OTHER INFORMATION: Synthetic

<400> SEQUENCE: 34
acgccgtacg aataacgaaa cga                                        23

<210> SEQ ID NO 35
<211> LENGTH: 21
<212> TYPE: DNA
<213> ORGANISM: Artificial sequence
<220> FEATURE:
<223> OTHER INFORMATION: Synthetic

<400> SEQUENCE: 35 cgttttcgg gtcgggttcg c                                           21

<210> SEQ ID NO 36
<211> LENGTH: 19
<212> TYPE: DNA
<213> ORGANISM: Artificial sequence
<220> FEATURE:
<223> OTHER INFORMATION: Synthetic

<400> SEQUENCE: 36
tccgacgctc gactcccga                                             19
```

```
<210> SEQ ID NO 37
<211> LENGTH: 22
<212> TYPE: DNA
<213> ORGANISM: Artificial sequence
<220> FEATURE:
<223> OTHER INFORMATION: Synthetic

<400> SEQUENCE: 37
tcggcgtatt tttcgtagac gc                                               22

<210> SEQ ID NO 38
<211> LENGTH: 24
<212> TYPE: DNA
<213> ORGANISM: Artificial sequence
<220> FEATURE:
<223> OTHER INFORMATION: Synthetic

<400> SEQUENCE: 38
cgcaatctta aacgtacgct tcga                                             24

<210> SEQ ID NO 39
<211> LENGTH: 24
<212> TYPE: DNA
<213> ORGANISM: Artificial sequence
<220> FEATURE:
<223> OTHER INFORMATION: Synthetic

<400> SEQUENCE: 39
ggtttataaa gagttcggtt tcgc                                             24

<210> SEQ ID NO 40
<211> LENGTH: 24
<212> TYPE: DNA
<213> ORGANISM: Artificial sequence
<220> FEATURE:
<223> OTHER INFORMATION: Synthetic

<400> SEQUENCE: 40
aaaacgctaa actacccgaa tacg                                             24

<210> SEQ ID NO 41
<211> LENGTH: 19
<212> TYPE: DNA
<213> ORGANISM: Artificial sequence
<220> FEATURE:
<223> OTHER INFORMATION: Synthetic

<400> SEQUENCE: 41
tgggcgggtt tcgtcgtac                                                   19

<210> SEQ ID NO 42
<211> LENGTH: 21
<212> TYPE: DNA
<213> ORGANISM: Artificial sequence
<220> FEATURE:
<223> OTHER INFORMATION: Synthetic

<400> SEQUENCE: 42
gtcccgaaac atcgcaaacg a                                                21

<210> SEQ ID NO 43
<211> LENGTH: 19
<212> TYPE: DNA
<213> ORGANISM: Artificial sequence
<220> FEATURE:
<223> OTHER INFORMATION: Synthetic
```

<400> SEQUENCE: 43
gcgtttggat tttgcgttc                                           19

<210> SEQ ID NO 44
<211> LENGTH: 20
<212> TYPE: DNA
<213> ORGANISM: Artificial sequence
<220> FEATURE:
<223> OTHER INFORMATION: Synthetic

<400> SEQUENCE: 44
aaaatacgcc gctaccgata                                          20

<210> SEQ ID NO 45
<211> LENGTH: 20
<212> TYPE: DNA
<213> ORGANISM: Artificial sequence
<220> FEATURE:
<223> OTHER INFORMATION: Synthetic

<400> SEQUENCE: 45
gtttagggag tcgcggttac                                          20

<210> SEQ ID NO 46
<211> LENGTH: 23
<212> TYPE: DNA
<213> ORGANISM: Artificial sequence
<220> FEATURE:
<223> OTHER INFORMATION: Synthetic

<400> SEQUENCE: 46
caaatcctac gaacgaacga acg                                      23

<210> SEQ ID NO 47
<211> LENGTH: 22
<212> TYPE: DNA
<213> ORGANISM: Artificial sequence
<220> FEATURE:
<223> OTHER INFORMATION: Synthetic

<400> SEQUENCE: 47
agtttggcgt agtcggtaga tc                                       22

<210> SEQ ID NO 48
<211> LENGTH: 22
<212> TYPE: DNA
<213> ORGANISM: Artificial sequence
<220> FEATURE:
<223> OTHER INFORMATION: Synthetic

<400> SEQUENCE: 48
gcgcgcaaat accgaataaa cg                                       22

<210> SEQ ID NO 49
<211> LENGTH: 22
<212> TYPE: DNA
<213> ORGANISM: Artificial sequence
<220> FEATURE:
<223> OTHER INFORMATION: Synthetic

<400> SEQUENCE: 49
tcggttttta gcgttcgttc gc                                       22

<210> SEQ ID NO 50

```
<211> LENGTH: 23
<212> TYPE: DNA
<213> ORGANISM: Artificial sequence
<220> FEATURE:
<223> OTHER INFORMATION: Synthetic

<400> SEQUENCE: 50
aaacaacgaa acgccaatcc cga                                              23

<210> SEQ ID NO 51
<211> LENGTH: 25
<212> TYPE: DNA
<213> ORGANISM: Artificial sequence
<220> FEATURE:
<223> OTHER INFORMATION: Synthetic

<400> SEQUENCE: 51
tagtttttgg gcgttatttt cggtc                                            25

<210> SEQ ID NO 52
<211> LENGTH: 21
<212> TYPE: DNA
<213> ORGANISM: Artificial sequence
<220> FEATURE:
<223> OTHER INFORMATION: Synthetic

<400> SEQUENCE: 52
gcaactccgt acactcgacg a                                                21

<210> SEQ ID NO 53
<211> LENGTH: 26
<212> TYPE: DNA
<213> ORGANISM: Artificial sequence
<220> FEATURE:
<223> OTHER INFORMATION: Synthetic

<400> SEQUENCE: 53
tttttcgttt gttttcggt attcgc                                            26

<210> SEQ ID NO 54
<211> LENGTH: 22
<212> TYPE: DNA
<213> ORGANISM: Artificial sequence
<220> FEATURE:
<223> OTHER INFORMATION: Synthetic

<400> SEQUENCE: 54
cgaatcctaa cgaactatcc ga                                               22

<210> SEQ ID NO 55
<211> LENGTH: 25
<212> TYPE: DNA
<213> ORGANISM: Artificial sequence
<220> FEATURE:
<223> OTHER INFORMATION: Synthetic

<400> SEQUENCE: 55
ttcggtggat tttcgtattg atttc                                            25

<210> SEQ ID NO 56
<211> LENGTH: 24
<212> TYPE: DNA
<213> ORGANISM: Artificial sequence
<220> FEATURE:
<223> OTHER INFORMATION: Synthetic

<400> SEQUENCE: 56
```

-continued

```
aaacgaaacc gcgaactaaa acga                                    24

<210> SEQ ID NO 57
<211> LENGTH: 22
<212> TYPE: DNA
<213> ORGANISM: Artificial sequence
<220> FEATURE:
<223> OTHER INFORMATION: Synthetic

<400> SEQUENCE: 57
ttacgtgata gttcggggtt tc                                      22

<210> SEQ ID NO 58
<211> LENGTH: 21
<212> TYPE: DNA
<213> ORGANISM: Artificial sequence
<220> FEATURE:
<223> OTHER INFORMATION: Synthetic

<400> SEQUENCE: 58
ataaaacgac gcgacgaaac g                                       21

<210> SEQ ID NO 59
<211> LENGTH: 24
<212> TYPE: DNA
<213> ORGANISM: Artificial sequence
<220> FEATURE:
<223> OTHER INFORMATION: Synthetic

<400> SEQUENCE: 59
tttcgggttt tgcgttttat tcgc                                    24

<210> SEQ ID NO 60
<211> LENGTH: 28
<212> TYPE: DNA
<213> ORGANISM: Artificial sequence
<220> FEATURE:
<223> OTHER INFORMATION: Synthetic

<400> SEQUENCE: 60
gaaaaaaaaa aacgctaaaa atacgacg                                28

<210> SEQ ID NO 61
<211> LENGTH: 21
<212> TYPE: DNA
<213> ORGANISM: Artificial sequence
<220> FEATURE:
<223> OTHER INFORMATION: Synthetic

<400> SEQUENCE: 61
tagcgcgtag tggtcgtagt c                                       21

<210> SEQ ID NO 62
<211> LENGTH: 18
<212> TYPE: DNA
<213> ORGANISM: Artificial sequence
<220> FEATURE:
<223> OTHER INFORMATION: Synthetic

<400> SEQUENCE: 62
cctccgccgc tacaaccg                                           18

<210> SEQ ID NO 63
<211> LENGTH: 22
<212> TYPE: DNA
```

```
<213> ORGANISM: Artificial sequence
<220> FEATURE:
<223> OTHER INFORMATION: Synthetic

<400> SEQUENCE: 63
tcgttgtttt aggatcgcgt tc                                              22

<210> SEQ ID NO 64
<211> LENGTH: 22
<212> TYPE: DNA
<213> ORGANISM: Artificial sequence
<220> FEATURE:
<223> OTHER INFORMATION: Synthetic

<400> SEQUENCE: 64
gacgaacgat aaacgacgac ga                                              22

<210> SEQ ID NO 65
<211> LENGTH: 21
<212> TYPE: DNA
<213> ORGANISM: Artificial sequence
<220> FEATURE:
<223> OTHER INFORMATION: Synthetic

<400> SEQUENCE: 65
ttcggtcgcg ttgttcgtta c                                               21

<210> SEQ ID NO 66
<211> LENGTH: 25
<212> TYPE: DNA
<213> ORGANISM: Artificial sequence
<220> FEATURE:
<223> OTHER INFORMATION: Synthetic

<400> SEQUENCE: 66
aaacgaaaaa caactcgaat aacga                                           25

<210> SEQ ID NO 67
<211> LENGTH: 18
<212> TYPE: DNA
<213> ORGANISM: Artificial sequence
<220> FEATURE:
<223> OTHER INFORMATION: Synthetic

<400> SEQUENCE: 67
agtcggggtc ggagtcgc                                                   18

<210> SEQ ID NO 68
<211> LENGTH: 23
<212> TYPE: DNA
<213> ORGANISM: Artificial sequence
<220> FEATURE:
<223> OTHER INFORMATION: Synthetic

<400> SEQUENCE: 68
ataaatccct ccgaaaccca cga                                             23

<210> SEQ ID NO 69
<211> LENGTH: 21
<212> TYPE: DNA
<213> ORGANISM: Artificial sequence
<220> FEATURE:
<223> OTHER INFORMATION: Synthetic

<400> SEQUENCE: 69
tcggaagtga cgtagggtag c                                               21
```

<210> SEQ ID NO 70
<211> LENGTH: 19
<212> TYPE: DNA
<213> ORGANISM: Artificial sequence
<220> FEATURE:
<223> OTHER INFORMATION: Synthetic

<400> SEQUENCE: 70
cacacgcccg ctaacacga                                        19

<210> SEQ ID NO 71
<211> LENGTH: 21
<212> TYPE: DNA
<213> ORGANISM: Artificial sequence
<220> FEATURE:
<223> OTHER INFORMATION: Synthetic

<400> SEQUENCE: 71
gcgcgttcgg gtttatattg c                                     21

<210> SEQ ID NO 72
<211> LENGTH: 20
<212> TYPE: DNA
<213> ORGANISM: Artificial sequence
<220> FEATURE:
<223> OTHER INFORMATION: Synthetic

<400> SEQUENCE: 72
gaccaactac cgctactcga                                       20

<210> SEQ ID NO 73
<211> LENGTH: 20
<212> TYPE: DNA
<213> ORGANISM: Artificial sequence
<220> FEATURE:
<223> OTHER INFORMATION: Synthetic

<400> SEQUENCE: 73
aggggagaat tcgcggttc                                        20

<210> SEQ ID NO 74
<211> LENGTH: 24
<212> TYPE: DNA
<213> ORGANISM: Artificial sequence
<220> FEATURE:
<223> OTHER INFORMATION: Synthetic

<400> SEQUENCE: 74
aactaaatta aacctcaacc gccg                                  24

<210> SEQ ID NO 75
<211> LENGTH: 20
<212> TYPE: DNA
<213> ORGANISM: Artificial sequence
<220> FEATURE:
<223> OTHER INFORMATION: Synthetic

<400> SEQUENCE: 75
ttaggaggcg aggtttgcgc                                       20

<210> SEQ ID NO 76
<211> LENGTH: 28
<212> TYPE: DNA
<213> ORGANISM: Artificial sequence
<220> FEATURE:

<223> OTHER INFORMATION: Synthetic

<400> SEQUENCE: 76
gacgaaaccg taacgaaaat aaaaacga                          28

<210> SEQ ID NO 77
<211> LENGTH: 24
<212> TYPE: DNA
<213> ORGANISM: Artificial sequence
<220> FEATURE:
<223> OTHER INFORMATION: Synthetic

<400> SEQUENCE: 77
cgaactatcc gaaaaaacga cgaa                              24

<210> SEQ ID NO 78
<211> LENGTH: 22
<212> TYPE: DNA
<213> ORGANISM: Artificial sequence
<220> FEATURE:
<223> OTHER INFORMATION: Synthetic

<400> SEQUENCE: 78
gcgacgcgag cgttaattt tc                                 22

<210> SEQ ID NO 79
<211> LENGTH: 23
<212> TYPE: DNA
<213> ORGANISM: Artificial sequence
<220> FEATURE:
<223> OTHER INFORMATION: Synthetic

<400> SEQUENCE: 79
ttcgcgtata tattcgtcga gtc                               23

<210> SEQ ID NO 80
<211> LENGTH: 20
<212> TYPE: DNA
<213> ORGANISM: Artificial sequence
<220> FEATURE:
<223> OTHER INFORMATION: Synthetic

<400> SEQUENCE: 80
cacgaccact atcacgacga                                   20

<210> SEQ ID NO 81
<211> LENGTH: 22
<212> TYPE: DNA
<213> ORGANISM: Artificial sequence
<220> FEATURE:
<223> OTHER INFORMATION: Synthetic

<400> SEQUENCE: 81
gtacgtcggt ttagttcgta gc                                22

<210> SEQ ID NO 82
<211> LENGTH: 21
<212> TYPE: DNA
<213> ORGANISM: Artificial sequence
<220> FEATURE:
<223> OTHER INFORMATION: Synthetic

<400> SEQUENCE: 82
ccgaaacgcg atatcaaccg a                                 21

<210> SEQ ID NO 83
<211> LENGTH: 20
<212> TYPE: DNA
<213> ORGANISM: Artificial sequence
<220> FEATURE:
<223> OTHER INFORMATION: Synthetic

<400> SEQUENCE: 83
cgggcggtta gagggttgtc                                                  20

<210> SEQ ID NO 84
<211> LENGTH: 26
<212> TYPE: DNA
<213> ORGANISM: Artificial sequence
<220> FEATURE:
<223> OTHER INFORMATION: Synthetic

<400> SEQUENCE: 84
ctcgaaaatt cgtaaaaacc ctccga                                           26

<210> SEQ ID NO 85
<211> LENGTH: 29
<212> TYPE: DNA
<213> ORGANISM: Artificial sequence
<220> FEATURE:
<223> OTHER INFORMATION: Synthetic

<400> SEQUENCE: 85
cgagtagttt tttttttat cgtttagac                                         29

<210> SEQ ID NO 86
<211> LENGTH: 24
<212> TYPE: DNA
<213> ORGANISM: Artificial sequence
<220> FEATURE:
<223> OTHER INFORMATION: Synthetic

<400> SEQUENCE: 86
caaaaaacga cacgtaaacg atcg                                             24

<210> SEQ ID NO 87
<211> LENGTH: 24
<212> TYPE: DNA
<213> ORGANISM: Artificial sequence
<220> FEATURE:
<223> OTHER INFORMATION: Synthetic

<400> SEQUENCE: 87
gtttcgtttt gcgttttttt gcgc                                             24

<210> SEQ ID NO 88
<211> LENGTH: 19
<212> TYPE: DNA
<213> ORGANISM: Artificial sequence
<220> FEATURE:
<223> OTHER INFORMATION: Synthetic

<400> SEQUENCE: 88
tcccgaatcg ctactccga                                                   19

<210> SEQ ID NO 89
<211> LENGTH: 17
<212> TYPE: DNA
<213> ORGANISM: Artificial sequence
<220> FEATURE:
<223> OTHER INFORMATION: Synthetic

```
<400> SEQUENCE: 89
gcggttaggc gggttgc                                                   17

<210> SEQ ID NO 90
<211> LENGTH: 25
<212> TYPE: DNA
<213> ORGANISM: Artificial sequence
<220> FEATURE:
<223> OTHER INFORMATION: Synthetic

<400> SEQUENCE: 90
attatatcaa tcccaaaaac acgcg                                          25

<210> SEQ ID NO 91
<211> LENGTH: 22
<212> TYPE: DNA
<213> ORGANISM: Artificial sequence
<220> FEATURE:
<223> OTHER INFORMATION: Synthetic

<400> SEQUENCE: 91 tattttcga attcgagttc gc                                              22

<210> SEQ ID NO 92
<211> LENGTH: 22
<212> TYPE: DNA
<213> ORGANISM: Artificial sequence
<220> FEATURE:
<223> OTHER INFORMATION: Synthetic

<400> SEQUENCE: 92
tcacccgata aaacgaaaa cg                                              22

<210> SEQ ID NO 93
<211> LENGTH: 21
<212> TYPE: DNA
<213> ORGANISM: Artificial sequence
<220> FEATURE:
<223> OTHER INFORMATION: Synthetic

<400> SEQUENCE: 93
gcgtcgttag tagtacgaag c                                              21

<210> SEQ ID NO 94
<211> LENGTH: 21
<212> TYPE: DNA
<213> ORGANISM: Artificial sequence
<220> FEATURE:
<223> OTHER INFORMATION: Synthetic

<400> SEQUENCE: 94
gcacctcaac gaaaacaccg a                                              21

<210> SEQ ID NO 95
<211> LENGTH: 23
<212> TYPE: DNA
<213> ORGANISM: Artificial sequence
<220> FEATURE:
<223> OTHER INFORMATION: Synthetic

<400> SEQUENCE: 95
tcgaggcggt taattttatt cgc                                            23

<210> SEQ ID NO 96
<211> LENGTH: 23
```

```
<212> TYPE: DNA
<213> ORGANISM: Artificial sequence
<220> FEATURE:
<223> OTHER INFORMATION: Synthetic

<400> SEQUENCE: 96
gctctaaccc aaatacgcta cga                                              23

<210> SEQ ID NO 97
<211> LENGTH: 22
<212> TYPE: DNA
<213> ORGANISM: Artificial sequence
<220> FEATURE:
<223> OTHER INFORMATION: Synthetic

<400> SEQUENCE: 97
tcggtttcga ggtaagttta gc                                               22

<210> SEQ ID NO 98
<211> LENGTH: 23
<212> TYPE: DNA
<213> ORGANISM: Artificial sequence
<220> FEATURE:
<223> OTHER INFORMATION: Synthetic

<400> SEQUENCE: 98
cacttcgaaa caaaattacg cga                                              23

<210> SEQ ID NO 99
<211> LENGTH: 20
<212> TYPE: DNA
<213> ORGANISM: Artificial sequence
<220> FEATURE:
<223> OTHER INFORMATION: Synthetic

<400> SEQUENCE: 99
ggaagcggac gttttcgttc                                                  20

<210> SEQ ID NO 100
<211> LENGTH: 22
<212> TYPE: DNA
<213> ORGANISM: Artificial sequence
<220> FEATURE:
<223> OTHER INFORMATION: Synthetic

<400> SEQUENCE: 100
acccaaaatc cgaaaacgac ga                                               22

<210> SEQ ID NO 101
<211> LENGTH: 19
<212> TYPE: DNA
<213> ORGANISM: Artificial sequence
<220> FEATURE:
<223> OTHER INFORMATION: Synthetic

<400> SEQUENCE: 101
aggttgcggg cgtgatttc                                                   19

<210> SEQ ID NO 102
<211> LENGTH: 20
<212> TYPE: DNA
<213> ORGANISM: Artificial sequence
<220> FEATURE:
<223> OTHER INFORMATION: Synthetic

<400> SEQUENCE: 102
```

```
ccaaaaccac gcgaacacga                                            20

<210> SEQ ID NO 103
<211> LENGTH: 20
<212> TYPE: DNA
<213> ORGANISM: Artificial sequence
<220> FEATURE:
<223> OTHER INFORMATION: Synthetic

<400> SEQUENCE: 103
gttcggagtg tcgtagtcgc                                            20

<210> SEQ ID NO 104
<211> LENGTH: 21
<212> TYPE: DNA
<213> ORGANISM: Artificial sequence
<220> FEATURE:
<223> OTHER INFORMATION: Synthetic

<400> SEQUENCE: 104
aatctcgcct acgaaacgac g                                          21

<210> SEQ ID NO 105
<211> LENGTH: 22
<212> TYPE: DNA
<213> ORGANISM: Artificial sequence
<220> FEATURE:
<223> OTHER INFORMATION: Synthetic

<400> SEQUENCE: 105
gtttagggac gttttcgttt tc                                         22

<210> SEQ ID NO 106
<211> LENGTH: 20
<212> TYPE: DNA
<213> ORGANISM: Artificial sequence
<220> FEATURE:
<223> OTHER INFORMATION: Synthetic

<400> SEQUENCE: 106
aacgaacgct cgataaccga                                            20

<210> SEQ ID NO 107
<211> LENGTH: 20
<212> TYPE: DNA
<213> ORGANISM: Artificial sequence
<220> FEATURE:
<223> OTHER INFORMATION: Synthetic

<400> SEQUENCE: 107
tttgggtcgg gttaggtcgc                                            20

<210> SEQ ID NO 108
<211> LENGTH: 25
<212> TYPE: DNA
<213> ORGANISM: Artificial sequence
<220> FEATURE:
<223> OTHER INFORMATION: Synthetic

<400> SEQUENCE: 108
gaaaccaaaa aaacgctaac tcgta                                      25

<210> SEQ ID NO 109
<211> LENGTH: 20
<212> TYPE: DNA
<213> ORGANISM: Artificial sequence
```

<220> FEATURE:
<223> OTHER INFORMATION: Synthetic

<400> SEQUENCE: 109
cgttgttgga gtttggcgtc                                                    20

<210> SEQ ID NO 110
<211> LENGTH: 21
<212> TYPE: DNA
<213> ORGANISM: Artificial sequence
<220> FEATURE:
<223> OTHER INFORMATION: Synthetic

<400> SEQUENCE: 110
tacccgaacc gcgataaaac g                                                  21

<210> SEQ ID NO 111
<211> LENGTH: 25
<212> TYPE: DNA
<213> ORGANISM: Artificial sequence
<220> FEATURE:
<223> OTHER INFORMATION: Synthetic

<400> SEQUENCE: 111
ggtatagttc ggtttttagt cgttc                                              25

<210> SEQ ID NO 112
<211> LENGTH: 24
<212> TYPE: DNA
<213> ORGANISM: Artificial sequence
<220> FEATURE:
<223> OTHER INFORMATION: Synthetic

<400> SEQUENCE: 112
tcttttcctc cgaaaaccga aacg                                               24

<210> SEQ ID NO 113
<211> LENGTH: 23
<212> TYPE: DNA
<213> ORGANISM: Artificial sequence
<220> FEATURE:
<223> OTHER INFORMATION: Synthetic

<400> SEQUENCE: 113
ggttacggtt agtattcgga ttc                                                23

<210> SEQ ID NO 114
<211> LENGTH: 20
<212> TYPE: DNA
<213> ORGANISM: Artificial sequence
<220> FEATURE:
<223> OTHER INFORMATION: Synthetic

<400> SEQUENCE: 114
atatcaaccg cctacccgcg                                                    20

<210> SEQ ID NO 115
<211> LENGTH: 24
<212> TYPE: DNA
<213> ORGANISM: Artificial sequence
<220> FEATURE:
<223> OTHER INFORMATION: Synthetic

<400> SEQUENCE: 115
ttttgtttta atgcggcggt tggc                                               24

<210> SEQ ID NO 116
<211> LENGTH: 22
<212> TYPE: DNA
<213> ORGANISM: Artificial sequence
<220> FEATURE:
<223> OTHER INFORMATION: Synthetic

<400> SEQUENCE: 116
tatccgaact atccgctacc ga                                              22

<210> SEQ ID NO 117
<211> LENGTH: 19
<212> TYPE: DNA
<213> ORGANISM: Artificial sequence
<220> FEATURE:
<223> OTHER INFORMATION: Synthetic

<400> SEQUENCE: 117
ggtcgcgtcg ttttcgatc                                                  19

<210> SEQ ID NO 118
<211> LENGTH: 17
<212> TYPE: DNA
<213> ORGANISM: Artificial sequence
<220> FEATURE:
<223> OTHER INFORMATION: Synthetic

<400> SEQUENCE: 118
gccgcaaacg ccgacga                                                    17

<210> SEQ ID NO 119
<211> LENGTH: 21
<212> TYPE: DNA
<213> ORGANISM: Artificial sequence
<220> FEATURE:
<223> OTHER INFORMATION: Synthetic

<400> SEQUENCE: 119
aatcggcggt agtacgagta c                                               21

<210> SEQ ID NO 120
<211> LENGTH: 26
<212> TYPE: DNA
<213> ORGANISM: Artificial sequence
<220> FEATURE:
<223> OTHER INFORMATION: Synthetic

<400> SEQUENCE: 120
aaaccaaatc cgtaacgata ataacg                                          26

<210> SEQ ID NO 121
<211> LENGTH: 26
<212> TYPE: DNA
<213> ORGANISM: Artificial sequence
<220> FEATURE:
<223> OTHER INFORMATION: Synthetic

<400> SEQUENCE: 121
gagttttgtt ttcgaaatta tttcgc                                          26

<210> SEQ ID NO 122
<211> LENGTH: 18
<212> TYPE: DNA
<213> ORGANISM: Artificial sequence
<220> FEATURE:
<223> OTHER INFORMATION: Synthetic

```
<400> SEQUENCE: 122
cccgaattac cgacgacg                                            18

<210> SEQ ID NO 123
<211> LENGTH: 21
<212> TYPE: DNA
<213> ORGANISM: Artificial sequence
<220> FEATURE:
<223> OTHER INFORMATION: Synthetic

<400> SEQUENCE: 123
aggttcgggt tcgacgattt c                                        21

<210> SEQ ID NO 124
<211> LENGTH: 21
<212> TYPE: DNA
<213> ORGANISM: Artificial sequence
<220> FEATURE:
<223> OTHER INFORMATION: Synthetic

<400> SEQUENCE: 124
aactctacaa cgccgaaacc g                                        21

<210> SEQ ID NO 125
<211> LENGTH: 23
<212> TYPE: DNA
<213> ORGANISM: Artificial sequence
<220> FEATURE:
<223> OTHER INFORMATION: Synthetic

<400> SEQUENCE: 125
ttagttcgtt tagcgatggc gtc                                      23

<210> SEQ ID NO 126
<211> LENGTH: 20
<212> TYPE: DNA
<213> ORGANISM: Artificial sequence
<220> FEATURE:
<223> OTHER INFORMATION: Synthetic

<400> SEQUENCE: 126
ccgaaactat cccgcaacga                                          20

<210> SEQ ID NO 127
<211> LENGTH: 21
<212> TYPE: DNA
<213> ORGANISM: Artificial sequence
<220> FEATURE:
<223> OTHER INFORMATION: Synthetic

<400> SEQUENCE: 127
ttcgtcgttt gggttatcgg c                                        21

<210> SEQ ID NO 128
<211> LENGTH: 23
<212> TYPE: DNA
<213> ORGANISM: Artificial sequence
<220> FEATURE:
<223> OTHER INFORMATION: Synthetic

<400> SEQUENCE: 128
gccctaaaac taaaacaacc gcg                                      23

<210> SEQ ID NO 129
```

```
<211> LENGTH: 22
<212> TYPE: DNA
<213> ORGANISM: Artificial sequence
<220> FEATURE:
<223> OTHER INFORMATION: Synthetic

<400> SEQUENCE: 129
ggttgtcgtt ttagttcgtc gc                                        22

<210> SEQ ID NO 130
<211> LENGTH: 19
<212> TYPE: DNA
<213> ORGANISM: Artificial sequence
<220> FEATURE:
<223> OTHER INFORMATION: Synthetic

<400> SEQUENCE: 130
gcgaaaacgc ccgaaccga                                            19

<210> SEQ ID NO 131
<211> LENGTH: 22
<212> TYPE: DNA
<213> ORGANISM: Artificial sequence
<220> FEATURE:
<223> OTHER INFORMATION: Synthetic

<400> SEQUENCE: 131
tcgtttggga gacgtattcg tc                                        22

<210> SEQ ID NO 132
<211> LENGTH: 25
<212> TYPE: DNA
<213> ORGANISM: Artificial sequence
<220> FEATURE:
<223> OTHER INFORMATION: Synthetic

<400> SEQUENCE: 132
actcgaaaaa tttccgaact aacga                                     25

<210> SEQ ID NO 133
<211> LENGTH: 20
<212> TYPE: DNA
<213> ORGANISM: Artificial sequence
<220> FEATURE:
<223> OTHER INFORMATION: Synthetic

<400> SEQUENCE: 133
tcggcggttt tcgttatcgc                                           20

<210> SEQ ID NO 134
<211> LENGTH: 21
<212> TYPE: DNA
<213> ORGANISM: Artificial sequence
<220> FEATURE:
<223> OTHER INFORMATION: Synthetic

<400> SEQUENCE: 134 ccacgaaaact cgcaactacg a                                        21

<210> SEQ ID NO 135
<211> LENGTH: 25
<212> TYPE: DNA
<213> ORGANISM: Artificial sequence
<220> FEATURE:
<223> OTHER INFORMATION: Synthetic

<400> SEQUENCE: 135
```
cgtttattta gcgtaatcgt ttcgc                                             25

<210> SEQ ID NO 136
<211> LENGTH: 24
<212> TYPE: DNA
<213> ORGANISM: Artificial sequence
<220> FEATURE:
<223> OTHER INFORMATION: Synthetic

<400> SEQUENCE: 136
gaataacgaa cgttcgacta ccga                                              24

<210> SEQ ID NO 137
<211> LENGTH: 24
<212> TYPE: DNA
<213> ORGANISM: Artificial sequence
<220> FEATURE:
<223> OTHER INFORMATION: Synthetic

<400> SEQUENCE: 137
cggacgagat tagttttcgt tagc                                              24

<210> SEQ ID NO 138
<211> LENGTH: 24
<212> TYPE: DNA
<213> ORGANISM: Artificial sequence
<220> FEATURE:
<223> OTHER INFORMATION: Synthetic

<400> SEQUENCE: 138
tcgtcaatca ctcgacgaaa acga                                              24

<210> SEQ ID NO 139
<211> LENGTH: 22
<212> TYPE: DNA
<213> ORGANISM: Artificial sequence
<220> FEATURE:
<223> OTHER INFORMATION: Synthetic

<400> SEQUENCE: 139
tcggttcgta ggtatacgtg tc                                                22

<210> SEQ ID NO 140
<211> LENGTH: 22
<212> TYPE: DNA
<213> ORGANISM: Artificial sequence
<220> FEATURE:
<223> OTHER INFORMATION: Synthetic

<400> SEQUENCE: 140
gctactacca atacttccgc ga                                                22

<210> SEQ ID NO 141
<211> LENGTH: 21
<212> TYPE: DNA
<213> ORGANISM: Artificial sequence
<220> FEATURE:
<223> OTHER INFORMATION: Synthetic

<400> SEQUENCE: 141
gttagacggt tttagtttcg c                                                 21

<210> SEQ ID NO 142
<211> LENGTH: 20
<212> TYPE: DNA

```
<213> ORGANISM: Artificial sequence
<220> FEATURE:
<223> OTHER INFORMATION: Synthetic

<400> SEQUENCE: 142
aaaaacccga cgacgattcg                                                    20

<210> SEQ ID NO 143
<211> LENGTH: 21
<212> TYPE: DNA
<213> ORGANISM: Artificial sequence
<220> FEATURE:
<223> OTHER INFORMATION: Synthetic

<400> SEQUENCE: 143
gttagagttc gcgtagcgta c                                                  21

<210> SEQ ID NO 144
<211> LENGTH: 25
<212> TYPE: DNA
<213> ORGANISM: Artificial sequence
<220> FEATURE:
<223> OTHER INFORMATION: Synthetic

<400> SEQUENCE: 144
gaaaaaacca accgaacgaa aacga                                              25

<210> SEQ ID NO 145
<211> LENGTH: 19
<212> TYPE: DNA
<213> ORGANISM: Artificial sequence
<220> FEATURE:
<223> OTHER INFORMATION: Synthetic

<400> SEQUENCE: 145
cggggcgttt cgatgtcgc                                                     19

<210> SEQ ID NO 146
<211> LENGTH: 24
<212> TYPE: DNA
<213> ORGANISM: Artificial sequence
<220> FEATURE:
<223> OTHER INFORMATION: Synthetic

<400> SEQUENCE: 146
ccgaacgacc aaataaaacc aacg                                               24

<210> SEQ ID NO 147
<211> LENGTH: 22
<212> TYPE: DNA
<213> ORGANISM: Artificial sequence
<220> FEATURE:
<223> OTHER INFORMATION: Synthetic

<400> SEQUENCE: 147
cgttttatgt tgggagcgtt cg                                                 22

<210> SEQ ID NO 148
<211> LENGTH: 20
<212> TYPE: DNA
<213> ORGANISM: Artificial sequence
<220> FEATURE:
<223> OTHER INFORMATION: Synthetic

<400> SEQUENCE: 148
gaccgaaccg cgtctaaacg                                                    20
```

<210> SEQ ID NO 149
<211> LENGTH: 21
<212> TYPE: DNA
<213> ORGANISM: Artificial sequence
<220> FEATURE:
<223> OTHER INFORMATION: Synthetic

<400> SEQUENCE: 149
tacgtatcga ggttgcgtcg c                                             21

<210> SEQ ID NO 150
<211> LENGTH: 25
<212> TYPE: DNA
<213> ORGANISM: Artificial sequence
<220> FEATURE:
<223> OTHER INFORMATION: Synthetic

<400> SEQUENCE: 150
aaactctaaa acgaacgaaa ctcga                                         25

<210> SEQ ID NO 151
<211> LENGTH: 21
<212> TYPE: DNA
<213> ORGANISM: Artificial sequence
<220> FEATURE:
<223> OTHER INFORMATION: Synthetic

<400> SEQUENCE: 151
tcgagacgcg tttttttgcgt c                                            21

<210> SEQ ID NO 152
<211> LENGTH: 20
<212> TYPE: DNA
<213> ORGANISM: Artificial sequence
<220> FEATURE:
<223> OTHER INFORMATION: Synthetic

<400> SEQUENCE: 152
aacgatcccg aaccgccgta                                               20

<210> SEQ ID NO 153
<211> LENGTH: 21
<212> TYPE: DNA
<213> ORGANISM: Artificial sequence
<220> FEATURE:
<223> OTHER INFORMATION: Synthetic

<400> SEQUENCE: 153
cgagtagtgc gttttttcggt c                                            21

<210> SEQ ID NO 154
<211> LENGTH: 22
<212> TYPE: DNA
<213> ORGANISM: Artificial sequence
<220> FEATURE:
<223> OTHER INFORMATION: Synthetic

<400> SEQUENCE: 154
gacaacaacg ataacgacga cg                                            22

<210> SEQ ID NO 155
<211> LENGTH: 22
<212> TYPE: DNA
<213> ORGANISM: Artificial sequence
<220> FEATURE:

```
<223> OTHER INFORMATION: Synthetic

<400> SEQUENCE: 155
agcgtgcgtt attcggtttt gc                                              22

<210> SEQ ID NO 156
<211> LENGTH: 23
<212> TYPE: DNA
<213> ORGANISM: Artificial sequence
<220> FEATURE:
<223> OTHER INFORMATION: Synthetic

<400> SEQUENCE: 156
acctacgatt cgtaaaccga acg                                             23

<210> SEQ ID NO 157
<211> LENGTH: 23
<212> TYPE: DNA
<213> ORGANISM: Artificial sequence
<220> FEATURE:
<223> OTHER INFORMATION: Synthetic

<400> SEQUENCE: 157
agttcgcgtt ttttcggtc gtc                                              23

<210> SEQ ID NO 158
<211> LENGTH: 21
<212> TYPE: DNA
<213> ORGANISM: Artificial sequence
<220> FEATURE:
<223> OTHER INFORMATION: Synthetic

<400> SEQUENCE: 158
aaccgacgca ccgactaacg a                                               21

<210> SEQ ID NO 159
<211> LENGTH: 22
<212> TYPE: DNA
<213> ORGANISM: Artificial sequence
<220> FEATURE:
<223> OTHER INFORMATION: Synthetic

<400> SEQUENCE: 159
ttgcgtcgtt tgcgttttc gc                                               22

<210> SEQ ID NO 160
<211> LENGTH: 20
<212> TYPE: DNA
<213> ORGANISM: Artificial sequence
<220> FEATURE:
<223> OTHER INFORMATION: Synthetic

<400> SEQUENCE: 160
caactcgcca atctcgccga                                                 20

<210> SEQ ID NO 161
<211> LENGTH: 18
<212> TYPE: DNA
<213> ORGANISM: Artificial sequence
<220> FEATURE:
<223> OTHER INFORMATION: Synthetic

<400> SEQUENCE: 161
tattgcgggg aggtgttc                                                   18
```

```
<210> SEQ ID NO 162
<211> LENGTH: 24
<212> TYPE: DNA
<213> ORGANISM: Artificial sequence
<220> FEATURE:
<223> OTHER INFORMATION: Synthetic

<400> SEQUENCE: 162
tcaaaaaata attaaccgaa ccga                                              24

<210> SEQ ID NO 163
<211> LENGTH: 24
<212> TYPE: DNA
<213> ORGANISM: Artificial sequence
<220> FEATURE:
<223> OTHER INFORMATION: Synthetic

<400> SEQUENCE: 163
ttagttttcg aagttttcgt tcgc                                              24

<210> SEQ ID NO 164
<211> LENGTH: 19
<212> TYPE: DNA
<213> ORGANISM: Artificial sequence
<220> FEATURE:
<223> OTHER INFORMATION: Synthetic

<400> SEQUENCE: 164
tccgacccta tcccgacga                                                    19

<210> SEQ ID NO 165
<211> LENGTH: 27
<212> TYPE: DNA
<213> ORGANISM: Artificial sequence
<220> FEATURE:
<223> OTHER INFORMATION: Synthetic

<400> SEQUENCE: 165
gattagttaa ttaacgataa agttcgc                                           27

<210> SEQ ID NO 166
<211> LENGTH: 23
<212> TYPE: DNA
<213> ORGANISM: Artificial sequence
<220> FEATURE:
<223> OTHER INFORMATION: Synthetic

<400> SEQUENCE: 166
ccgaaaacgc ataatatcct cga                                               23

<210> SEQ ID NO 167
<211> LENGTH: 26
<212> TYPE: DNA
<213> ORGANISM: Artificial sequence
<220> FEATURE:
<223> OTHER INFORMATION: Synthetic

<400> SEQUENCE: 167
ttggagagtt tttcgaattt tttcgc                                            26

<210> SEQ ID NO 168
<211> LENGTH: 19
<212> TYPE: DNA
<213> ORGANISM: Artificial sequence
<220> FEATURE:
<223> OTHER INFORMATION: Synthetic
```

<400> SEQUENCE: 168
gaaaaccacc ctaacgccg                                                  19

<210> SEQ ID NO 169
<211> LENGTH: 17
<212> TYPE: DNA
<213> ORGANISM: Artificial sequence
<220> FEATURE:
<223> OTHER INFORMATION: Synthetic

<400> SEQUENCE: 169
cgcggggttc gtaggtc                                                    17

<210> SEQ ID NO 170
<211> LENGTH: 23
<212> TYPE: DNA
<213> ORGANISM: Artificial sequence
<220> FEATURE:
<223> OTHER INFORMATION: Synthetic

<400> SEQUENCE: 170
cgacaaacaa caacgaaatc gaa                                             23

<210> SEQ ID NO 171
<211> LENGTH: 22
<212> TYPE: DNA
<213> ORGANISM: Artificial sequence
<220> FEATURE:
<223> OTHER INFORMATION: Synthetic

<400> SEQUENCE: 171
agtagcggtt atagtggcgt tc                                              22

<210> SEQ ID NO 172
<211> LENGTH: 22
<212> TYPE: DNA
<213> ORGANISM: Artificial sequence
<220> FEATURE:
<223> OTHER INFORMATION: Synthetic

<400> SEQUENCE: 172
gcattcgcga cgaaaacaaa cg                                              22

<210> SEQ ID NO 173
<211> LENGTH: 20
<212> TYPE: DNA
<213> ORGANISM: Artificial sequence
<220> FEATURE:
<223> OTHER INFORMATION: Synthetic

<400> SEQUENCE: 173
gtattgaggt cggcgttgtc                                                 20

<210> SEQ ID NO 174
<211> LENGTH: 19
<212> TYPE: DNA
<213> ORGANISM: Artificial sequence
<220> FEATURE:
<223> OTHER INFORMATION: Synthetic

<400> SEQUENCE: 174
ccgcccgaat aaaccgcga                                                  19

<210> SEQ ID NO 175
<211> LENGTH: 20

```
<212> TYPE: DNA
<213> ORGANISM: Artificial sequence
<220> FEATURE:
<223> OTHER INFORMATION: Synthetic

<400> SEQUENCE: 175
cgtagttcgg cgtagttcgc                                                      20

<210> SEQ ID NO 176
<211> LENGTH: 21
<212> TYPE: DNA
<213> ORGANISM: Artificial sequence
<220> FEATURE:
<223> OTHER INFORMATION: Synthetic

<400> SEQUENCE: 176
aacccgcccg acgacaatac g                                                    21

<210> SEQ ID NO 177
<211> LENGTH: 20
<212> TYPE: DNA
<213> ORGANISM: Artificial sequence
<220> FEATURE:
<223> OTHER INFORMATION: Synthetic

<400> SEQUENCE: 177
gtcgagcgcg ttcgttgtac                                                      20

<210> SEQ ID NO 178
<211> LENGTH: 22
<212> TYPE: DNA
<213> ORGANISM: Artificial sequence
<220> FEATURE:
<223> OTHER INFORMATION: Synthetic

<400> SEQUENCE: 178
gacccgaaaa ataaatcccg aa                                                   22

<210> SEQ ID NO 179
<211> LENGTH: 24
<212> TYPE: DNA
<213> ORGANISM: Artificial sequence
<220> FEATURE:
<223> OTHER INFORMATION: Synthetic

<400> SEQUENCE: 179 gatttttta gtttgttcga cggc                                                  24

<210> SEQ ID NO 180
<211> LENGTH: 25
<212> TYPE: DNA
<213> ORGANISM: Artificial sequence
<220> FEATURE:
<223> OTHER INFORMATION: Synthetic

<400> SEQUENCE: 180
aaaattacta aacgcgaaat cgacg                                                25

<210> SEQ ID NO 181
<211> LENGTH: 26
<212> TYPE: DNA
<213> ORGANISM: Artificial sequence
<220> FEATURE:
<223> OTHER INFORMATION: Synthetic

<400> SEQUENCE: 181
```

```
taatgggatg ataaatgtat tcgcgg                                          26

<210> SEQ ID NO 182
<211> LENGTH: 26
<212> TYPE: DNA
<213> ORGANISM: Artificial sequence
<220> FEATURE:
<223> OTHER INFORMATION: Synthetic

<400> SEQUENCE: 182
accgcctaat ccaactcgaa ctcgta                                          26

<210> SEQ ID NO 183
<211> LENGTH: 22
<212> TYPE: DNA
<213> ORGANISM: Artificial sequence
<220> FEATURE:
<223> OTHER INFORMATION: Synthetic

<400> SEQUENCE: 183
ggtgttttta aagggtcgtc gt                                              22

<210> SEQ ID NO 184
<211> LENGTH: 19
<212> TYPE: DNA
<213> ORGANISM: Artificial sequence
<220> FEATURE:
<223> OTHER INFORMATION: Synthetic

<400> SEQUENCE: 184
gacccgactc ctccacgta                                                  19

<210> SEQ ID NO 185
<211> LENGTH: 30
<212> TYPE: DNA
<213> ORGANISM: Artificial sequence
<220> FEATURE:
<223> OTHER INFORMATION: Synthetic

<400> SEQUENCE: 185
ggaagtttat agtggtttcg gcgggtaggc                                      30

<210> SEQ ID NO 186
<211> LENGTH: 22
<212> TYPE: DNA
<213> ORGANISM: Artificial sequence
<220> FEATURE:
<223> OTHER INFORMATION: Synthetic

<400> SEQUENCE: 186
gcgaaaaacg ttcgaacccg cg                                              22

<210> SEQ ID NO 187
<211> LENGTH: 28
<212> TYPE: DNA
<213> ORGANISM: Artificial sequence
<220> FEATURE:
<223> OTHER INFORMATION: Synthetic

<400> SEQUENCE: 187
tgtcgtcgtc gcgttatttt agttgttc                                        28

<210> SEQ ID NO 188
<211> LENGTH: 22
<212> TYPE: DNA
<213> ORGANISM: Artificial sequence
```

```
<220> FEATURE:
<223> OTHER INFORMATION: Synthetic

<400> SEQUENCE: 188
aaccgccgtc caaaccatcg ta                                        22

<210> SEQ ID NO 189
<211> LENGTH: 25
<212> TYPE: DNA
<213> ORGANISM: Artificial sequence
<220> FEATURE:
<223> OTHER INFORMATION: Synthetic

<400> SEQUENCE: 189
gaagagttag ggttcgggac gcgag                                     25

<210> SEQ ID NO 190
<211> LENGTH: 25
<212> TYPE: DNA
<213> ORGANISM: Artificial sequence
<220> FEATURE:
<223> OTHER INFORMATION: Synthetic

<400> SEQUENCE: 190
aacgaccaaa taaacgccga accga                                     25

<210> SEQ ID NO 191
<211> LENGTH: 25
<212> TYPE: DNA
<213> ORGANISM: Artificial sequence
<220> FEATURE:
<223> OTHER INFORMATION: Synthetic

<400> SEQUENCE: 191
cgtaggagcg attaggtggg cgtcg                                     25

<210> SEQ ID NO 192
<211> LENGTH: 23
<212> TYPE: DNA
<213> ORGANISM: Artificial sequence
<220> FEATURE:
<223> OTHER INFORMATION: Synthetic

<400> SEQUENCE: 192
aaaccaaaac ccgaaacgcg aaa                                       23

<210> SEQ ID NO 193
<211> LENGTH: 26
<212> TYPE: DNA
<213> ORGANISM: Artificial sequence
<220> FEATURE:
<223> OTHER INFORMATION: Synthetic

<400> SEQUENCE: 193
cgattcgggg gatggattag cgttgt                                    26

<210> SEQ ID NO 194
<211> LENGTH: 30
<212> TYPE: DNA
<213> ORGANISM: Artificial sequence
<220> FEATURE:
<223> OTHER INFORMATION: Synthetic

<400> SEQUENCE: 194
cgaaatcccc ctaacgaaaa tctccgaaaa                                30
```

```
<210> SEQ ID NO 195
<211> LENGTH: 25
<212> TYPE: DNA
<213> ORGANISM: Artificial sequence
<220> FEATURE:
<223> OTHER INFORMATION: Synthetic

<400> SEQUENCE: 195
cggggttttt ttagcggggg ttttc                                              25

<210> SEQ ID NO 196
<211> LENGTH: 29
<212> TYPE: DNA
<213> ORGANISM: Artificial sequence
<220> FEATURE:
<223> OTHER INFORMATION: Synthetic

<400> SEQUENCE: 196
cgcgatccga aaataaatt aacgctact                                           29

<210> SEQ ID NO 197
<211> LENGTH: 20
<212> TYPE: DNA
<213> ORGANISM: Artificial sequence
<220> FEATURE:
<223> OTHER INFORMATION: Synthetic

<400> SEQUENCE: 197
agcggttcga gttgggacgg                                                    20

<210> SEQ ID NO 198
<211> LENGTH: 24
<212> TYPE: DNA
<213> ORGANISM: Artificial sequence
<220> FEATURE:
<223> OTHER INFORMATION: Synthetic

<400> SEQUENCE: 198
gaaaaacgcg atcgccgaaa acgc                                               24

<210> SEQ ID NO 199
<211> LENGTH: 28
<212> TYPE: DNA
<213> ORGANISM: Artificial sequence
<220> FEATURE:
<223> OTHER INFORMATION: Synthetic

<400> SEQUENCE: 199
gaaggttatt aatttaatag tcgcggaa                                           28

<210> SEQ ID NO 200
<211> LENGTH: 25
<212> TYPE: DNA
<213> ORGANISM: Artificial sequence
<220> FEATURE:
<223> OTHER INFORMATION: Synthetic

<400> SEQUENCE: 200
aaaaaaaacg ttcccgacga ccgcg                                              25

<210> SEQ ID NO 201
<211> LENGTH: 25
<212> TYPE: DNA
<213> ORGANISM: Artificial sequence
<220> FEATURE:
<223> OTHER INFORMATION: Synthetic
```

```
<400> SEQUENCE: 201
agttgtttta tatatcggcg ttcgg                                            25

<210> SEQ ID NO 202
<211> LENGTH: 23
<212> TYPE: DNA
<213> ORGANISM: Artificial sequence
<220> FEATURE:
<223> OTHER INFORMATION: Synthetic

<400> SEQUENCE: 202
gactatacac gcttaaccgc gaa                                              23
```